US012605428B2

(12) United States Patent
Chivukula et al.

(10) Patent No.: US 12,605,428 B2
(45) Date of Patent: Apr. 21, 2026

(54) KINASE NEK10 AND ITS USE IN TREATING AND DIAGNOSING BRONCHIECTASIS AND OTHER RESPIRATORY DISORDERS

(71) Applicants: The General Hospital Corporation, Boston, MA (US); Whitehead Institute for Biomedical Research, Cambridge, MA (US)

(72) Inventors: Raghu R. Chivukula, Somerville, MA (US); David M. Sabatini, Cambridge, MA (US)

(73) Assignees: The General Hospital Corporation, Boston, MA (US); Whitehead Institute for Biomedical Research, Cambridge, MA (US)

( * ) Notice: Subject to any disclaimer, the term of this patent is extended or adjusted under 35 U.S.C. 154(b) by 817 days.

(21) Appl. No.: 17/793,142

(22) PCT Filed: Jan. 19, 2021

(86) PCT No.: PCT/US2021/013942
§ 371 (c)(1),
(2) Date: Jul. 15, 2022

(87) PCT Pub. No.: WO2021/146704
PCT Pub. Date: Jul. 22, 2021

(65) Prior Publication Data
US 2023/0057418 A1     Feb. 23, 2023

Related U.S. Application Data

(60) Provisional application No. 62/962,434, filed on Jan. 17, 2020, provisional application No. 62/961,817, filed on Jan. 16, 2020.

(51) Int. Cl.
| | |
|---|---|
| *A61K 38/45* | (2006.01) |
| *A61P 11/00* | (2006.01) |
| *G01N 33/573* | (2006.01) |
| *G01N 33/68* | (2006.01) |

(52) U.S. Cl.
CPC ............. *A61K 38/45* (2013.01); *A61P 11/00* (2018.01); *G01N 33/573* (2013.01); *G01N 33/6893* (2013.01); *C12Y 207/11001* (2013.01); *G01N 2800/12* (2013.01)

(58) Field of Classification Search
None
See application file for complete search history.

(56) References Cited

FOREIGN PATENT DOCUMENTS

| | | | | |
|---|---|---|---|---|
| WO | WO-2006040594 A2 * | 4/2006 | ........... | C12N 9/1205 |
| WO | WO-2016201370 A1 * | 12/2016 | ......... | A61K 31/4162 |
| WO | WO-2017173103 A1 * | 10/2017 | ........... | A61K 31/135 |
| WO | WO-2019126696 A1 * | 6/2019 | .............. | A61P 35/00 |

OTHER PUBLICATIONS

Ten Hacken et al., "Treatment of bronchiectasis in adults", British Medical Journal, vol. 335, pp. 1089-1093. (Year: 2007).*
UT Southwestern Medical Center, "Bronchiectasis", https://utswmed.org/conditions-treatments/bronchiectasis/, (accessed Feb. 2025) (Year: 2025).*
Nishikawa et al., "Nonviral Vectors in the New Millennium: Delivery Barriers in Gene Transfer", Human Gene Therapy, vol. 12, pp. 861-870. (Year: 2001).*
Alton et al., "Repeated nebulisation of non-viral CFTR gene therapy in patients with cystic fibrosis: a randomised, double-blind, placebo-controlled, phase 2b trial," Lancet Respir Med, Sep. 2015, 3(9):684-91.
Ashburner et al., "Gene Ontology: tool for the unification of biology. The Gene Ontology Consortium," Nat Genet, May 2000, 25(1):25-29.
Block et al., "Chapter 27 Immobilized-Metal Affinity Chromatography (IMAC): A Review," Methods in Enzymology, 2009, 463:439-473.
Boon et al., "MCIDAS mutations result in a mucociliary clearance disorder with reduced generation of multiple motile cilia," Nat Comms, Jul. 2014, 5:4418, 9 pages.
Bottier et al., "How Does Cilium Length Affect Beating?," Biophysical Journal, Apr. 2019, 116:1292-1304.
Broekhuis et al., "Regulation of Cilium Length and Intraflagellar Transport by the RCK-Kinases ICK and MOK in Renal Epithelial Cells," PLoS ONE, Sep. 2014, 9(9):e108470, 9 pages.
Carrera et al., "The conserved lysine of the catalytic domain of protein kinases is actively involved in the phosphotransfer reaction and not required for anchoring ATP," PNAS, Jan. 1993, 90(2):442-446.
Chivukula et al., "A human ciliopathy reveals essential functions for NEK10 in airway mucociliary clearance," Nature Medicine, Feb. 2020, 26(2):244-251, 18 pages.
Chivukula et al., "Abstract: NEK10 Loss of Function Causes a Novel Human Motile Ciliopathy," American Journal of Respiratory and Critical Care Medicine, May 2019, 199, Abstract No. A4278, 3 pages.
De Wildt et al., "Characterization of human variable domain antibody fragments against the U1 RNA-associated A protein, selected from a synthetic and a patient-derived combinatorial V gene library," Eur J Immunol., Apr. 1996, 26(3):629-39.
Eng et al., "An approach to correlate tandem mass spectral data of peptides with amino acid sequences in a protein database," J Am Soc Mass Spectrom, Nov. 1994, 5(11):976-989.
Fulcher et al., "Well-differentiated human airway epithelial cell cultures," Methods Mol Med., in Human Cell Culture Protocols, 2005, 107:183-206.
GenBank Accession No. MK806425, "*Homo sapiens* genotype wildtype NEK10 mRNA, complete cds," dated Dec. 8, 2019, 2 pages.
GenBank Accession No. MK806426, "*Homo sapiens* genotype NEK10c1230+5G>C NEK10 mRNA, complete cds," dated Dec. 8, 2019, 2 pages.

(Continued)

*Primary Examiner* — Michelle F. Paguio Frising
(74) *Attorney, Agent, or Firm* — Fish & Richardson P.C.

(57) ABSTRACT

Aspects of the present disclosure provide compositions comprising NEK10 for example, wild-type NEK10 or a hyperactive NEK10 mutant such as NEK10$^{S684D}$, and methods of using such for treating a respiratory disorder such as bronchiectasis.

16 Claims, 77 Drawing Sheets
Specification includes a Sequence Listing.

(56) References Cited

OTHER PUBLICATIONS

Guggino and Cebotara, "Adeno-Associated Virus (AAV) gene therapy for cystic fibrosis: current barriers and recent developments," Expert Opin Biol Ther, Oct. 2017, 17(10):1265-73, 17 pages.

Haider, "Characterization of NEK10 Tyrosine Kinase Activity in the Cellular Response to DNA Damage," Thesis for the degree of Doctor of Philosophy, University of Toronto, Department of Medical Biophysics, Nov. 2018, 8 pages.

He et al., "NEK7 is an essential mediator of NLRP3 activation downstream of potassium efflux," Nature, Feb. 2016, 530(7590):354-357, 25 pages.

Hoffmann and Lindner, "easyLINKAGE-Plus-automated linkage analyses using large-scale SNP data," Bioinformatics, Sep. 2005, 21(17):3565-3567.

International Preliminary Report on Patentability in International Appln. No. PCT/US2021/013942, mailed on Jul. 28, 2022, 9 pages.

International Search Report and Written Opinion in International Appln. No. PCT/US2021/013942, mailed on Jun. 21, 2021, 13 pages.

Ishikawa and Marshall, "Ciliogenesis: building the cell's antenna," Nat Rev Mal Cell Biol, Apr. 2011, 12(4):222-234.

Karczewski et al., "Variation across 141,456 human exomes and genomes reveals the spectrum of loss-of-function intolerance across human protein-coding genes," bioRxiv, Aug. 2019, 49:531210, 31 pages.

Knowles et al., "Primary Ciliary Dyskinesia," Clinics in Chest Medicine, Sep. 2016, 37(3):449-461, 21 pages.

Knowles et al., "Primary Ciliary Dyskinesia. Recent Advances in Diagnostics, Genetics, and Characterization of Clinical Disease," Am. J. Respir. Crit. Care Med, Oct. 2013, 188(8):913-922.

Lai et al., "Functional characterization of putative cilia genes by high-content analysis," Molecular Biology of the Cell, Apr. 2011, 22(7):1104-1119.

Leopold et al., "Smoking is Associated with Shortened Airway Cilia," PLoS ONE, Dec. 2009, 4(12):e8157, 11 pages.

Liu et al., "Imaging the subcellular structure of human coronary atherosclerosis using micro-optical coherence tomography," Nat. Med, Jul. 2011, 17(8):1010-1014.

Liu et al., "Method for Quantitative Study of Airway Functional Microanatomy Using Micro-Optical Coherence Tomography," PLoS ONE, Jan. 2013, 8(1):e54473, 8 pages.

Marquez Loza et al., "Lentiviral Vectors for the Treatment and Prevention of Cystic Fibrosis Lung Disease," Genes (Basel), Mar. 2019, 10(3):218, 17 pages.

Moniz and Stambolic, "Nek10 mediates G2/M cell cycle arrest and MEK autoactivation in response to UV irradiation," Mol Cell Biol, Jan. 2011, 31(1):30-42.

Moniz et al., "Nek family of kinases in cell cycle, checkpoint control and cancer," Cell Division, 2011, 6:18, 10 pages.

Moniz, "Characterization of NimA-related Kinase 10 (NEK10): A Role in Checkpoint Control," These for the degree of Doctor of Philosophy, University of Toronto, Graduate Department of Medical Biophysics, 2010, 177 pages.

Neuberger et al., "Use of primary cultures of human bronchial epithelial cells isolated from cystic fibrosis patients for the preclinical testing of CFTR modulators," Methods Mol Biol., 2011, 741:39-54.

Niwa et al., "KIF19A is a Microtubule-Depolymerizing Kinesin for Ciliary Length Control," Dev. Cell, Dec. 2012, 23(6):1167-1175.

Oltean et al., "Quantifying Ciliary Dynamics during Assembly Reveals Stepwise Waveform Maturation in Airway Cells," Am. J. Respir. Cell Mol. Biol, Oct. 2018, 59(4):511-522.

Osinka et al., "Ciliary Proteins: Filling the Gaps. Recent Advances in Deciphering the Protein Composition of Motile Ciliary Complexes," Cells, Jul. 2019, 8(7):730, 22 pages.

Ostrowski et al., "A Proteomic Analysis of Human Cilia Identification of Novel Components," Mal Cell Proteomics, Jun. 2002, 1(6):451-465.

Ostrowski et al., "Targeting expression of a transgene to the airway surface epithelium using a ciliated cell-specific promoter," Mol. Ther, Oct. 2003, 8(4):637-645.

Perez-Riverol et al., The PRIDE database and related tools and resources in 2019: improving support for quantification data, Nucleic Acids Res, 2019, 47:D442-D450.

Piao et al., "A microtubule depolymerizing kinesin functions during both flagellar disassembly and flagellar assembly in Chlamydomonas," Proc. Natl. Acad Sci. USA, Mar. 2009, 106(12):4713-4718.

Porpora et al., "Counterregulation of cAMP-directed kinase activities controls ciliogenesis," Nat Comms, Mar. 2018, 9(1):1224, 13 pages.

Richards et al., "An Autoinhibitory Tyrosine Motif in the Cell-Cycle-Regulated Nek7 Kinase is Released through Binding of Nek9," Mol. Cell, Nov. 2009, 36(4):560-570.

Ruan et al., "Efficient Gene Editing at Major CFTR Mutation Loci," Mol Ther Nucleic Acids, Jun. 2019, 16:73-81.

Sbalzarini and Koumoutsakos, "Feature point tracking and trajectory analysis for video imaging in cell biology," J Struct. Biol, Aug. 2005, 151(2):182-195.

Schindelin et al., "Fiji: an open-source platform for biological-image analysis," Nat. Methods, Jun. 2012, 9(7):676-682.

Smith et al., "Development of polycystic kidney disease in juvenile cystic kidney mice: insights into pathogenesis, ciliary abnormalities, and common features with human disease," J Am. Soc. Nephrol, Oct. 2006, 17:2821-2831.

Tammana et al., "Centrosomal protein CEP104 (Chlamydomonas FAP256) moves to the ciliary tip during ciliary assembly," J Cell Sci, Nov. 2013, 126:5018-5029.

Teves et al., "Mammalian axoneme central pair complex proteins: Broader roles revealed by gene knockout phenotypes," Cytoskeleton, Jan. 2016, 73(1):3-22.

The Gene Ontology Consortium, "The Gene Ontology Resource: 20 years and still Going strong," Nucleic Acids Res, Jan. 2019, 47(DI):D330-D338.

Thiel et al., "NEK1 Mutations Cause Short-Rib Polydactyly Syndrome Type Majewski," The American Journal of Human Genetics, Jan. 2011, 88(1):106-114.

UniProt Accession No. Q6ZWH5, "Serine/threonine-protein kinase Nek10," Mar. 21, 2012, 4 pages.

Vasudevan et al., "Kinesin-13 regulates the quantity and quality of tubulin inside cilia," Molecular Biology of the Cell, Feb. 2015, 26(3):478-494.

Vladar et al., "Airway epithelial homeostasis and planar cell polarity signaling depend on multiciliated cell differentiation," JCI Insight, Aug. 2016, 1(13):e88027, 18 pages.

Wallmeier et al., "Mutations in CCNO result in congenital mucociliary clearance disorder with reduced generation of multiple motile cilia," Nat Genet, Jun. 2014, 46(6):646-651, 8 pages.

Wang et al., "Flagellar regeneration requires cytoplasmic microtubule depolymerization and kinesin-13," Journal of Cell Science, Mar. 2013, 126(Pt 6):1531-1540.

Wang et al., "Identification and characterization of essential genes in the human genome," Science, Nov. 2015, 350(6264):1096-1101.

Zhao et al., "Proteome of the central apparatus of a ciliary axoneme," J Cell Biol, Jun. 2019, 218(6):2051-2070.

* cited by examiner proband chest computed tomography

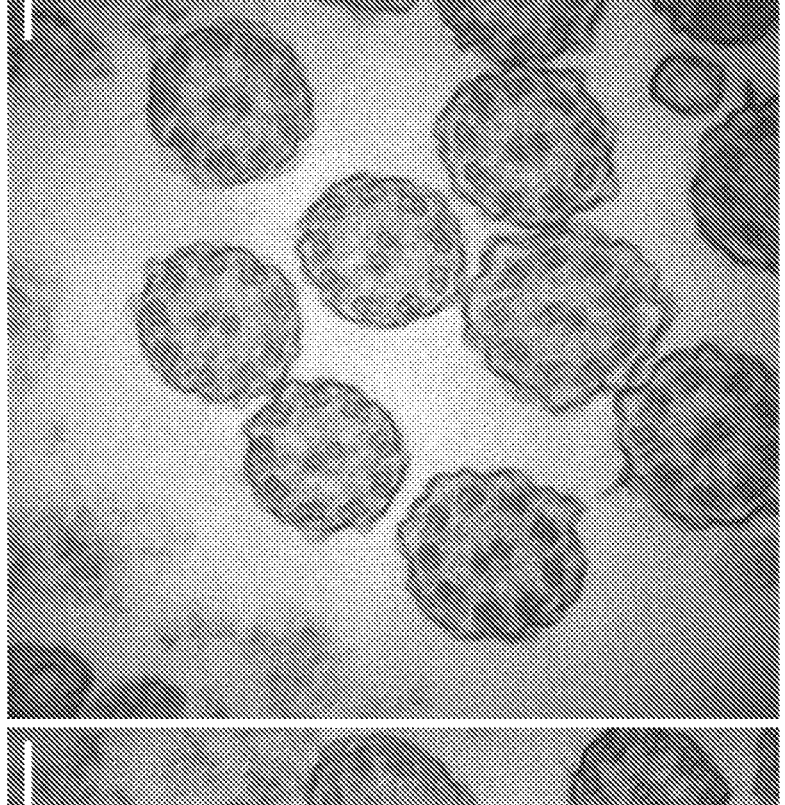
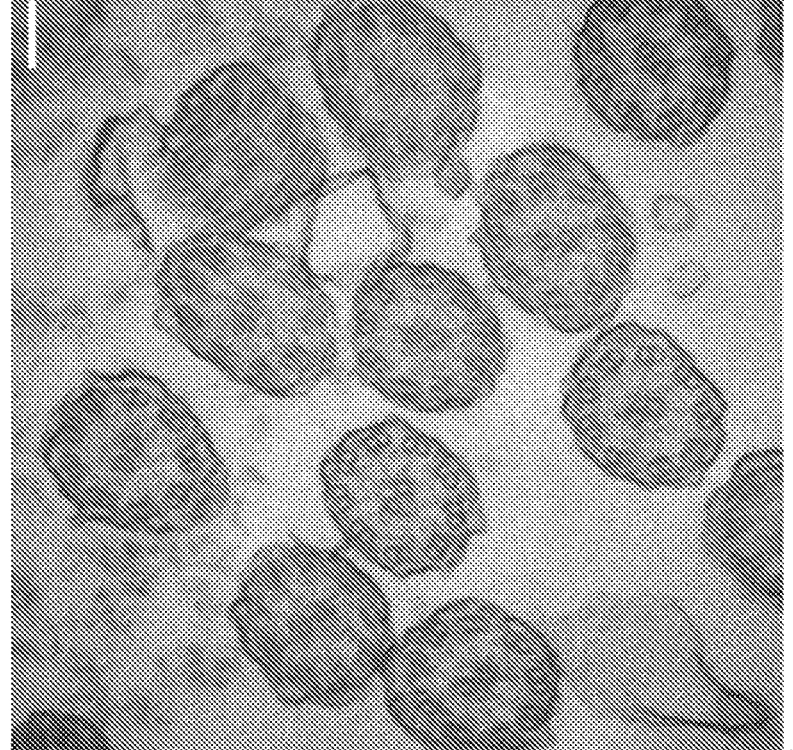
proband nasal biopsy electron micrograph
FIG. 1B

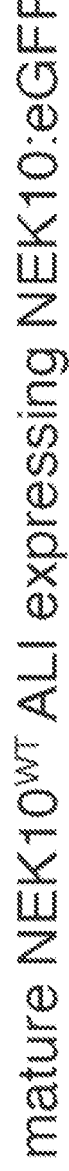
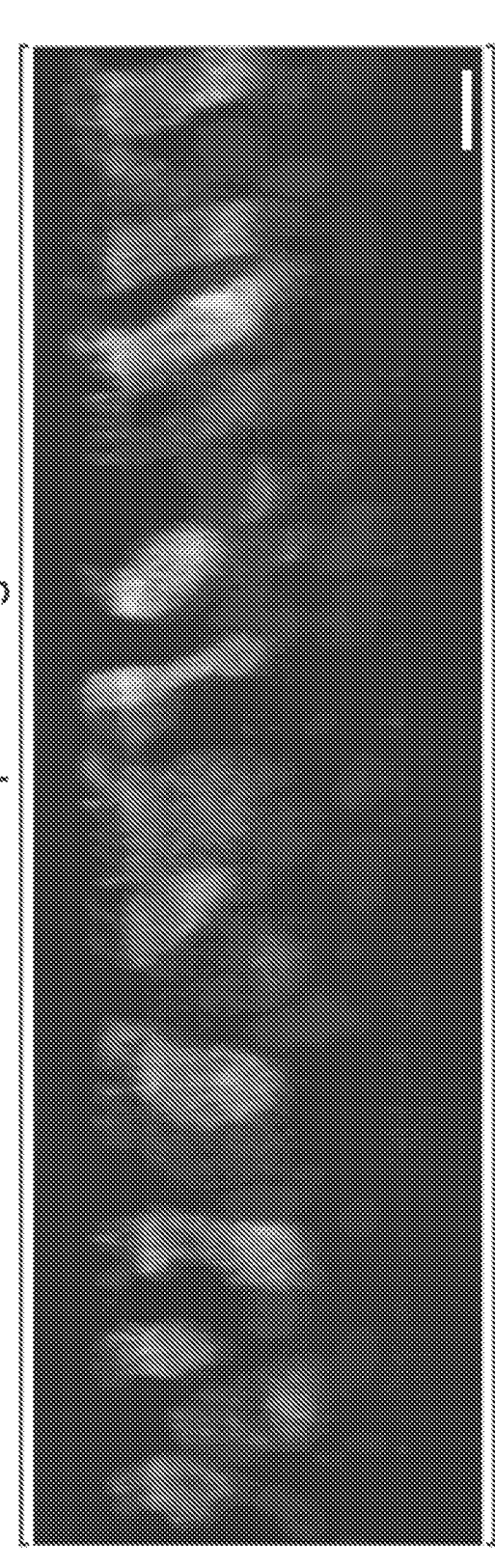
mature NEK10<sup>WT</sup> ALI expressing NEK10:eGFP
DAPI / native eGFP / Ac-α- tubulin
FIG. 2B $$\Delta area = area_{cell} - area_{GFP}$$
$$\Delta axis = axis_{cell} - axis_{GFP}$$

NEK10$^{WT}$
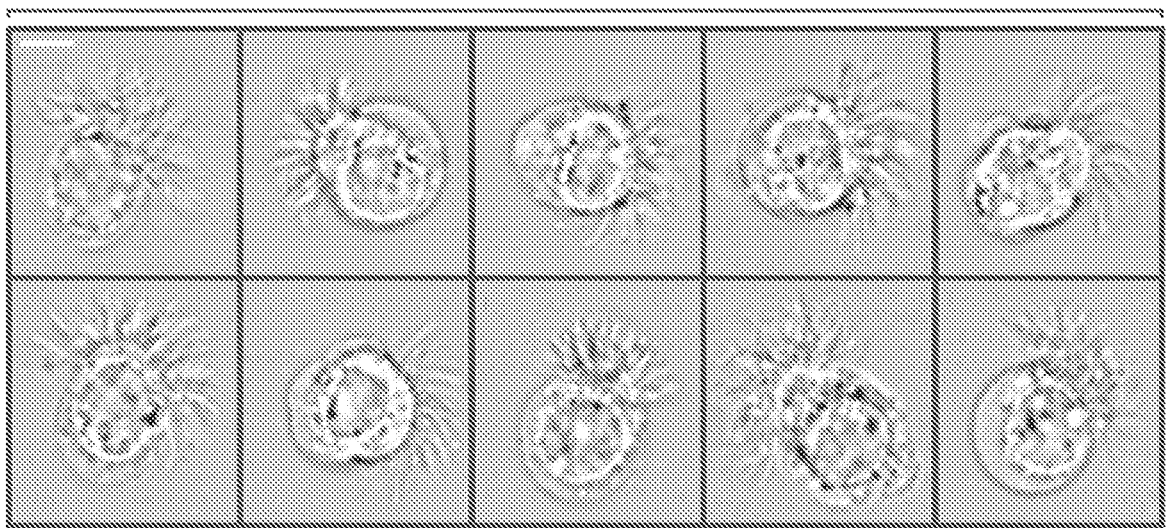
NEK10$^{G>C}$
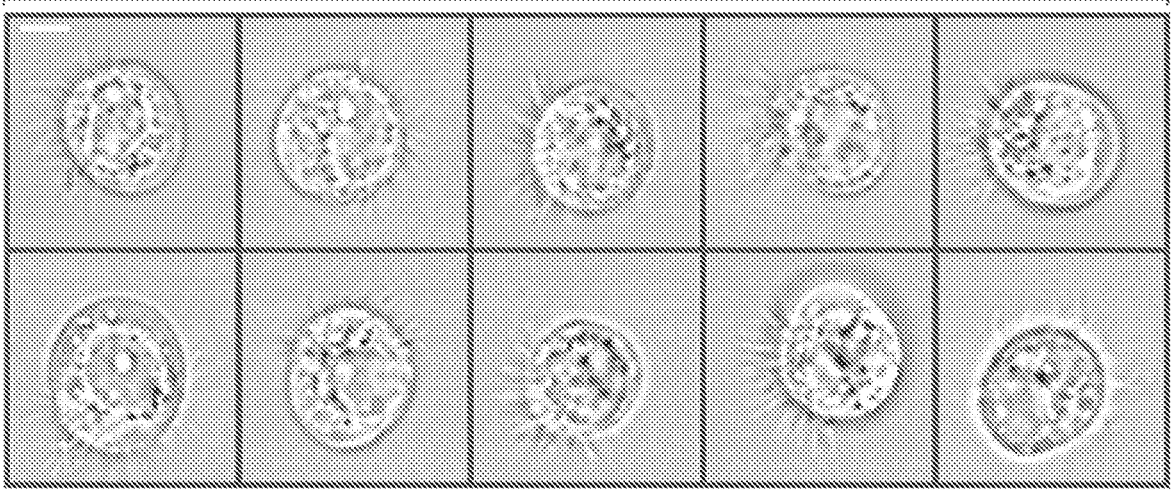
FIG. 3D

| gene class | phosphopeptides depleted upon NEK 10 deletion (by gene) |
|---|---|
| PCD loci | ARMC4, CCDC114, CCDC151, CCDC39, CCDC40, CCDC65, DNAAF1, DNAAF2, DNAH1, DNAH5, DNAI1, DNAI2, DRC1, GAS2L2, GAS8 HYDIN, LRRC56, OFD1, RPGR, RSPH3, RSPH4A, SPAG1, TTC25 |
| axonemal dyneins, assembly factors | DNAAF1, DNAAF2, DNAH1, DNAH12, DNAH5, DNAH6, DNAH7, DNAI1, DNAJB6, DNALI1 |
| kinesins | KIF13B, KIF19, KIF5B, KIF6, KIF9 |
| intraflagellar transport | BBS4, IFT140, IFT43, IFT46, IFT74M, IFT88 |
| radio spoke | RSPH1, RSPH10B, RSPH3, RSPH4A |
| central pair complex | CCDC180, CFAP221, CFAP47, CFAP54, CFAP70, HYDIN, MYCBPAP, SPAG16, SPAG17, SPAG6, SPEF1, SPEF2 |
| ciliary length control | CEP104, IFT46, KIF13B, KIF19, MAK |

FIG. 4F sibling b sibling a

GGAAAAACAT-CACCATTTT

GGAAAAACATTCACCATTTT c.1869dupT

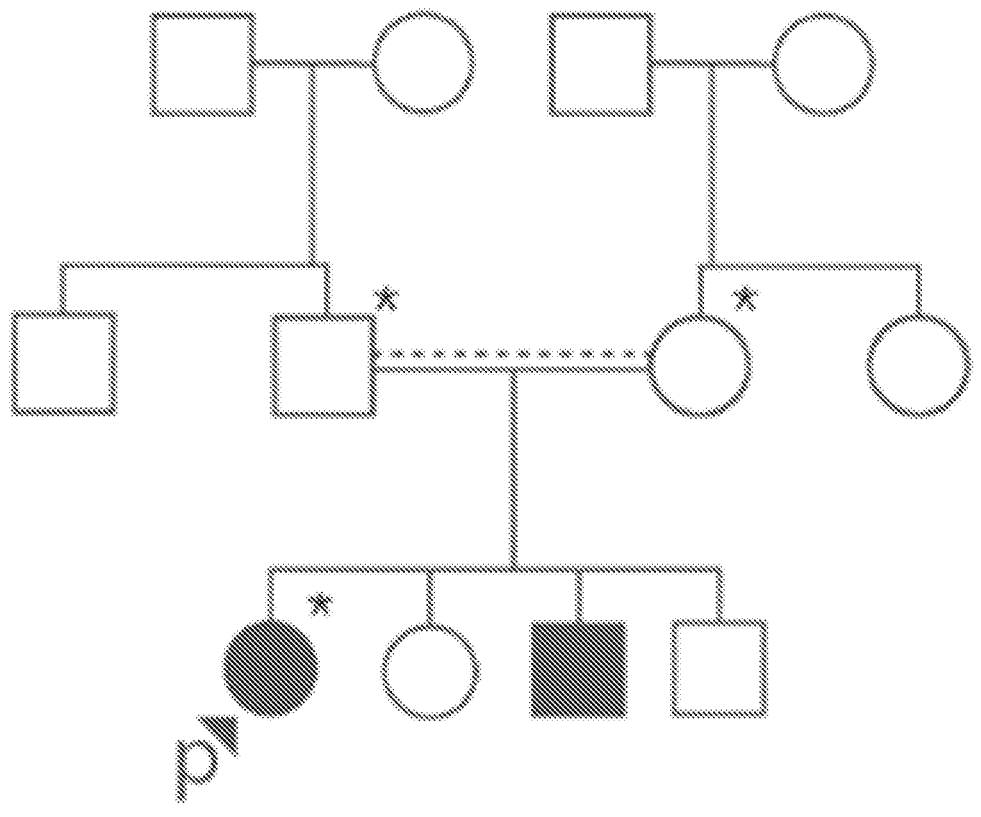
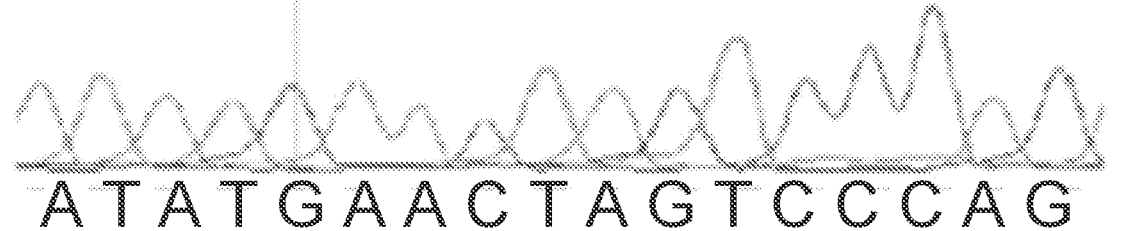
ATATGAACCAGTCCCAG
ATATGAACTAGTCCCAG
c.2243C>T
FIG. 5G

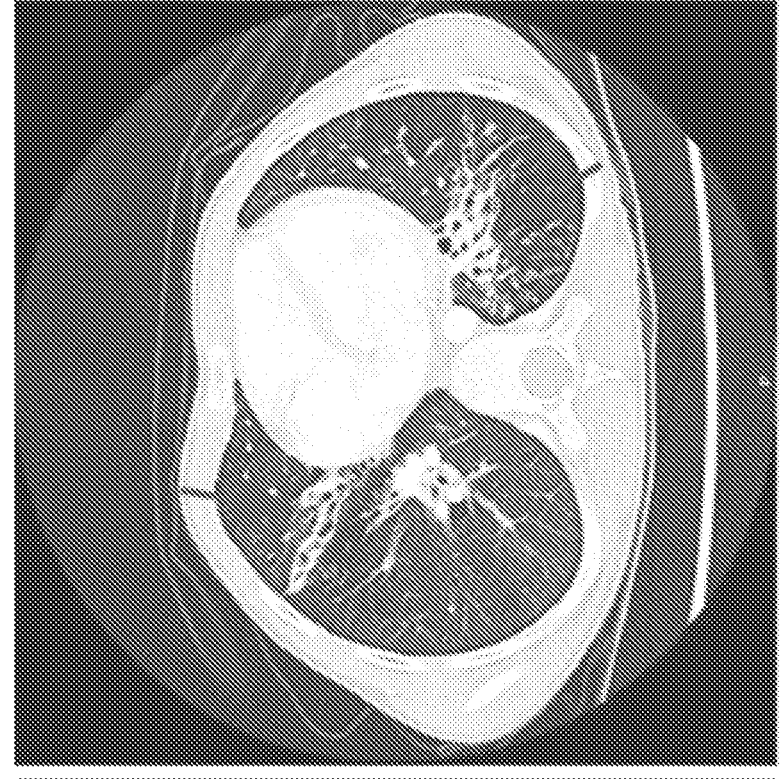
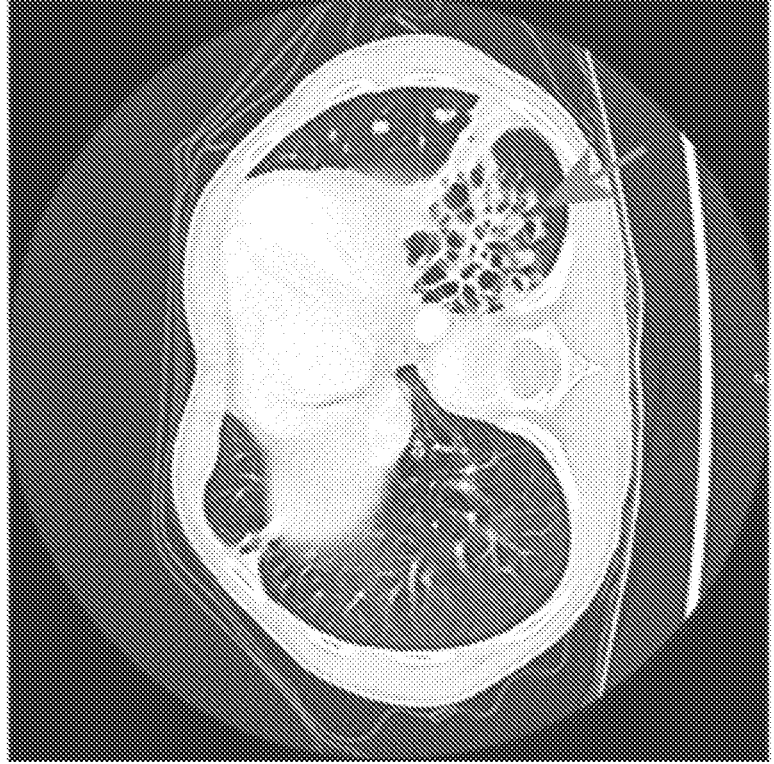
FIG. 5H

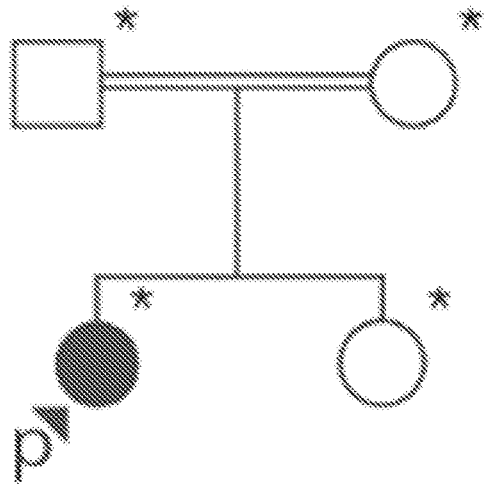
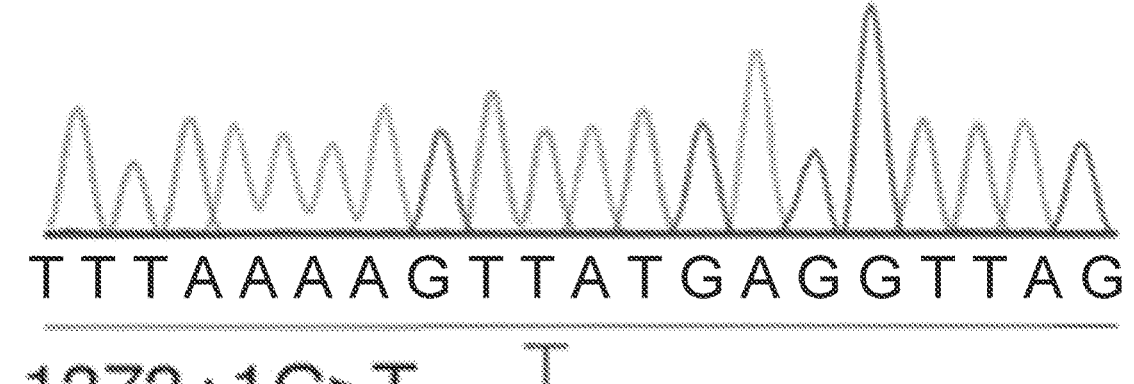
TTTAAAAGTGATGAGGTTAG
TTTAAAAGTTATGAGGTTAG
c.1373+1G>T
FIG. 5I

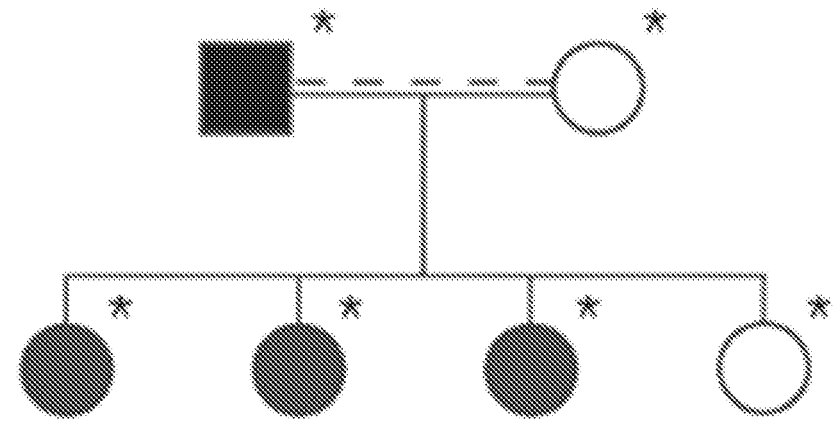
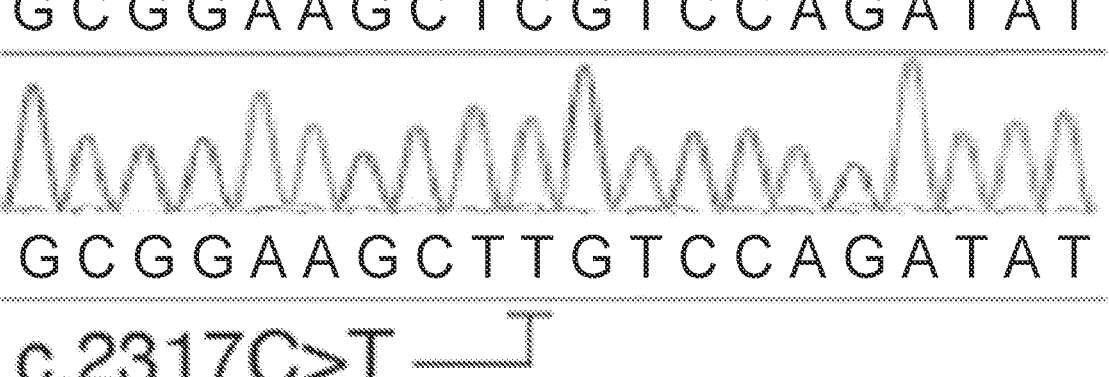
GCGGAAGCTCGTCCAGATAT
GCGGAAGCTTGTCCAGATAT
c.2317C>T
FIG. 5L

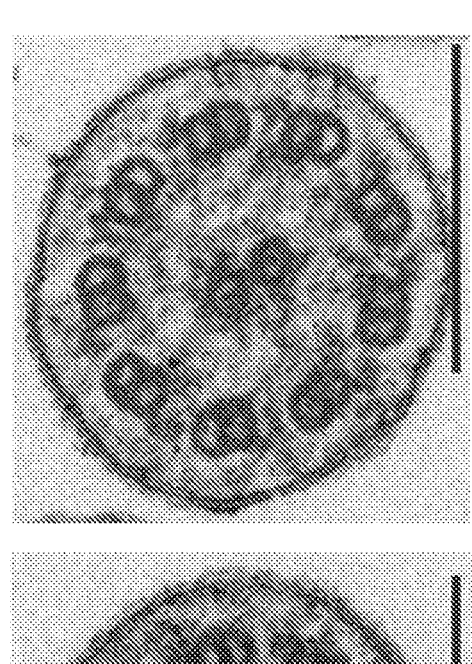
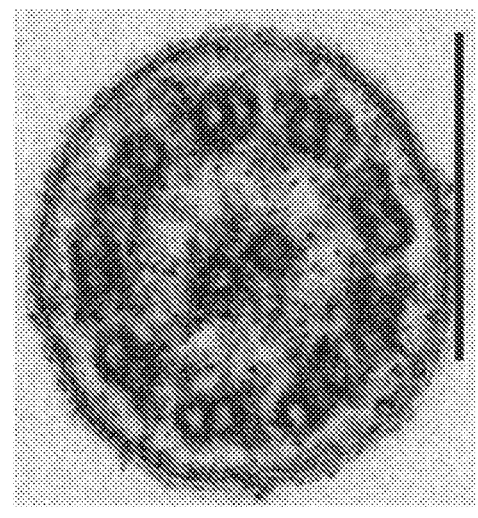
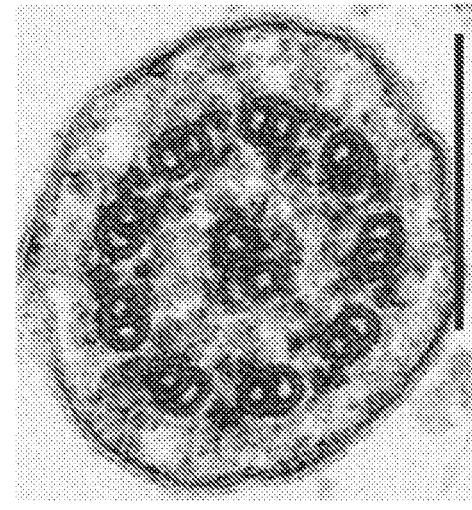
FIG. 50

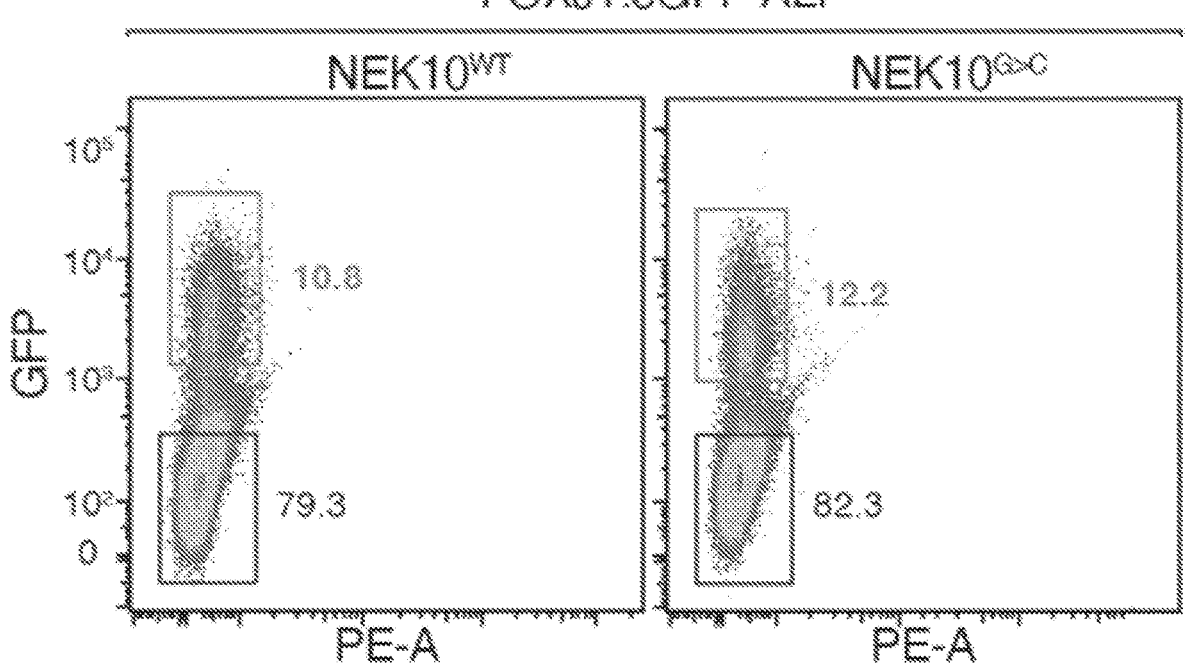
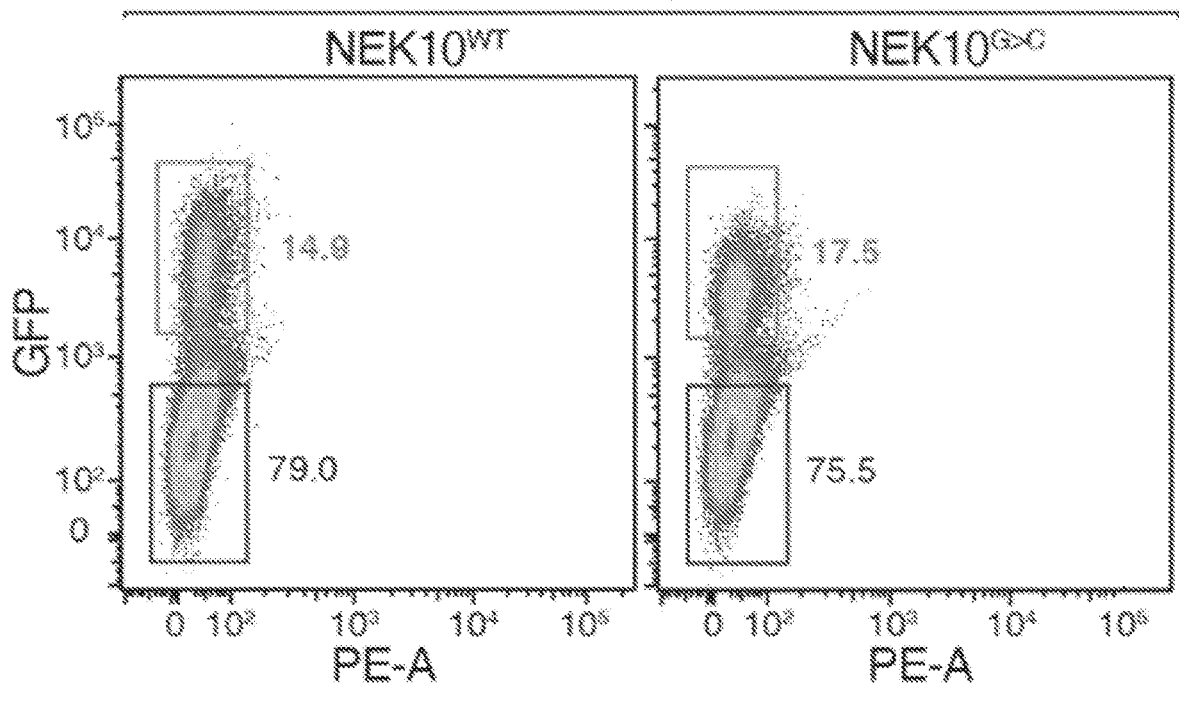
FIG. 6I

FIG. 7D

| GO biological process | fold enrichment | p-value | FDR |
|---|---|---|---|
| cilium movement involved in cell motility (GO:0060294) | 9.40 | 1.36E-04 | 3.82E-02 |
| axoneme assembly (GO:0035082) | 5.49 | 2.13E-08 | 4.56E-05 |
| microtubule bundle formation (GO:0035082) | 4.70 | 2.55E-09 | 1.37E-05 |
| cilium movement (GO:0003341) | 4.70 | 2.49E-06 | 1.90E-03 |
| cilium-dependent cell motility (GO:0060285) | 4.41 | 1.79E-05 | 1.13E-02 |
| cilium or flagellum-dependent cell motility (GO:0001539) | 4.41 | 1.79E-05 | 1.06E-02 |
| microtubule-based movement (GO:0007018) | 2.75 | 5.99E-07 | 4.93E-04 |
| cilium organization (GO:0044782) | 2.46 | 1.79E-07 | 2.13E-04 |
| microtubule cytoskeleton organization (GO:0000226) | 2.37 | 5.10E-08 | 7.80E-05 |
| cilium assembly (GO:0060271) | 2.32 | 3.33E-06 | 2.38E-03 |
| microtubule-based process (GO:0007017) | 2.26 | 2.33E-09 | 2.49E-05 |
| plasma membrane bounded cell projection assembly (GO:0120031) | 1.93 | 1.12E-04 | 3.43E-02 |
| organelle assembly (GO:0070925) | 1.92 | 1.10E-05 | 7.34E-03 |
| cell projection assembly (GO:0030031) | 1.92 | 1.24E-04 | 3.70E-02 |
| unclassified (UNCLASSIFIED) | 1.81 | 2.80E-05 | 1.36E-02 |
| cytoskeleton organization (GO:0007010) | 1.65 | 1.87E-05 | 1.06E-02 |

FIG. 9D

SEQUENCE LISTING

<160> NUMBER OF SEQ ID NOS: 31

<210> SEQ ID NO 1
<211> LENGTH: 1172
<212> TYPE: PRT
<213> ORGANISM: Homo sapiens

<400> SEQUENCE: 1

```
Met Pro Asp Gln Asp Lys Lys Val Lys Thr Thr Glu Lys Ser Thr Asp
1               5                   10                  15

Lys Gln Gln Glu Ile Thr Ile Arg Asp Tyr Ser Asp Leu Lys Arg Leu
            20                  25                  30

Arg Cys Leu Leu Asn Val Gln Ser Ser Lys Gln Gln Leu Pro Ala Ile
        35                  40                  45

Asn Phe Asp Ser Ala Gln Asn Ser Met Thr Lys Ser Glu Pro Ala Ile
    50                  55                  60

Arg Ala Gly Gly His Arg Ala Arg Gly Gln Trp His Glu Ser Thr Glu
65                  70                  75                  80

Ala Val Glu Leu Glu Asn Phe Ser Ile Asn Tyr Lys Asn Glu Arg Asn
                85                  90                  95

Phe Ser Lys His Pro Gln Arg Lys Leu Phe Gln Glu Ile Phe Thr Ala
            100                 105                 110

Leu Val Lys Asn Arg Leu Ile Ser Arg Glu Trp Val Asn Arg Ala Pro
        115                 120                 125

Ser Ile His Phe Leu Arg Val Leu Ile Cys Leu Arg Leu Leu Met Arg
        130                 135                 140

Asp Pro Cys Tyr Gln Glu Ile Leu His Ser Leu Gly Gly Ile Glu Asn
145                 150                 155                 160

Leu Ala Gln Tyr Met Glu Ile Val Ala Asn Glu Tyr Leu Gly Tyr Gly
                165                 170                 175
```

-continued

```
Glu Glu Gln His Thr Val Asp Lys Leu Val Asn Met Thr Tyr Ile Phe
        180             185             190

Gln Lys Leu Ala Ala Val Lys Asp Gln Arg Glu Trp Val Thr Thr Ser
        195             200             205

Gly Ala His Lys Thr Leu Val Asn Leu Leu Gly Ala Arg Asp Thr Asn
        210             215         220

Val Leu Leu Gly Ser Leu Leu Ala Leu Ala Ser Leu Ala Glu Ser Gln
225             230             235             240

Glu Cys Arg Glu Lys Ile Ser Glu Leu Asn Ile Val Glu Asn Leu Leu
            245             250             255

Met Ile Leu His Glu Tyr Asp Leu Leu Ser Lys Arg Leu Thr Ala Glu
            260             265             270

Leu Leu Arg Leu Leu Cys Ala Glu Pro Gln Val Lys Glu Gln Val Lys
            275             280             285

Leu Tyr Glu Gly Ile Pro Val Leu Leu Ser Leu Leu His Ser Asp His
        290             295             300

Leu Lys Leu Leu Trp Ser Ile Val Trp Ile Leu Val Gln Val Cys Glu
305             310             315             320

Asp Pro Glu Thr Ser Val Glu Ile Arg Ile Trp Gly Gly Ile Lys Gln
            325             330             335

Leu Leu His Ile Leu Gln Gly Asp Arg Asn Phe Val Ser Asp His Ser
            340             345             350

Ser Ile Gly Ser Leu Ser Ser Ala Asn Ala Ala Gly Arg Ile Gln Gln
            355             360             365

Leu His Leu Ser Glu Asp Leu Ser Pro Arg Glu Ile Gln Glu Asn Thr
        370             375             380

Phe Ser Leu Gln Ala Ala Cys Cys Ala Ala Leu Thr Glu Leu Val Leu
385             390             395             400

Asn Asp Thr Asn Ala His Gln Val Val Gln Glu Asn Gly Val Tyr Thr
            405             410             415

Ile Ala Lys Leu Ile Leu Pro Asn Lys Gln Lys Asn Ala Ala Lys Ser
            420             425             430

Asn Leu Leu Gln Cys Tyr Ala Phe Arg Ala Leu Arg Phe Leu Phe Ser
            435             440             445

Met Glu Arg Asn Arg Pro Leu Phe Lys Arg Leu Phe Pro Thr Asp Leu
        450             455             460

Phe Glu Ile Phe Ile Asp Ile Gly His Tyr Val Arg Asp Ile Ser Ala
465             470             475             480

Tyr Glu Glu Leu Val Ser Lys Leu Asn Leu Leu Val Glu Asp Glu Leu
            485             490             495

Lys Gln Ile Ala Glu Asn Ile Glu Ser Ile Asn Gln Asn Lys Ala Pro
            500             505             510

Leu Lys Tyr Ile Gly Asn Tyr Ala Ile Leu Asp His Leu Gly Ser Gly
            515             520             525

Ala Phe Gly Cys Val Tyr Lys Val Arg Lys His Ser Gly Gln Asn Leu
        530             535             540

Leu Ala Met Lys Glu Val Asn Leu His Asn Pro Ala Phe Gly Lys Asp
545             550             555             560

Lys Lys Asp Arg Asp Ser Ser Val Arg Asn Ile Val Ser Glu Leu Thr
            565             570             575

Ile Ile Lys Glu Gln Leu Tyr His Pro Asn Ile Val Arg Tyr Tyr Lys
            580             585             590
```

-continued

```
Thr Phe Leu Glu Asn Asp Arg Leu Tyr Ile Val Met Glu Leu Ile Glu
        595                 600                 605

Gly Ala Pro Leu Gly Glu His Phe Ser Ser Leu Lys Glu Lys His His
        610                 615                 620

His Phe Thr Glu Glu Arg Leu Trp Lys Ile Phe Ile Gln Leu Cys Leu
625                 630                 635                 640

Ala Leu Arg Tyr Leu His Lys Glu Lys Arg Ile Val His Arg Asp Leu
                645                 650                 655

Thr Pro Asn Asn Ile Met Leu Gly Asp Lys Asp Lys Val Thr Val Thr
                660                 665                 670

Asp Phe Gly Leu Ala Lys Gln Lys Gln Glu Asn Ser Lys Leu Thr Ser
                675                 680                 685

Val Val Gly Thr Ile Leu Tyr Ser Cys Pro Glu Val Leu Lys Ser Glu
        690                 695                 700

Pro Tyr Gly Glu Lys Ala Asp Val Trp Ala Val Gly Cys Ile Leu Tyr
705                 710                 715                 720

Gln Met Ala Thr Leu Ser Pro Pro Phe Tyr Ser Thr Asn Met Leu Ser
                725                 730                 735

Leu Ala Thr Lys Ile Val Glu Ala Val Tyr Glu Pro Val Pro Glu Gly
                740                 745                 750

Ile Tyr Ser Glu Lys Val Thr Asp Thr Ile Ser Arg Cys Leu Thr Pro
                755                 760                 765

Asp Ala Glu Ala Arg Pro Asp Ile Val Glu Val Ser Ser Met Ile Ser
        770                 775                 780

Asp Val Met Met Lys Tyr Leu Asp Asn Leu Ser Thr Ser Gln Leu Ser
785                 790                 795                 800

Leu Glu Lys Lys Leu Glu Arg Glu Arg Arg Arg Thr Gln Arg Tyr Phe
                805                 810                 815

Met Glu Ala Asn Arg Asn Thr Val Thr Cys His His Glu Leu Ala Val
                820                 825                 830

Leu Ser His Glu Thr Phe Glu Lys Ala Ser Leu Ser Ser Ser Ser Ser
        835                 840                 845

Gly Ala Ala Ser Leu Lys Ser Glu Leu Ser Glu Ser Ala Asp Leu Pro
        850                 855                 860

Pro Glu Gly Phe Gln Ala Ser Tyr Gly Lys Asp Glu Asp Arg Ala Cys
865                 870                 875                 880

Asp Glu Ile Leu Ser Asp Asp Asn Phe Asn Leu Glu Asn Ala Glu Lys
                885                 890                 895

Asp Thr Tyr Ser Glu Val Asp Asp Glu Leu Asp Ile Ser Asp Asn Ser
                900                 905                 910

Ser Ser Ser Ser Ser Ser Pro Leu Lys Glu Ser Thr Phe Asn Ile Leu
        915                 920                 925

Lys Arg Ser Phe Ser Ala Ser Gly Gly Glu Arg Gln Ser Gln Thr Arg
        930                 935                 940

Asp Phe Thr Gly Gly Thr Gly Ser Arg Pro Arg Pro Ala Leu Leu Pro
945                 950                 955                 960

Leu Asp Leu Leu Leu Lys Val Pro Pro His Met Leu Arg Ala His Ile
                965                 970                 975

Lys Glu Ile Glu Ala Glu Leu Val Thr Gly Trp Gln Ser His Ser Leu
                980                 985                 990

Pro Ala Val Ile Leu Arg Asn Leu  Lys Asp His Gly Pro  Gln Met Gly
        995                 1000                1005

Thr Phe  Leu Trp Gln Ala Ser  Ala Gly Ile Ala Val  Ser Gln Arg
```

-continued

```
         1010                1015                1020

Lys Val Arg Gln Ile Ser Asp  Pro Ile Gln Gln Ile  Leu Ile Gln
    1025                1030                1035

Leu His Lys Ile Ile Tyr Ile  Thr Gln Leu Pro Pro  Ala Leu His
    1040                1045                1050

His Asn Leu Lys Arg Arg Val  Ile Glu Arg Phe Lys  Lys Ser Leu
    1055                1060                1065

Phe Ser Gln Gln Ser Asn Pro  Cys Asn Leu Lys Ser  Glu Ile Lys
    1070                1075                1080

Lys Leu Ser Gln Gly Ser Pro  Glu Pro Ile Glu Pro  Asn Phe Phe
    1085                1090                1095

Thr Ala Asp Tyr His Leu Leu  His Arg Ser Ser Gly  Gly Asn Ser
    1100                1105                1110

Leu Ser Pro Asn Asp Pro Thr  Gly Leu Pro Thr Ser  Ile Glu Leu
    1115                1120                1125

Glu Glu Gly Ile Thr Tyr Glu  Gln Met Gln Thr Val  Ile Glu Glu
    1130                1135                1140

Val Leu Glu Glu Ser Gly Tyr  Tyr Asn Phe Thr Ser  Asn Arg Tyr
    1145                1150                1155

His Ser Tyr Pro Trp Gly Thr  Lys Asn His Pro Thr  Lys Arg
    1160                1165                1170
```

<210> SEQ ID NO 2
<211> LENGTH: 19
<212> TYPE: DNA
<213> ORGANISM: Artificial
<220> FEATURE:
<223> OTHER INFORMATION: Synthetic primer

<400> SEQUENCE: 2
agcctgtcca gtgcaaatg                                              19

<210> SEQ ID NO 3
<211> LENGTH: 19
<212> TYPE: DNA
<213> ORGANISM: Artificial
<220> FEATURE:
<223> OTHER INFORMATION: Synthetic primer

<400> SEQUENCE: 3
ggcattggtg tcattgagc                                              19

<210> SEQ ID NO 4
<211> LENGTH: 20
<212> TYPE: DNA
<213> ORGANISM: Artificial
<220> FEATURE:
<223> OTHER INFORMATION: Synthetic primer

<400> SEQUENCE: 4
gcatgaatcc acagaagctg                                             20

<210> SEQ ID NO 5
<211> LENGTH: 20
<212> TYPE: DNA
<213> ORGANISM: Artificial
<220> FEATURE:
<223> OTHER INFORMATION: Synthetic primer

<400> SEQUENCE: 5
tacgctgagg atgtttgctg                                             20

```
<210> SEQ ID NO 6
<211> LENGTH: 20
<212> TYPE: DNA
<213> ORGANISM: Artificial
<220> FEATURE:
<223> OTHER INFORMATION: Synthetic primer

<400> SEQUENCE: 6
gagcccaact ttttcacagc                                          20

<210> SEQ ID NO 7
<211> LENGTH: 19
<212> TYPE: DNA
<213> ORGANISM: Artificial
<220> FEATURE:
<223> OTHER INFORMATION: Synthetic primer

<400> SEQUENCE: 7
ccaattcaat gctggttgg                                           19

<210> SEQ ID NO 8
<211> LENGTH: 21
<212> TYPE: DNA
<213> ORGANISM: Artificial
<220> FEATURE:
<223> OTHER INFORMATION: Synthetic primer

<400> SEQUENCE: 8
tcagtggaga aggagttgga c                                        21

<210> SEQ ID NO 9
<211> LENGTH: 22
<212> TYPE: DNA
<213> ORGANISM: Artificial
<220> FEATURE:
<223> OTHER INFORMATION: Synthetic primer

<400> SEQUENCE: 9
ctgccatatc cagaggaaac ac                                       22

<210> SEQ ID NO 10
<211> LENGTH: 19
<212> TYPE: DNA
<213> ORGANISM: Artificial
<220> FEATURE:
<223> OTHER INFORMATION: Synthetic primer

<400> SEQUENCE: 10
ccaaaagccc agagaaagc                                           19

<210> SEQ ID NO 11
<211> LENGTH: 20
<212> TYPE: DNA
<213> ORGANISM: Artificial
<220> FEATURE:
<223> OTHER INFORMATION: Synthetic primer

<400> SEQUENCE: 11
agttggggat cttcagcttc                                          20

<210> SEQ ID NO 12
<211> LENGTH: 20
<212> TYPE: DNA
<213> ORGANISM: Artificial
<220> FEATURE:
```

-continued

```
<223> OTHER INFORMATION: Synthetic primer

<400> SEQUENCE: 12
tggatcacgg acaacttctg                                          20

<210> SEQ ID NO 13
<211> LENGTH: 20
<212> TYPE: DNA
<213> ORGANISM: Artificial
<220> FEATURE:
<223> OTHER INFORMATION: Synthetic primer

<400> SEQUENCE: 13
gaggcacttt gatgaagcac                                          20

<210> SEQ ID NO 14
<211> LENGTH: 22
<212> TYPE: DNA
<213> ORGANISM: Artificial
<220> FEATURE:
<223> OTHER INFORMATION: Synthetic primer

<400> SEQUENCE: 14
gctctttgag ttgatgcctg tc                                       22

<210> SEQ ID NO 15
<211> LENGTH: 20
<212> TYPE: DNA
<213> ORGANISM: Artificial
<220> FEATURE:
<223> OTHER INFORMATION: Synthetic primer

<400> SEQUENCE: 15
cagcggcaat gtagttcaag                                          20

<210> SEQ ID NO 16
<211> LENGTH: 20
<212> TYPE: DNA
<213> ORGANISM: Artificial
<220> FEATURE:
<223> OTHER INFORMATION: Synthetic primer

<400> SEQUENCE: 16
agacaaatcg ctccaccaac                                          20

<210> SEQ ID NO 17
<211> LENGTH: 20
<212> TYPE: DNA
<213> ORGANISM: Artificial
<220> FEATURE:
<223> OTHER INFORMATION: Synthetic primer

<400> SEQUENCE: 17
cctgcggctt aatttgactc                                          20

<210> SEQ ID NO 18
<211> LENGTH: 22
<212> TYPE: DNA
<213> ORGANISM: Artificial
<220> FEATURE:
<223> OTHER INFORMATION: Synthetic primer

<400> SEQUENCE: 18
tctggggcat tgatgtttta ca                                       22
```

-continued

```
<210> SEQ ID NO 19
<211> LENGTH: 20
<212> TYPE: DNA
<213> ORGANISM: Artificial
<220> FEATURE:
<223> OTHER INFORMATION: Synthetic primer

<400> SEQUENCE: 19
ccccatggca tcttggtctt                                              20

<210> SEQ ID NO 20
<211> LENGTH: 20
<212> TYPE: DNA
<213> ORGANISM: Artificial
<220> FEATURE:
<223> OTHER INFORMATION: Synthetic primer

<400> SEQUENCE: 20
gttccccaga acgaacggat                                              20

<210> SEQ ID NO 21
<211> LENGTH: 19
<212> TYPE: DNA
<213> ORGANISM: Artificial
<220> FEATURE:
<223> OTHER INFORMATION: Synthetic primer

<400> SEQUENCE: 21
catgtctgcg gggactctc                                               19

<210> SEQ ID NO 22
<211> LENGTH: 20
<212> TYPE: DNA
<213> ORGANISM: Artificial
<220> FEATURE:
<223> OTHER INFORMATION: Synthetic primer

<400> SEQUENCE: 22
gcccggcaca aaattaagca                                              20

<210> SEQ ID NO 23
<211> LENGTH: 20
<212> TYPE: DNA
<213> ORGANISM: Artificial
<220> FEATURE:
<223> OTHER INFORMATION: Synthetic primer

<400> SEQUENCE: 23
gatgcagagg aagcagcagt                                              20

<210> SEQ ID NO 24
<211> LENGTH: 25
<212> TYPE: DNA
<213> ORGANISM: Artificial
<220> FEATURE:
<223> OTHER INFORMATION: Synthetic primer

<400> SEQUENCE: 24
caccggtctg agcccgccat caggg                                        25

<210> SEQ ID NO 25
<211> LENGTH: 25
<212> TYPE: DNA
<213> ORGANISM: Artificial
<220> FEATURE:
<223> OTHER INFORMATION: Synthetic primer
```

-continued

```
<400> SEQUENCE: 25
aaacccctga tggcgggctc agacc                                      25

<210> SEQ ID NO 26
<211> LENGTH: 25
<212> TYPE: DNA
<213> ORGANISM: Artificial
<220> FEATURE:
<223> OTHER INFORMATION: Synthetic primer

<400> SEQUENCE: 26
caccggcggg tggacacaga gctcg                                      25

<210> SEQ ID NO 27
<211> LENGTH: 25
<212> TYPE: DNA
<213> ORGANISM: Artificial
<220> FEATURE:
<223> OTHER INFORMATION: Synthetic primer

<400> SEQUENCE: 27
aaaccgagct ctgtgtccac ccgcc                                      25

<210> SEQ ID NO 28
<211> LENGTH: 25
<212> TYPE: DNA
<213> ORGANISM: Artificial
<220> FEATURE:
<223> OTHER INFORMATION: Synthetic primer

<400> SEQUENCE: 28
caccggctgc tcttctccat agccg                                      25

<210> SEQ ID NO 29
<211> LENGTH: 25
<212> TYPE: DNA
<213> ORGANISM: Artificial
<220> FEATURE:
<223> OTHER INFORMATION: Synthetic primer

<400> SEQUENCE: 29
aaaccggcta tggagaagag cagcc                                      25

<210> SEQ ID NO 30
<211> LENGTH: 20
<212> TYPE: DNA
<213> ORGANISM: Artificial
<220> FEATURE:
<223> OTHER INFORMATION: Synthetic primer

<400> SEQUENCE: 30
ttccagccca agtgcaaaga                                            20

<210> SEQ ID NO 31
<211> LENGTH: 25
<212> TYPE: DNA
<213> ORGANISM: Artificial
<220> FEATURE:
<223> OTHER INFORMATION: Synthetic primer

<400> SEQUENCE: 31
tgatgaatgt tccttaaaac aagca                                      25
```

KINASE NEK10 AND ITS USE IN TREATING AND DIAGNOSING BRONCHIECTASIS AND OTHER RESPIRATORY DISORDERS

CLAIM OF PRIORITY

This application is a U.S. National Phase Application under 35 U.S.C. § 371 of International Patent Application No. PCT/US2021/013942, filed on Jan. 19, 2021, which claims the benefit of U.S. Provisional Patent Application No. 62/961,817, filed on Jan. 16, 2020, and U.S. Provisional Patent Application No. 62/962,434, filed on Jan. 17, 2020, each of which is incorporated by reference herein in its entirety.

FEDERALLY SPONSORED RESEARCH OR DEVELOPMENT

This invention was made with government support under Grant Nos. HL116275, CA129105, and AI047389 awarded by the National Institutes of Health. The government has certain rights in the invention.

SEQUENCE LISTING

This application contains a Sequence Listing that has been submitted electronically as an ASCII text file named 'Sequence_Listing'. The ASCII text file, created on Jul. 14, 2022, is 15,960 bytes in size. The material in the ASCII text file is hereby incorporated by reference in its entirety.

FIELD OF THE INVENTION

The subject matter disclosed herein generally relates to methods and compositions for treating and diagnosing bronchiectasis and other respiratory disorders.

BACKGROUND OF THE INVENTION

Mucociliary clearance, the physiological process by which mammalian conducting airways expel pathogens and unwanted surface materials from the respiratory tract, depends on the coordinated function of multiple specialized cell types including basal stem cells, mucus-secreting goblet cells, motile ciliated cells, CFTR-rich ionocytes, and immune cells. Bronchiectasis, a syndrome of pathological airway dilation associated with impaired mucociliary clearance, may occur sporadically or with Mendelian inheritance, such as in cystic fibrosis (CF), primary ciliary dyskinesia (PCD), and select immunodeficiencies. Prior studies have identified mutations affecting ciliary structure and nucleation in primary ciliary dyskinesia (PCD), but the regulation of mucociliary transport remains incompletely understood and therapeutic targets for modulating it are lacking.

SUMMARY OF THE INVENTION

The present disclosure is based, at least in part, on the finding that a bronchiectasis syndrome is caused by inactivating mutations in NEK10, a protein kinase with previously unknown in vivo function in mammals. Experimental data provided herein demonstrated that NEK10 is a ciliated-cell specific kinase that regulates the motile ciliary proteome to promote ciliary length and mucociliary transport, but it is dispensable for normal ciliary number, radial structure, and beat frequency. It was also demonstrated that activation of NEK10 signaling via lentiviral delivery of wild-type NEK10 or a hyperactive NEK10 mutant (e.g., NEK10$^{S684D}$) to cultured human airway epithelium augmented experimental mucociliary clearance to supraphysiological levels.

Accordingly, aspects of the present disclosure provide a method of treating a respiratory disorder, the method comprising administering to a subject in need thereof an effective amount of NEK10.

In some embodiments, NEK10 is wild-type NEK10 comprising SEQ ID NO: 1 or a fragment thereof. In some embodiments, NEK10 is a NEK10 mutant comprising an amino acid sequence that is at least 80% identical to SEQ ID NO: 1. In some embodiments, the amino acid sequence is at least 90% identical to SEQ ID NO: 1. In some embodiments, the amino acid sequence is at least 95% identical to SEQ ID NO: 1. In some embodiments, the amino acid sequence comprises an amino acid substitution at position S684. In some embodiments, the amino acid substitution at position S684 is S684D.

In some embodiments, the respiratory disorder is selected from the group consisting of asthma, bronchiectasis, chronic obstructive pulmonary disease (COPD), cystic fibrosis (CF), emphysema, primary ciliary dyskinesia (PCD), and immunodeficiency.

In some embodiments, the subject is a human patient.

In another aspect, the present disclosure provides a method of diagnosing a subject as having a respiratory disorder, the method comprising providing a sample from the subject, and detecting a mutation in NEK10 in the sample, wherein presence of the mutation in NEK10 indicates that the subject has a respiratory disorder, or detecting a level of NEK10 in the sample and comparing the level of NEK10 in the sample to a reference level, wherein presence of a level of NEK10 in the sample that is below the reference level indicates that the subject has a respiratory disorder.

In some embodiments, the mutation in NEK10 is selected from the group consisting of NM_152534:c.1230+5G>C (insertion of VTALLLK), NM_152534:c.1869dupT (H624Sfs*4), NM_152534:c.2243C>T (P748L), NM_152534:c.1373+1G>T (C437Tfs*9), and NM_152534: c.2317C>T (R773C).

In some embodiments, methods described herein further comprise treating the subject with an effective amount of a therapy selected from the group consisting of NEK10, a bronchodilator, an antibiotic, an expectorant, oxygen therapy, chest physiotherapy, an anti-inflammatory agent, and a mucolytic.

In some embodiments, NEK10 is wild-type NEK10 comprising SEQ ID NO: 1 or a fragment thereof. In some embodiments, NEK10 is a NEK10 mutant comprising an amino acid sequence that is at least 80% identical to SEQ ID NO: 1. In some embodiments, the amino acid sequence is at least 90% identical to SEQ ID NO: 1. In some embodiments, the amino acid sequence is at least 95% identical to SEQ ID NO: 1. In some embodiments, the amino acid sequence comprises an amino acid substitution at position S684. In some embodiments, the amino acid substitution at position S684 is S684D.

In some embodiments, the sample is a blood sample or a tissue sample. In some embodiments, the sample is obtained from a subject having or at risk for having a respiratory disorder.

In some embodiments, the respiratory disorder is selected from the group consisting of asthma, bronchiectasis, chronic obstructive pulmonary disease (COPD), cystic fibrosis (CF), emphysema, primary ciliary dyskinesia (PCD), and immunodeficiency.

In some embodiments, the subject is a human patient.

In another aspect, the present disclosure provides a method of increasing mucociliary transport (MCT) in an airway epithelium, the method comprising administering an effective amount of NEK10 to the airway epithelium. In some embodiments, the airway epithelium is in vitro or in vivo.

BRIEF DESCRIPTION OF THE DRAWINGS

FIGS. 1A-1H include data showing that familial bronchiectasis is associated with NEK10 loss-of-function. FIG. 1A includes a representative image from chest computed tomography (CT) imaging of proband 1 upon clinical presentation. Dashed line indicates level of cross-sectional imaging in right panel. Arrows highlight cystic bronchiectatic destruction of lung. FIG. 1B includes a representative image from transmission electron micrograph of proband 1 nasal biopsy specimen demonstrating normal radial ciliary ultrastructure, scale bars indicate 100 nm. FIG. 1C includes a schematic depiction of 3' terminus of NEK10 exon 15 and following intron, Sanger sequencing traces highlight G>C point mutation (bold nucleotide) and high degree of conservation (dashed box). FIG. 1D includes a graph showing 18S rRNA-normalized relative expression of indicated amplicons; n=3 independent lung tissue donors (controls), n=5 independently isolated lung regions (NEK10$^{G>C}$), n=3 independently isolated HBEC lines for NEK10$^{G>C}$, n=1 for remaining samples, mean±S.D. FIG. 1E includes a representative image from immunoblotting against the indicated proteins from cultured HBECs and ALI, NEK10 immunogen indicated, representative of 3 experiments. FIG. 1F includes a schematic representation of NEK10 cDNA sequencing results from indicated genotypes, common and NEK10$^{G>C}$ specific residues indicated, canonical and cryptic splice donor motifs highlighted. FIG. 1G includes a representative image from immunoblotting after transient transfection of HEK293T cells with the indicated cDNAs, representative of 2 experiments. FIG. 1H includes a graph of results from genome-wide linkage analysis incorporating individuals (n=15) highlighted with asterisks in (FIGS. 5A, 5E, 5G), peak bounded by marker SNPs rs13072262 and rs17798444, grey line indicates LOD 3.3, equivalent to genome-wide p<0.05. Images in (FIG. 1C) and (FIG. 1F) generated from UCSC genome browser hg19 assembly (genome.ucsc.edu).

FIGS. 2A-2J include data showing that NEK10 is a ciliated cell-specific gene required for effective mucociliary transport. FIG. 2A includes a graph showing 18S rRNA-normalized relative expression of indicated transcripts from FACS-sorted ALI cells; dashed line indicates expression level from unsorted mature ALI. FIG. 2B includes a representative image of confocal immunofluorescence of GFP in ciliated cells in NEK10p:eGFP ALI, representative of 2 independent ALI differentiations, scale bar 10 μm. FIG. 2C includes representative images from pseudocolored video microscopy of ALI of the indicated genotypes, representative of 3 independent ALI differentiations, scale bars 50 μm. FIG. 2D includes a graph showing mucociliary transport (MCT) (micro-optical coherence tomography (μOCT)) of mature ALI of the indicated genotypes, n=485 (NEK10$^{WT}$), 180 (NEK10$^{G>C}$) pooled from 3 independent ALI differentiations, plot indicates median (center line), $25^{th}/75^{th}$ percentiles (box), $10^{th}/90^{th}$ (whiskers) percentiles, and remaining points (open circles). FIG. 2E includes a graph of periciliary liquid layer (PCL) (μOCT) of ALI of the indicated genotypes, n=11 (NEK10WT), 12 (NEK10G>C) pooled from 3 independent ALI differentiations, mean±S.E.M. FIG. 2F includes representative images from pseudocolored video microscopy of CRISPR/Cas9-edited ALI, representative fields from 3 independent ALI differentiations, scale bars 50 μm. FIG. 2G includes a graph showing mucociliary transport (MCT) of CRISPR/Cas9-edited ALI, n=361 (sgAAVS1), 131 (sgNEK10a), 59 (sgNEK10b), 104 (sgNEK10c) pooled from 3 independent ALI differentiations plotted as in (FIG. 2D). FIG. 2H includes a graph of periciliary liquid layer (PCL) of CRISPR/Cas9-edited ALI, n=4 (sgAAVS1), 4 (sgNEK10a), 5 (sgNEK10b), 6 (sgNEK10c) pooled from 3 independent ALI differentiations, mean±S.E.M. FIG. 2I includes a graph showing mucociliary transport (MCT) of NEK10$^{G>C}$ ALI expressing the indicated cDNAs, n=71 (no cDNA), 254 (NEK10$^{WT}$), 129 (NEK10$^{K548R}$), 1081 (NEK10$^{S684D}$), pooled from 3 independent ALI differentiations, mean±S.E.M. FIG. 2J includes a graph showing mucociliary transport (MCT) of NEK10$^{WT}$ ALI expressing the indicated cDNAs, n=1385 (FOXJ1:NEK10$^{K548R}$), 1624 (FOXJ1:NEK10$^{WT}$), 728 (FOXJ1:NEK10$^{S684D}$), 401 (NEK10:NEK10$^{K548R}$), 426 (NEK10:NEK10$^{WT}$) pooled from 3 independent ALI differentiations, plotted as in (FIG. 2G). *p≤0.05, p≤0.01, **p≤0.0001.

FIGS. 3A-3H include data showing morphologically abnormal ciliated cells in NEK10-deficient airway. FIG. 3A includes a schematic masking workflow for IFC morphological analysis. FIG. 3B includes a histogram of ciliary zone thickness of mature ALI MCCs of the indicated genotypes, n=4108 (NEK10$^{WT}$), 3513 (NEK10$^{G>C}$), shaded bars indicate medians±0.25 μm. FIG. 3C includes a histogram of ciliary area of mature ALI MCCs of the indicated genotypes, n=4108 (NEK10$^{WT}$), 3513 (NEK10$^{G>C}$). FIG. 3D includes single cell images taken from the shaded regions in (FIG. 3B), scale bars 7 μm. FIG. 3E includes representative images of confocal maximum intensity projections (MIPs) of ALI of the indicated genotype and maturity following IF against Ac-α-tubulin, representative of 3 independent ALI differentiations, scale bars 25 μm (left 4 panels) and 10 μm (right 2 panels). FIG. 3F includes representative images of confocal MIPs of mature ALI after IF against basal body marker centrin, dashed boxes mark full resolution regions in middle panels, scale bars 10 μm (left 2 panels) and 1 μm (middle 2 panels); column graph: centrin puncta per μm2 (mean±S.D.) of ciliated cell surface area, n=71 cells and 10,855 puncta (NEK10$^{WT}$), 38 cells and 5,369 puncta (NEK10$^{G>C}$) pooled from 4 independent ALI differentiations. FIG. 3G includes representative images of confocal MIPs of mature ALI after IF against PCP marker Vangl1, dashed boxes mark full resolution regions in right panel, scale bars 10 μm (left panels) and 2.5 μm (right panels), representative of 3 independent ALI differentiations. FIG. 3H includes representative images of hematoxylin/eosin stained human large airway tissue; upper 3 samples taken from lung explants during transplantation for end-stage bronchiectasis due to the indicated etiologies, $4^{th}$ sample from patient undergoing resection for an unrelated diagnosis, scale bars 5 μm. ****p≤0.0001.

FIGS. 4A-4F include data showing that NEK10 regulates ciliary length through widespread effects on the ciliary proteome. FIG. 4A includes representative images from SEM of mature ALI of the indicated genotype, dashed boxes mark full resolution regions in right panel, scale bars 10 μm (left panels) or 1 μm (right panels), representative of 3 independent ALI differentiations. FIG. 4B includes representative images from STEM of mature ALI of the indicated genotype after embedding and sectioning orthogonal to the epithelial surface, tick marks spaced at 1 μm, representative of 3 independent ALI differentiations. FIG. 4C includes representative negative stain EM grids prepared from purified cilia of the indicated genotypes, red scale bar indicates 1 μm, representative of 2 independent ALI differentiations. FIG. 4D includes a histogram of ciliary length from purified cilia of the indicated genotypes, n=101 (NEK10$^{WT}$), 102 (NEK10$^{G>C}$) pooled from 2 independent ALI differentiations; inset: box-and-whisker plot of these data, center-line indicates median, box bounds 25$^{th}$ and 75$^{th}$ percentile, whiskers indicate 1.5*IQR, circles indicate outliers. FIG. 4E includes a graph of cumulative distribution of phosphopeptides by log$_2$ fold change, previously identified motile ciliary proteins in grey, all other detected proteins in black, sgNEK10b and sgNEK10c are independently targeting guide RNAs validated in (FIG. 7D). FIG. 4F includes a table of ciliary genes by functional class with phosphopeptides depleted≥2-fold upon NEK10 deletion. ****p≤0.0001.

FIGS. 5A-5O include data showing recurrent NEK10 mutations in familial bronchiectasis. FIG. 5A includes a pedigree indicating affected siblings (filled), proband ("p"), and subjects from whom genomic DNA was available for analysis (asterisks). FIG. 5G includes a pedigree of kindred 3; dashed line indicates consanguinity by shared geographical ancestry, Sanger sequencing trace confirming c.2243C>T. FIG. 5H includes a representative image of CT from proband 3 demonstrating cystic (arrow) and cylindrical (arrow) bronchiectasis. FIG. 5I includes a pedigree of kindred 4; Sanger sequencing trace confirming c.1371+1G>T. FIG. 5L includes a pedigree of kindred 5; dashed line indicates consanguinity by shared tribal ancestry, Sanger sequencing trace confirming c.2317C>T. FIGS. 5N-5O include representative images from nasal biopsy TEM of affected siblings in (FIG. 5L), scale bars 1 μm (FIG. 5N), 200 nm (FIG. 5O).

FIGS. 6A-6I include data showing that NEK10 loss does not detectably alter airway epithelial differentiation. FIG. 6A includes a graph of 18S rRNA-normalized relative NEK10 expression during ALI differentiation; n=1 ALI culture per timepoint. FIGS. 6B-6D include graphs of 18S rRNA-normalized relative expression of ciliated cell markers FOXJ1, DNAH5 (FIG. 6B), secretory cell marker SCGB1A1 (FIG. 6C), and basal cell marker KRT5 (FIG. 6D); n=1 ALI culture per timepoint. FIGS. 6E-6F include representative images and graphs from quantification of immunofluorescence from whole-mount immunofluorescence microscopy against SCGB1A1 (FIG. 6E, upper panel), goblet cell marker MUC5AC (FIG. 6E, lower panel), KRT5 (FIG. 6F, upper panel), ciliated cell marker acetylated-α-tubulin (FIG. 6F, lower panel); scale bars 100 μm; bar graphs indicate fraction of surface epithelium occupied by marker-positive cells, n=4 per condition representative of 6 ALI differentiations, mean±S.D. FIG. 6G includes a schematic depiction of bioinformatic NEK10 promoter (grey) identification using indicated UCSC genome browser (hg19) tracks: CpG islands, H3K27-Ac, DNAse I hypersensitivity clusters, transcription factor (TF) chromatin immunoprecipitation sequencing (ChIP-seq). FIG. 6H includes representative images from live GFP imaging of ALI cultures of the indicated genotypes and maturity, representative of 3 independent ALI differentiations; scale bars 200 μm. FIG. 6I includes plots showing gating strategy for FACS sorting of GFP-labeled ALI cultures, numbers indicate percentage gated cells per population.

FIGS. 7A-7J include data showing functional consequences of NEK10 activity manipulation. FIG. 7A includes a graph showing quantitation of analysis in (FIG. 2C), mean±S.D. FIG. 7B includes representative kymographs of μOCT-based particle tracking from mature ALI, representative of 3 independent ALI differentiations. FIG. 7C includes a graph of CBF (μOCT) of mature ALI of the indicated genotypes, n=27 (NEK10$^{WT}$), 22 (NEK10$^{G>C}$) pooled from 3 independent ALI differentiations, mean±S.E.M. FIG. 7D includes a representative image from immunoblotting of mature ALI lysates after CRISPR/Cas9-mediated gene editing with the indicated sgRNAs, representative of 2 experiments; short (S) versus long (L) exposures indicated. FIG. 7E includes a graph of quantitation of analysis in (FIG. 2F), mean±S.D. FIG. 7F includes a graph of CBF of mature ALI edited with the indicated sgRNAs, n=8 per condition pooled from 3 independent ALI differentiations, mean±S.E.M. FIG. 7G includes a representative image from immunoblotting of mature ALI lysates transduced with the indicated cDNAs, representative of 2 experiments; short (S) versus long (L) exposures indicated. FIG. 7H includes a graph of quantitation of analysis in (FIG. 7I), mean±S.D. FIG. 7I includes representative images from pseudocolored video microscopy of mature ALI transduced with the indicated cDNAs, representative fields from 3 independent ALI differentiations, scale bars 50 μm. FIG. 7J includes a graph of CBF of mature ALI transduced with the indicated cDNAs, n=4 per condition pooled from 3 independent ALI differentiations, mean±S.E.M. *p≤0.05, p≤0.01, **p≤0.0001.

FIG. 8A includes a plot showing gating strategy for imaging flow cytometry analysis of MCCs. FIG. 8B includes representative images and masking data of cells in (FIG. 8A), demonstrating ability to generate single NEK10:eGFP+ ciliated cells for analysis. FIG. 8C includes representative images of confocal maximum intensity projections of mature ALI edited with the indicated sgRNAs after IF against Ac-α-tubulin, scale bars 25 μm, representative of 2 independent ALI differentiations. FIG. 8D includes representative images of confocal maximum intensity projections of mature ALI transduced with the indicated cDNAs after IF against Ac-α-tubulin, scale bars 25 μm, representative of 2 independent ALI differentiations. FIG. 8E includes representative images of H&E stained mature ALI samples of the indicated genotypes after sectioning orthogonal to the epithelial surface, representative of 3 independent ALI differentiations.

FIGS. 9A-9F include data showing structural and proteomic abnormalities in NEK10-deficient airway epithelium. FIG. 9A include representative images of SEM of mature ALI edited with the indicated sgRNAs, scale bars 100 μm (upper panels) and 1 μm (lower panels), representative of 2 independent ALI differentiations. FIG. 9B include representative images from immunoblotting against the indicated proteins from lysates generated from purified cilia (lanes 2, 4) or remaining de-ciliated mature ALI (lanes 1, 3), representative of 2 experiments. FIG. 9C includes a graph of cumulative distribution of phosphopeptides by $\log_2$ fold change between indicated conditions, solid (sgNEK10b) and dashed (sgNEK10c) red lines illustrate population of depleted phosphopeptides upon NEK10 deletion. FIG. 9D includes a table of gene ontology classes enriched among genes (n=395) whose peptides are depleted>1.5 fold ($\log_2$) after targeting with sgNEK10b, enrichment level, p-values, and false discovery rates (FDR) indicated. FIG. 9E includes a graph of cumulative distribution of phosphopeptides by $\log_2$ fold change, previously validated PCD in red and all other detected proteins in black, as in (FIG. 4E). FIG. 9F includes a graph of cumulative distribution of phosphopeptides by $\log_2$ fold change, previously validated non-PCD ciliopathy loci in red and all other detected proteins in black, as in (FIG. 4E).

Figure 1A:
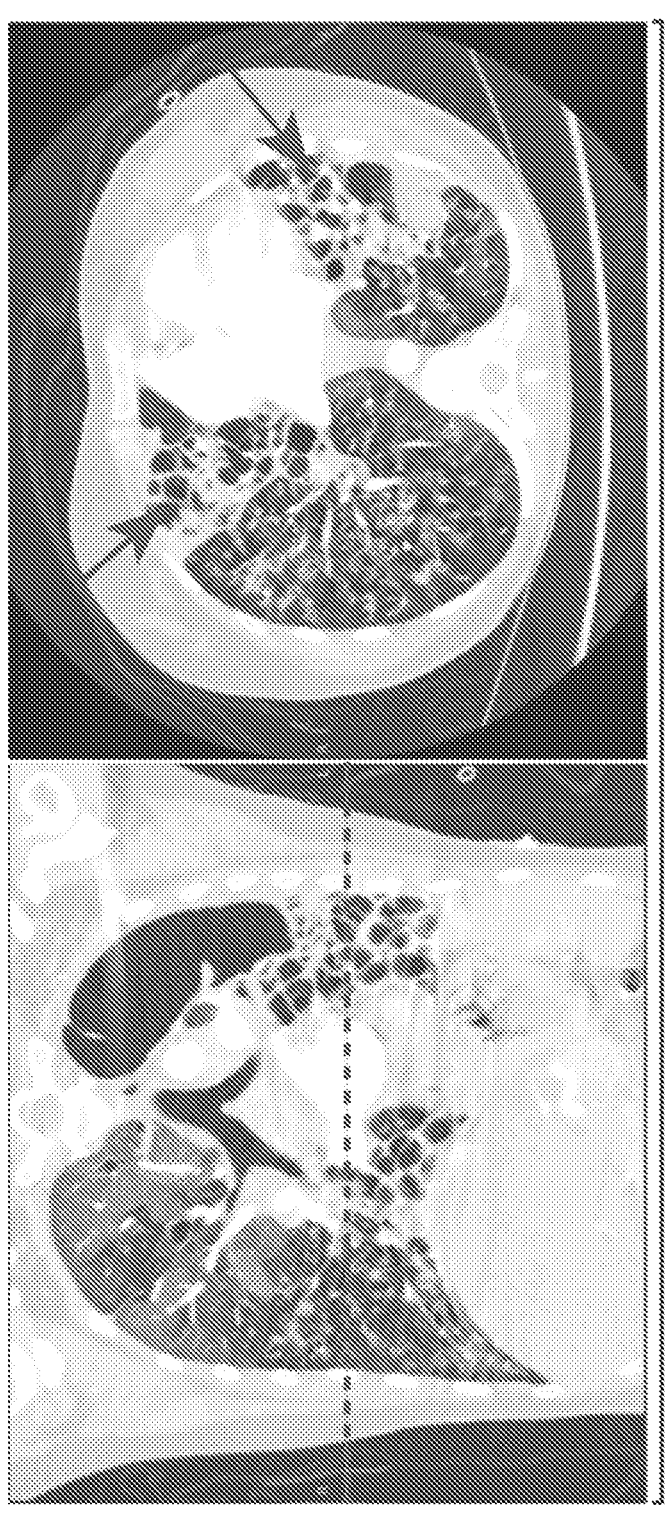

The details of one or more embodiments of the invention are set forth in the description below. Other features or advantages of the present invention will be apparent from the following drawings and detailed description of several embodiments, and also from the appended claims.

DETAILED DESCRIPTION

The present disclosure is based, at least in part, on the finding that bronchiectasis can be caused by NEK10 deficiency, which was discovered when multiple NEK10-inactivating mutations were identified in patients having unexplained bronchiectasis.

Surprisingly, it was demonstrated that bronchiectasis caused by NEK deficiency is characterized by pathologically short motile cilia, a previously undescribed human genetic phenotype. It was also demonstrated that activation of NEK10 signaling via lentiviral delivery of wild-type NEK10 or a hyperactive NEK10 mutant (e.g., NEK10$^{S684D}$) to wild-type, physiologically-relevant human airway preparations augmented experimental mucociliary clearance to supraphysiological levels.

Accordingly, the present disclosure provides, in some aspects, therapeutic uses of NEK10, for example, a wild-type NEK10 or a hyperactive NEK10 mutant such as NEK10$^{S684D}$, for treating a respiratory disorder such as bronchiectasis. Diagnostic uses of NEK10 and compositions comprising NEK10 are also within the scope of the present disclosure.

I. NEK10 and Compositions Comprising Such

Aspects of the present disclosure provide NEK10 proteins, NEK10-encoding nucleic acids, vectors comprising such, and host cells comprising the encoding nucleic acids and/or the vectors.

(a) NEK10

NEK10 is a member of the Nek (NIMA-related kinase) family of serine/threonine protein kinases, which play a role in various aspects of the cell cycle. Experimental data provided herein demonstrated that inactivating mutations in NEK10 caused a bronchiectasis syndrome. Accordingly, provided herein, are compositions comprising NEK10 for treating respiratory disorders such as bronchiectasis.

NEK10 can be from humans, although other NEK10 homologs can also be used. It should be understood that wild-type NEK10 or a fragment thereof can be used or modified versions of NEK10 can be used, e.g., hyperactive NEK10 mutants provided herein. The amino acid sequence of human NEK10 can be found as UniProt Accession No. Q6ZWH5, which is provided herein as SEQ ID NO: 1.

```
Amino acid sequence of human NEK10 (SEQ ID NO: 1):
MPDQDKKVKTTEKSTDKQQEITIRDYSDLKRLRCLLNVQSSKQQLPAIN

FDSAQNSMTKSEPAIRAGGHRARGQWHESTEAVELENFSINYKNERNFS

KHPQRKLFQEIFTALVKNRLISREWVNRAPSIHFLRVLICLRLLMRDPC

YQEILHSLGGIENLAQYMEIVANEYLGYGEEQHTVDKLVNMTYIFQKLA

AVKDQREWVTTSGAHKTLVNLLGARDTNVLLGSLLALASLAESQECREK

ISELNIVENLLMILHEYDLLSKRLTAELLRLLCAEPQVKEQVKLYEGIP

VLLSLLHSDHLKLLWSIVWILVQVCEDPETSVEIRIWGGIKQLLHILQG

DRNEVSDHSSIGSLSSANAAGRIQQLHLSEDLSPREIQENTFSLQAACC

AALTELVLNDTNAHQWQENGVYTIAKLILPNKQKNAAKSNLLQCYAFRA

LRFLFSMERNRPLFKRLEPTDLEEIFIDIGHYVRDISAYEELVSKLNLL

VEDELKQIAENIESINQNKAPLKYIGNYAILDHLGSGAFGCVYKVRKHS

GQNLLAMKEVNLHNPAFGKDKKDRDSSVRNIVSELTIIKEQLYHPNIVR

YYKTFLENDRLYIVMELIEGAPLGEHFSSLKEKHHHFTEERLWKIFIQL

CLALRYLHKEKRIVHRDLTPNNIMLGDKDKVTVTDFGLAKQKQENSKLT

SWGTILYSCPEVLKSEPYGEKADVWAVGCILYQMATLSPPFYSTNMLSL

ATKIVEAVYEPVPEGIYSEKVTDTISRCLTPDAEARPDIVEVSSMISDV

MMKYLDNLSTSQLSLEKKLERERRRTQRYFMEANRNTVTCHHELAVLSH

ETFEKASLSSSSSGAASLKSELSESADLPPEGFQASYGKDEDRACDEIL

SDDNFNLENAEKDTYSEVDDELDISDNSSSSSSSPLKESTFNILKRSFS

ASGGERQSQTRDFTGGTGSRPRPALLPLDLLLKVPPHMLRAHIKEIEAE

LVTGWQSHSLPAVILRNLKDHGPQMGTFLWQASAGIAVSQRKVRQISDP

IQQILIQLHKIIYITQLPPALHHNLKRRVIERFKKSLFSQQSNPCNLKS

EIKKLSQGSPEPIEPNFFTADYHLLHRSSGGNSLSPNDPTGLPTSIELE

EGITYEQMQTVIEEVLEESGYYNFTSNRYHSYPWGTKNHPTKR
```

In some embodiments, NEK10 comprises a full-length protein. For example, NEK10 comprises the full-length amino acid sequence provided in SEQ ID NO: 1. In some examples, NEK10 comprises an amino acid sequence that is at least 70%, at least 80%, at least 85%, at least 90%, at least 91%, at least 92%, at least 93%, at least 94%, at least 95%, at least 96%, at least 97%, at least 98%, or at least 99% identical to SEQ ID NO: 1.

In some embodiments, NEK10 comprises a fragment of a full-length protein. For example, NEK10 comprises a fragment of the full-length amino acid sequence provided in SEQ ID NO: 1. In some examples, NEK10 comprises a fragment that is at least 70%, at least 80%, at least 85%, at least 90%, at least 91%, at least 92%, at least 93%, at least 94%, at least 95%, at least 96%, at least 97%, at least 98%, or at least 99% identical to the full-length amino acid sequence provided in SEQ ID NO: 1.

The fragment of the full-length NEK10 protein can be any suitable length. For example, the fragment is at least 250 amino acids, at least 300 amino acids, at least 400 amino acids, at least 500 amino acids, at least 600 amino acids, at least 700 amino acids, at least 800 amino acids, at least 900 amino acids, or at least 1000 amino acids in length.

In some embodiments, NEK10 comprises a NEK10 mutant, which can be a full-length protein or a fragment thereof having at least one mutation. The term "mutation" refers to a substitution of a residue within a sequence (e.g., a nucleic acid or an amino acid sequence) with another residue, or a deletion or insertion of one or more residues within a sequence (e.g., a nucleic acid or an amino acid sequence). Mutations are typically described herein by identifying the original residue followed by the position of the residue within the sequence and by the identity of the newly substituted residue. Various methods for making the amino acid mutations provided herein are well known in the art, and are provided by, e.g., Green and Sambrook, Molecular Cloning: A Laboratory Manual (4th ed., Cold Spring Harbor Laboratory Press, Cold Spring Harbor, N.Y. (2012).

The NEK10 mutant can comprise any number and/or any type of mutation. In some examples, the NEK10 mutant is a hyperactive NEK10 mutant capable of a biological activity (e.g., kinase activity) that is hyperactive compared to a wild-type NEK10.

For example, when the hyperactive NEK10 mutant is capable of hyperactive kinase activity, the hyperactive NEK10 mutant comprises a substitution at position S684 in SEQ ID NO: 1 (e.g., NEK10$^{S684D}$). Alternatively, or in addition to, the hyperactive NEK10 mutant comprises a substitution at position Y590 in SEQ ID NO: 1 (e.g., NEK10$^{Y590A}$).

Without wishing to be bound by theory, position S684 is located in the activation loop of the catalytic domain of NEK10, and it is understood that phosphomimetic substitutions with aspartate or glutamate lead to constitutive activation of NEK10. Also, without wishing to be bound by theory, mutation at position Y590 is understood to release tyrosine from its autoinhibitory position.

It should be understood that the amino acid substitution at position S684 or at position Y590 in the NEK10 from humans can be incorporated into NEK10 from various sources with similar effects on the kinase activity of the NEK10.

In some examples, the NEK10 mutant is capable of compensating for a defect associated with NEK10 mutations such as reduced mucociliary transport (MCT), reduced maximal particle transport velocity, reduced ciliary length, thinning of the periciliary liquid layer (PCL), altered kinase activity, or a combination thereof.

NEK10 proteins described herein can be NEK10 fusion proteins. In such instances, NEK10 can be fused to a peptide or a protein such as an affinity tag for purification or identification (e.g., a His-tag), a fluorescent tag for visualization (e.g., a GFP-tag), or a cell-penetrating peptide (CPP) for uptake into cells.

(b) Nucleic Acids Encoding NEK10 and Cells Comprising Such

Also within the scope of the present disclosure are nucleic acids encoding NEK10 proteins (also referred to as NEK10-encoding nucleic acids), vectors comprising such, and cells comprising the nucleic acids encoding NEK10 and/or the vectors.

NEK10-encoding nucleic acids can be DNA or RNA, single-stranded and/or double-stranded, and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

NEK10-encoding nucleic acids can include natural nucleosides (e.g., adenosine, thymidine, guanosine, cytidine, uridine, deoxyadenosine, deoxythymidine, deoxyguanosine, and deoxycytidine) and/or modified nucleosides such as nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine), chemically modified bases, biologically modified bases (e.g., methylated bases), intercalated bases, modified sugars (e.g., 2-fluororibose, ribose, 2'-deoxyribose, arabinose, and hexose), and/or modified phosphate groups (e.g., phosphorothioates and 5'-N-phosphoramidite linkages).

NEK10-encoding nucleic acids can be introduced into cells using any means known in the art, including, without limitation, transformation, transfection (e.g., chemical transfection using calcium phosphate, cationic polymers, or liposomes) or non-chemical (e.g., electroporation, optical transfection, hydrodynamic transfection), and transduction (e.g., viral transduction).

NEK10-encoding nucleic acids can be introduced into a cell as naked nucleic acid, as nucleic acid complexed with an agent such as a liposome or a nanoparticle, or it can be delivered by viruses (e.g., adenovirus).

NEK10-encoding nucleic acids can be operably linked to a promoter, which can be an endogenous promoter or an exogenous promoter. In some examples, the promoter is a constitutive promoter, an inducible promoter, or a tissue-specific promoter. In some examples, the promoter is a FOXJ1 promoter, a NEK10 promoter, or an axonemal gene promoter.

NEK10-encoding nucleic acids can be introduced into a cell as part of a vector molecule having additional sequences such as, for example, replication origins, genes encoding antibiotic resistance, and/or transcriptional or translational regulatory sequences such as promoters, enhancers, insulators, internal ribosome entry sites, and/or polyadenylation signals.

In some examples, NEK10-encoding nucleic acids herein can be delivered to a cell using an adeno-associated virus (AAV) vectors. AAVs are small viruses which integrate site-specifically into the host genome and can therefore deliver a transgene, such as a NEK10-encoding nucleic acid. Inverted terminal repeats (ITRs) are present flanking the AAV genome and/or the transgene of interest and serve as origins of replication. Also present in the AAV genome are rep and cap proteins which, when transcribed, form capsids which encapsulate the AAV genome for delivery into target cells. Surface receptors on these capsids which confer AAV serotype, which determines which target organs the capsids will primarily bind, and thus what cells the AAV will most efficiently infect. There are twelve currently known human AAV serotypes. Any of these AAV serotypes can be used in methods described herein. In some examples, the AAV for use in delivering the NEK10-encoding nucleic acids is AAV serotype 9 (AAV9).

Adeno-associated viruses are among the most frequently used viruses for gene therapy for several reasons. First, AAVs, in some instances, do not provoke an immune response upon administration to mammals, such as humans. Second, AAVs are effectively delivered to target cells, particularly when consideration is given to selecting the appropriate AAV serotype. Finally, AAVs have the ability to infect both dividing and non-dividing cells because the genome can persist in the host cell without integration. These features make AAVs ideal for gene therapy.

Other viral vectors can be used to deliver NEK10-encoding nucleic acids to a cell. Such viral vectors include, but are not limited to, lentivirus vectors, alphavirus vectors, enterovirus vectors, pestivirus vectors, baculovirus vectors, herpesvirus vectors, Epstein Barr virus vectors, papovavirus vectors, poxvirus vectors, vaccinia virus vectors, and herpes simplex virus vectors.

Also within the scope of the present disclosure are cells comprising NEK10-encoding nucleic acids. Suitable cells include mammalian cells (e.g., human cells) and bacterial cells (e.g., recombinant bacteria cells for protein expression). In some examples, the cells are multiciliated cells (MCCs) such as epithelial cells (e.g., bronchial epithelial cells such as human bronchial epithelial cells (HBECs)).

(c) Pharmaceutical Compositions

NEK10 protein, encoding nucleic acids, vectors comprising such, or host cells comprising the encoding nucleic acids and/or the vectors can be mixed with a pharmaceutically acceptable excipient (carrier) to form a pharmaceutical composition for use in treating a respiratory disorder (e.g., bronchiectasis). "Acceptable" means that the excipient must be compatible with the active ingredient of the composition (and preferably, capable of stabilizing the active ingredient) and not deleterious to the subject to be treated. Pharmaceutically acceptable excipients (carriers), including buffers, are well known in the art. See, e.g., Remington: The Science and Practice of Pharmacy $20^{th}$ Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. Acceptable carriers, excipients, or stabilizers are nontoxic to recipients at the dosages and concentrations used, and may comprise buffers (e.g., phosphate, citrate, and other organic acids); antioxidants (e.g., ascorbic acid, methionine); preservatives (e.g., octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins (e.g., serum albumin, gelatin, immunoglobulins); hydrophilic polymers (e.g., polyvinylpyrrolidone); amino acids (e.g., glycine, glutamine, asparagine, histidine, arginine, lysine); monosaccharides, disaccharides, and other carbohydrates including glucose, mannose, or dextrans; chelating agents (e.g., ETDA) sugars (e.g., sucrose, mannitol, sorbitol); salt-forming counter-ions (e.g., sodium); metal complexes (e.g., Zn-protein complexes); and/or non-ionic surfactants (e.g., TWEEN™, PLURONICS™, polyethylene glycol (PEG)).

In some examples, the pharmaceutical composition described herein comprises liposomes containing NEK10 (e.g., NEK10 protein or nucleic acids encoding such). Such liposomes can be prepared using any method known in the art.

Alternatively, or in addition to, NEK10 can be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (e.g., liposomes, albumin microspheres, microemulsions, nanoparticles and nanocapusules) or in macroemulsions.

In other examples, the pharmaceutical compositions described herein can be formulated in sustained-release format. Suitable examples of sustained-release preparations include semi-permeable matrices of solid hydrophobic polymers containing NEK10, which matrices are in the form of shaped articles, e.g., films or microcapsules. Examples of sustained-release matrices include polyesters, hydrogels (e.g., poly(2-hydroxyethyl-methacrylate), poly(vinyl alcohol)), polylactides, copolymers of L-glutamic acid and ethyl-L-glutamate, non-degradable ethylene-vinyl acetate, degradable lactic acid-glycolic acid copolymers, sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Pharmaceutical compositions described herein can be placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient (i.e., NEK such as NEK10 protein or encoding nucleic acids) can be mixed with a pharmaceutical carrier, e.g., conventional tableting ingredients such as corn starch, lactose, sucrose, sorbital, talc, stearic acid, magnesium stearate, dicalcium phosphate or gums, and other pharmaceutical diluents, e.g., water, to form a solid preformulation composition containing a homogeneous mixture of an active ingredient. When referring to these preformulation compositions as homogeneous, it is meant that the active ingredient is dispersed evenly throughout the composition so that the composition can be readily subdivided into equally effective unit dosage forms such as tablets, pills, and capsules. This solid preformulation composition is then subdivided into unit dosage forms of the type described above containing from 0.1 to about 500 mg of the active ingredient of the present invention. The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coating, such materials including a number of polymeric acids and mixtures of polymeric acids with such materials as shellac, cetyl alcohol, and cellulose acetate.

Suitable surface-active agents include, but are not limited to, non-ionic agents, such as polyoxyethylenesorbitans (e.g., Tween™20, 40, 60, 80 or 85) and other sorbitans (e.g., Span™20, 40, 60, 80, or 85). Compositions with a surface-active agent can comprise between 0.05% and 5% surface-active agent (e.g., between 0.1% and 2.5%). It will be appreciated that other ingredients may be added, for example mannitol or other pharmaceutically acceptable vehicles, if necessary.

Suitable emulsions can be prepared using commercially available fat emulsions, such as Intralipid™, Liposyn™, Infonutrol™, Lipofundin™, and Lipiphysan™. The active ingredient (i.e., NEK such as NEK10 protein or encoding nucleic acids) can be either dissolved in a pre-mixed emulsion composition or alternatively it may be dissolved in an oil (e.g., soybean oil, safflower oil, cottonseed oil, sesame oil, corn oil, or almond oil) and an emulsion formed upon mixing with a phospholipid (e.g., egg phospholipids, soybean phospholipids or soybean lecithin) and water. It will be appreciated that other ingredients can be added, for example glycerol or glucose, to adjust the tonicity of the emulsion. Suitable emulsions will typically contain up to 20% oil, for example, between 5% and 20%. The fat emulsion can comprise fat droplets between 0.1 and 1.0 μm, e.g., 0.1 and 0.5 μm, and have a pH in the range of 5.5 to 8.0.

Pharmaceutical compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as set out above. In some examples, the pharmaceutical compositions are administered by the oral or nasal respiratory route for local or systemic effect.

Compositions in preferably sterile pharmaceutically acceptable solvents can be nebulized by use of gases. Nebulized solutions can be breathed directly from the nebulizing device or the nebulizing device can be attached to a face mask, tent or intermittent positive pressure breathing machine. Solution, suspension, or powder compositions may be administered orally or nasally, from devices which deliver the formulation in an appropriate manner.

II. Application of NEK10 in Diagnosis and Treatment

The present disclosure provides, in some aspects, uses of NEK10 in the diagnosis and treatment of respiratory disorders such as bronchiectasis.

(a) Diagnostic Methods

Aspects of the present disclosure provide methods for diagnosis of a respiratory disorder (e.g., bronchiectasis) based on detection of NEK10 in a biological sample (e.g., a blood sample) collected from a subject (e.g., a human patient at risk for having a respiratory disorder such as bronchiectasis).

Detection of NEK10 in a biological sample includes detection of a mutation in NEK10 and/or detection of a level of NEK10. In some examples, detection of NEK10 involves detecting presence of a mutation in NEK10. Alternatively, or in addition to, detection of NEK10 involves detecting the level of NEK10.

When methods involve detecting presence of a mutation in NEK10, the mutation can be a nucleic acid mutation, an amino acid mutation, or both. The mutation in NEK10 can be a substitution (e.g., a point mutation resulting in an amino acid substitution, a frameshift, or a stop codon), an insertion, a deletion, or a combination thereof.

For example, the mutation in NEK10 is NM_152534: c.1230+5G>C (referred to as "NEK10$^{G>C}$") causing in-frame insertion of 7 amino acids. In another example, the mutation in NEK10 is NM_152534:c.1869dupT mutation resulting in frameshift and premature stop (His624Serfs*4). In another example, the mutation in NEK10 is NM_152534:

c.2243C>T mutation causing substitution of leucine for a highly conserved proline (Pro748Leu) within the kinase domain. In another example, the mutation in NEK10 is NM_152534:c.1373+1G>T mutation causing exon skipping, frameshift, and premature stop (Cys437Thrfs*9). In yet another example, the mutation in NEK10 is NM_152534:c.2317C>T mutation resulting in mutation of a highly conserved arginine to cysteine (Arg773Cys).

When methods involve detecting the level of NEK10, the NEK10 level is then compared to a reference value to determine whether the subject has or is at risk for a respiratory disorder. The reference value can be a control level of NEK10. In some embodiments, the control level is a level of NEK10 in a control sample. In some embodiments, a control sample is obtained from a healthy subject or population of healthy subjects. As used herein, a healthy subject is a subject that is apparently free of a respiratory disorder at the time the level of NEK10 is measured or has no history of a respiratory disorder.

In some embodiments, the amount by which the level (or score) in the subject is less than the reference level (or score) is sufficient to distinguish a subject from a control subject, and optionally is a statistically significantly less than the level (or score) in a control subject. In cases where the level (or score) of NEK10 in a subject being equal to the reference level (or score) of NEK10, the "being equal" refers to being approximately equal (e.g., not statistically different).

Suitable reference values can be determined using methods known in the art, e.g., using standard clinical trial methodology and statistical analysis. The reference values can have any relevant form. In some cases, the reference comprises a predetermined value for a meaningful score or level of NEK10, e.g., a control reference level that represents a normal level of NEK10, e.g., a level in an unaffected subject or a subject who is not at risk of developing a respiratory disorder, and/or a disease reference that represents a level of NEK10 associated with risk of developing a respiratory disorder.

The predetermined level or score can be a single cut-off (threshold) value, such as a median or mean, or a level or score that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level or score is a level or score determined in the same subject, e.g., at a different time point, e.g., an earlier time point.

The control level as described herein can be determined by various methods. In some embodiments, the control level can be obtained by performing a known method. In some embodiments, the control level can be obtained by performing the same assay used for determine the level of NEK10 in a sample from a subject. In some embodiments, the control level can be obtained by performing a method described herein. In some embodiments, the control level can be obtained from members of a control population and the results can be analyzed by, e.g., a computational program, to obtain the control level (a predetermined level) that represents the level of NEK10 in the control population.

By comparing the level of NEK10 in a sample obtained from a subject to the reference value as described herein, it can be determined as to whether the subject has or is at risk for a respiratory disorder (e.g., bronchiectasis). For example, if the level of NEK10 of the subject is elevated from the reference value (e.g., increased as compared to the reference value), the candidate subject might be identified as having or at risk for a respiratory disorder (e.g., bronchiectasis). In other examples, if the level of NEK10 of the subject is reduced from the reference value (e.g., decreased as compared to the reference value), the candidate subject might be identified as having or at risk for a respiratory disorder (e.g., bronchiectasis).

As used herein, "an elevated level or a level above a reference value" means that the level of NEK10 is higher than a reference value, such as a predetermined threshold or a level of NEK10 in a control sample.

An elevated level of NEK10 includes a NEK10 level that is, for example, 1%, 5%, 10%, 20%, 30%, 40%, 50%, 60%, 70%, 80%, 90%, 100%, 150%, 200%, 300%, 400%, 500% or more above a reference value. An elevated level of NEK10 also includes increasing a phenomenon from a zero state (e.g., no or undetectable NEK10 in a sample) to a non-zero state (e.g., some or detectable NEK10 in a sample).

As used herein, "a decreased level or a level below a reference value" means that the level of NEK10 is lower than a reference value, such as a predetermined threshold or a level of NEK10 in a control sample.

An decreased level of NEK10 includes a NEK10 level that is, for example, 1%, 5%, 10%, 20%, 30%, 40%, 50%, 60%, 70%, 80%, 90%, 100%, 1500, 200%, 300%, 400%, 500% or more below a reference value. A decreased level of NEK10 also includes decreasing a phenomenon from a non-zero state (e.g., some or detectable NEK10 in a sample) to a zero state (e.g., no or undetectable NEK10 in a sample).

A subject having or a risk for having a respiratory disorder (e.g., bronchiectasis), as identified using methods described herein, can be treated with any appropriate therapy including those known in the art (e.g., bronchodilators) and those disclosed herein (e.g., wild-type NEK10 or hyperactive NEK10 mutants).

(b) Treatment Methods

To practice the treatment methods described herein, an effective amount of an appropriate therapy can be administered to a subject (e.g., a human patient) in need of the treatment via any suitable route.

Appropriate therapies for a respiratory disorder include those known in the art and those disclosed herein (e.g., wild-type NEK10 or hyperactive NEK10 mutants or editing of NEK10 genetic mutations using a suitable gene editing technology such as CRISPR-based gene editing systems). Therapies for a respiratory disorder include, but are not limited to, NEK10 therapies (e.g., NEK protein or encoding nucleic acids or editing of NEK10 genetic mutations using a suitable gene editing technology such as CRISPR-based gene editing systems), bronchodilators (e.g., short-acting bronchodilators, such as albuterol and levalbuterol, or long-acting bronchodilators, such as formoterol, tiotropium and salmeterol), antibiotics (e.g., penicillin, erythromycin, or amoxicillin), expectorants, oxygen therapy, chest physiotherapy, anti-inflammatory agents (e.g., steroids), and mucolytics (e.g., classic mucolytics such as N-acetylcysteine, carbocysteine, erdosteine, and fudosteine, or peptide mucolytics such as dornase alfa and thymosin β4).

When the therapy includes genetic editing of a mutation in NEK10 (e.g., $NEK10^{G>C}$), the genetic editing can be performed using any suitable technology, for example, clustered regularly interspaced short palindromic repeats (CRISPR), transcription activator-like effector nucleases (TALENs), zinc-finger nucleases (ZFNs), and/or homing endonucleases or meganucleases technologies.

The subject to be treated by the methods described can be a human patient having or at risk for having a respiratory disorder. Examples of a respiratory disorder include, but are not limited to, asthma, bronchiectasis (e.g., sporadic bronchiectasis), chronic bronchitis, chronic obstructive pulmonary disease (COPD), cystic fibrosis (CF), emphysema, immotile cilia syndrome, primary ciliary dyskinesia, Kartagener's syndrome, acute respiratory tract infections, chronic smoking or vaping-associated cough and conditions associated with decreased cough reflex or decreased ability to cough due to respiratory muscle weakness, spinal cord or phrenic nerve damage or other nervous system injury or disease, airway burns, immunodeficiency (e.g., IgG deficiencies, X-linked agammaglobulinemia (XLA), and other states associated with high rates of bronchiectasis).

The subject to be treated by the methods described herein can be a mammal such as a human. Mammals include, but are not limited to, farm animals, sport animals, pets, primates, horses, dogs, cats, mice, and rats. A human subject who needs the treatment can be a human patient having or a risk for having a respiratory disorder (e.g., bronchiectasis).

A subject having or at risk for having a respiratory disorder can be identified by routine medical examination, e.g., laboratory tests (e.g., blood tests), biopsy (e.g., lung biopsy), x-rays (e.g., chest x-rays), CT scans (e.g., chest CT scans), pulmonary function tests (e.g., spirometry), or pulse oximetry tests.

A subject having or at risk for having a respiratory disorder might show one or more symptoms of a respiratory disorder, e.g., chronic cough that may produce mucus that may be clear, white, yellow or greenish, or that has blood in it, chest pain or tightness, wheezing, clubbing of nails, unexplained weight loss, fatigue, fever and/or chills, increased shortness of breath, night sweats, frequent respiratory infections, and breathing difficulties.

A subject at risk for having a respiratory disorder can be a subject having one or more of the risk factors for that respiratory disorder. For example, the risk factors associated with bronchiectasis include (a) cystic fibrosis (CF), (b) infections such as tuberculosis (TB), pneumonia, fungal infection, or measles, (c) environmental factors such as inhalation of toxins, (d) blockages such as those resulting from a tumor or an inhaled object, (e) genetic abnormalities, (f) immunologic conditions, and (g) autoimmune diseases such as rheumatoid arthritis.

An effective amount of a therapy can be administered to a subject (e.g., a human) in need of the treatment via any suitable route, such as inhalation, intravenous administration (e.g., as a bolus or by continuous infusion over a period of time), intramuscular, intraperitoneal, intracerebrospinal, subcutaneous, intra-articular, intrasynovial, intrathecal, or topical routes.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of treatment, the nature of concurrent therapy, if any, the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations such as the half-life of an agent will generally contribute to the determination of the dosage. Frequency of administration can be determined and adjusted over the course of therapy, and is generally, but not necessarily, based on treatment and/or suppression and/or amelioration and/or delay of a respiratory disorder (e.g., bronchiectasis). Alternatively, sustained continuous release formulations of therapeutic agent may be appropriate. Various formulations and devices for achieving sustained release are known in the art.

As used herein, the term "treating" refers to the application or administration of a composition including one or more active agents to a subject who has a respiratory disorder (e.g., bronchiectasis), a symptom of a respiratory disorder, and/or a predisposition toward a respiratory disorder, with the purpose to cure, heal, alleviate, relieve, alter, remedy, ameliorate, improve, or affect the disorder, the symptom of the respiratory disorder, and/or the predisposition toward the respiratory disorder.

Alleviating a respiratory disorder includes delaying the development or progression of the disease, and/or reducing disease severity. Alleviating the disease does not necessarily require curative results.

As used herein, "delaying" the development of a disease (e.g., a respiratory disorder such as bronchiectasis) means to defer, hinder, slow, retard, stabilize, and/or postpone progression of the disease. This delay can be of varying lengths of time, depending on the history of the disease and/or individuals being treated. A method that "delays" or alleviates the development of a disease and/or delays the onset of the disease is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques known in the art. However, development also refers to progression that may be undetectable. For purposes of this disclosure, development or progression refers to the biological course of the symptoms. "Development" includes occurrence, recurrence, and onset. As used herein, "onset" or "occurrence of a respiratory disorder includes initial onset and/or recurrence.

In some embodiments, the therapy is administered one or more times to the subject. In some embodiments, the therapy comprises two or more types of therapies that can be administered as part of a combination therapy for treatment of a respiratory disorder (e.g., a combination therapy comprising NEK10 (e.g., NEK10 protein or encoding nucleic acids) and a bronchodilators (e.g., a short-acting bronchodilator, such as albuterol and levalbuterol, or a long-acting bronchodilator, such as formoterol, tiotropium and salmeterol)).

The term combination therapy, as used herein, embraces administration of these agents in a sequential manner, that is wherein each therapeutic agent is administered at a different time, as well as administration of these therapeutic agents, or at least two of the agents, in a substantially simultaneous manner.

Sequential or substantially simultaneous administration of each agent can be affected by any appropriate route including, but not limited to, oral routes, intravenous routes, intramuscular routes, subcutaneous routes, and direct absorption through mucous membrane tissues. The agents can be administered by the same route or by different routes. For example, a first agent can be administered orally, and a second agent can be administered intravenously.

As used herein, the term "sequential" means, unless otherwise specified, characterized by a regular sequence or order, e.g., if a dosage regimen includes the administration of a first therapeutic agent and a second therapeutic agent, a sequential dosage regimen could include administration of the first therapeutic agent, before, simultaneously, substantially simultaneously, or after administration of the second therapeutic agent, but both agents will be administered in a regular sequence or order. The term "separate" means, unless otherwise specified, to keep apart one from the other. The term "simultaneously" means, unless otherwise specified, happening or done at the same time, i.e., the agents of the invention are administered at the same time. The term "substantially simultaneously" means that the agents are administered within minutes of each other (e.g., within 10 minutes of each other) and intends to embrace joint administration as well as consecutive administration, but if the administration is consecutive it is separated in time for only a short period (e.g., the time it would take a medical practitioner to administer two agents separately). As used herein, concurrent administration and substantially simultaneous administration are used interchangeably. Sequential administration refers to temporally separated administration of the agents described herein.

(c) Detection of NEK10

Diagnostic and treatment methods described herein, in some examples, involve detection of NEK10 in a biological sample using any suitable means known in the art. In some examples, detection of NEK10 involves detecting a mutation in NEK10. Alternatively, or in addition to, detection of NEK10 involves detecting a level of NEK10. Any suitable method for detecting proteins and nucleic acids encoding such can be used for detection of NEK10.

Any sample that may contain NEK10 can be analyzed for presence of a mutation in NEK10 and/or for presence of altered levels of NEK10. In some examples, the sample can be from an in vitro assay, e.g., from an in vitro cell culture (e.g., an in vitro cell culture of human bronchial epithelial cells (HBECs)). In other examples, the sample to be analyzed can be a sample obtained from a subject. Accordingly, in some examples, diagnostic and treatment methods described herein involve providing a sample obtained from a subject.

As used herein, a "sample" refers to a composition that comprises biological materials including, but not limited to, plasma, tissue, cells, and/or fluid from a subject. A sample includes both an initial unprocessed sample taken from a subject as well as subsequently processed, e.g., partially purified or preserved forms. In some embodiments, the sample is plasma. In some embodiments, multiple (e.g., at least 2, 3, 4, 5, or more) samples may be collected from a subject, over time or at particular time intervals, for example, to assess the disease progression or evaluate the efficacy of a treatment. A sample can be obtained from a subject using any means known in the art (e.g., a biopsy such as a lung biopsy).

As used herein, the terms "detecting" or "detection," or alternatively "measuring" or "measurement," means assessing the presence, absence, quantity or amount (which can be an effective amount) of NEK10 within a sample, including the presence or the absence of a mutation in NEK10, the derivation of qualitative or quantitative concentration levels of NEK10, or otherwise evaluating the values and/or categorization of NEK10 in a sample from a subject.

Any binding agent that specifically binds to NEK10 may be used in methods described herein to detect NEK10 in a sample. In some embodiments, the binding agent is an antibody or an aptamer that specifically binds to NEK10 protein. In other embodiments, the binding agent may be one or more oligonucleotides complementary to NEK10 nucleic acid.

To detect NEK10, a sample can be in contact with a binding agent under suitable conditions. In general, the term "contact" refers to an exposure of the binding agent with the sample or cells collected therefrom for suitable period sufficient for the formation of complexes between the binding agent and NEK10 (e.g., nucleic acid or protein) in the sample, if any. In some embodiments, the contacting is performed by capillary action in which a sample is moved across a surf ace of the support membrane.

The type of detection assay used for the detection and/or quantification of NEK10 may depend on the particular situation in which the assay is to be used (e.g., clinical or research applications), on the kind of NEK10 to be detected (e.g., nucleic acid or protein), and/or on the kind and number of samples (e.g., patient samples) to be run in parallel, to name a few parameters.

In some examples, detection of NEK10 involves detecting nucleic acids encoding NEK10, which can be used to detect a mutation in NEK10 and/or a level of NEK10. Any suitable method for detecting nucleic acids such as whole exome sequencing (WES) can be used for detection of NEK10-encoding nucleic acids.

The mutation in NEK10 and/or the level of nucleic acids encoding NEK10 in a sample can be measured via any suitable method. In some embodiments, detecting nucleic acid encoding NEK10 comprises detecting DNA (e.g., cDNA) and/or RNA (e.g., mRNA).

In some examples, NEK10-encoding nucleic acids can be detected using DNA sequencing methods, hybridization methods, comparative genomic hybridization (CGH) methods, multiplex ligation-dependent probe amplification (MLPA) methods, single strand conformational polymorphism (SSCP) methods, denaturing gradient gel electrophoresis (DGGE) methods, restriction fragment length polymorphism (RFLP) methods, DNA microarray methods, or a combination thereof.

In some examples, NEK10-encoding nucleic acids can be detected using hybridization and/or amplification assays including, but not limited to, polymerase chain reaction (PCR), reverse transcriptase-PCR (RT-PCR), in situ PCR, quantitative PCR (Q-PCR), real-time quantitative PCR (RT Q-PCR), in situ hybridization, Southern blot, Northern blot, sequence analysis, microarray analysis, detection of a reporter gene, or other DNA/RNA hybridization platforms.

In some examples, NEK10-encoding nucleic acids can be detected using next-generation sequencing (NGS) technologies such as whole-genome sequencing (WGS), whole exome sequencing (WES), and transcriptome sequencing.

In some examples, detection of NEK10 involves detecting NEK10 protein, which can be used to detect a mutation in NEK10 and/or a level of NEK10. Any suitable method for detecting protein such as immunoassays can be used for detection of NEK10 protein.

In some examples, a mutation in NEK10 and/or a level of NEK10 is assessed or measured by directly detecting NEK10 protein in a sample (e.g., a plasma sample). Alternatively, or in addition to, the mutation in NEK10 protein and/or the level of NEK10 protein can be assessed or measured indirectly in a sample, for example, by detecting the activity of NEK10 protein (e.g., detecting the kinase activity of NEK10 protein).

The mutation in NEK10 protein and/or the level of NEK10 protein can be measured using an immunoassay. Examples of immunoassays include any known assay (without limitation), and can include any of the following: immunoblotting assay (e.g., Western blot), immunohistochemical analysis, flow cytometry assay, immunofluorescence assay (IF), enzyme-linked immunosorbent assays (ELISAs) (e.g., sandwich ELISAs), radioimmunoassays, electrochemiluminescence-based detection assays, magnetic immunoassays, lateral flow assays, and related techniques. Additional suitable immunoassays for detecting NEK10 protein will be apparent to those of skill in the art.

Such immunoassays can involve the use of an agent (e.g., an antibody) specific to NEK10. An agent such as an antibody that "specifically binds" to NEK10 is a term well understood in the art, and methods to determine such specific binding are also well known in the art. An antibody is said to exhibit "specific binding" if it reacts or associates more frequently, more rapidly, with greater duration and/or with greater affinity with NEK10 than it does with other proteins. It is also understood by reading this definition that, for example, an antibody that specifically binds to a first target peptide may or may not specifically or preferentially bind to a second target peptide. As such, "specific binding" or "preferential binding" does not necessarily require (although it can include) exclusive binding. Generally, but not necessarily, reference to binding means preferential binding. In some examples, an antibody that "specifically binds" to a target peptide or an epitope thereof may not bind to other peptides or other epitopes in the same antigen.

As used herein, the term "antibody" refers to a protein that includes at least one immunoglobulin variable domain or immunoglobulin variable domain sequence. For example, an antibody can include a heavy (H) chain variable region (abbreviated herein as $V_H$), and a light (L) chain variable region (abbreviated herein as $V_L$). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., *Eur J Immunol.* 1996; 26(3):629-39)) as well as complete antibodies. An antibody can have the structural features of IgA, IgG, IgE, IgD, IgM (as well as subtypes thereof). Antibodies may be from any source including, but not limited to, primate (human and non-human primate) and primatized (such as humanized) antibodies.

In some embodiments, the antibodies as described herein can be conjugated to a detectable label and the binding of the detection reagent to NEK10 can be determined based on the intensity of the signal released from the detectable label. Alternatively, a secondary antibody specific to the detection reagent can be used. One or more antibodies may be coupled to a detectable label. Any suitable label known in the art can be used for detection of NEK10 as described herein. In some embodiments, a detectable label comprises a fluorophore. As used herein, the term "fluorophore" (also referred to as "fluorescent label" or "fluorescent dye") refers to moieties that absorb light energy at a defined excitation wavelength and emit light energy at a different wavelength. In some embodiments, a detection moiety is or comprises an enzyme. In some embodiments, an enzyme is one (e.g., β-galactosidase) that produces a colored product from a colorless substrate.

It will be apparent to those of skill in the art that this disclosure is not limited to immunoassays. Detection assays that are not based on an antibody, such as mass spectrometry, are also useful for detection and/or quantification of NEK10 protein. Assays that rely on a chromogenic substrate can also be useful for the detection and/or quantification of NEK10 protein.

III. Identification of Activators of NEK10

Aspects of the present disclosure provide methods for screening and identifying compounds (e.g., chemical compounds and/or biological compounds) that are therapeutically useful for a subject having a respiratory disorder, which can be a subject having a mutation in NEK10 such as those described herein (e.g., NEK10$^{G>C}$).

In some embodiments, compounds for use in screening methods described herein include small molecule libraries such as commercially available small molecule libraries. Small molecules can have a molecular weight of about any of 100 to 20,000 daltons, 500 to 15,000 daltons, or 1000 to 10,000 daltons.

Screening methods described herein involve identifying compounds capable of compensating for a defect associated with a respiratory disorder and/or a NEK10 mutation. Such defects include, but are not limited to, reduced NEK10 expression, reduced mucociliary transport (MCT), reduced maximal particle transport velocity, reduced ciliary length, thinning of the periciliary liquid layer (PCL), reduced kinase activity, or a combination thereof. In some examples, screening methods described herein involve identifying compounds capable of increasing NEK10 activity (e.g., NEK10 kinase activity) and/or NEK10 expression.

In some embodiments, to practice the screening methods described herein, compounds (e.g., small molecule libraries) can be screened against NEK10 (e.g., wild-type NEK10 or NEK10 mutant) to identify those capable of increasing NEK10 activity (e.g., NEK10 kinase activity). In such instances, NEK10 can be purified NEK10 or NEK10 expressed in cells (e.g., cells having endogenous expression and/or engineered expression of NEK10).

In some embodiments, compounds (e.g., small molecule libraries) can be screened against wild-type or mutant NEK10 cells (e.g., whole cells or cell lysates) to identify those having potential therapeutic effects for subjects having respiratory disorders such as a subject having a mutation in NEK10.

For example, when identifying a compound capable of potentiating mucociliary transport (MCT), methods provided herein comprise contacting mutant NEK10 cells with a candidate compound, and detecting mucociliary transport (MCT) using any suitable method such as those described herein. If the candidate compound increases mucociliary transport (MCT) relative to that in the absence of the candidate compound, then the candidate compound can be identified as a potential therapeutic agent capable of potentiating mucociliary transport (MCT). Alternatively, or in addition to, if the candidate compound increases mucociliary transport (MCT) in mutant NEK10 cells relative to that in wild-type cells (e.g., wild-type cells in the absence of the candidate compound), then the candidate compound can be identified as a potential therapeutic agent capable of potentiating mucociliary transport (MCT).

Any suitable cells (e.g., human bronchial epithelial cells (HBECs) at an air-liquid interface (ALI)) can be used in screening methods described herein. Suitable cells include those carrying a wild-type NEK10 gene or those carrying a mutant NEK10 gene (e.g., cells carrying NEK10$^{G>C}$). In some examples, cells having a mutant NEK10 gene are cells transfected with nucleic acids comprising the mutant NEK10 gene. In other examples, cells having a mutant NEK10 gene are obtained from a subject carrying the mutant NEK10 gene.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described may be more fully understood, the following examples are set forth. The examples described in this application are offered to illustrate the methods and compositions provided herein and are not to be construed in any way as limiting their scope.

Materials and Methods

The following materials and methods were used in the Examples set forth herein.

Whole Exome Sequencing and Clinical Phenotyping

Clinical WES was performed on kindreds 1-3 by the Molecular Diagnostics Laboratory of the King Faisal Specialist Hospital and Research Center (KFSHRC). Exome enrichment was performed using the Agilent SureSelect Target Enrichment workflow prior to high-throughput sequencing on the Illumina HiSeq 2500 system. Greater than 30× coverage of 95% of the target regions was obtained for all samples. Exome sequences were mapped to the UCSC hg19 reference sequence with a custom pipeline and interrogated for variants incorporating databases customized to Arab populations. Sequencing of proband siblings and additional kindreds was performed under a protocol approved by the KFSHRC IRB (REC #2121053). Sequencing and analysis of kindred 4 was performed under a protocol approved by University Children's Hospital Muenster IRB AZ 2015-104-f-S. Sequencing and analysis of kindred 5 was performed under a protocol approved by UNC Chapel Hill IRBs 05-2979 and 13-2348.

Human Bronchial Epithelial Cell (HBEC) and Air-Liquid Interface (ALI) Tissue Culture Control human samples were obtained from discarded lung allografts under a protocol approved by the Partners Human Research Committee (IRB #2012P001079). Proband samples were obtained at the time of bilateral lung transplantation under a protocol approved by the Partners Human Research Committee (IRB #2013P002332) with informed consent obtained prior to organ explantation. Airway cells were obtained as previously described (Neuberger T, Burton B, Clark H & Van Goor F in Cystic Fibrosis 39-54 (Humana Press, 2011)). Briefly, bronchial tube sections were rinsed in MEM supplemented with DTT and DNAse I prior to overnight incubation in MEM supplemented with pronase, DNAse I, antibiotics, and antifungals. Epithelial sheets were further dissociated with Accutase and plated into PneumaCult Ex-Plus expansion media (StemCell Technologies #05040). All plates were pre-coated with sterile-filtered, laminin-rich conditioned media (DMEM+10% FBS) of the 804G rat bladder cell line to promote HBEC adhesion. HBECs were used between passage 2 and 5 for experiments and were dissociated for sub-culturing with TrypLE Select (Gibco 12563011). ALI cultures were established using 24-well (Corning 3470) or 6-well (Corning 3412) plates coated with 804G-conditioned media. At confluence, apical media was removed and basolateral media was changed to PneumaCult ALI (StemCell Technologies #05001) for 4 to 6 weeks of differentiation ("mature ALI"), except where stated otherwise. Media was exchanged every 48 hours and cultures were washed with PBS weekly beginning on ALI day 14 on a plate shaker at 600 rpm×2.

Quantitative Reverse Transcription Polymerase Chain Reaction (qRT-PCR)

Total RNA was extracted with Trizol reagent (Invitrogen) according to the manufacturer's protocol before first strand cDNA synthesis with the SuperScript VILO system (Invitrogen). Quantitative PCR was performed using PowerUp SYBR Green reagent (ABI) on an ABI QuantStudio6 instrument. All analyses were performed with standard curve-based quantitation and normalization to 18S rRNA abundance. 2-tailed Student's t-test was performed for analysis of statistical significance. qRT-PCT primer sequences available in Table 1 and were designed using Primer3Plus software to span exon-exon junctions in all cases.

TABLE 1

Oligonucleotide Primers.

| SEQ ID NO | Sequence | Name | Application |
|---|---|---|---|
| 2 | AGCCTGTCCAGTGCAAATG | NEK10 upstream Fwd | qRT-PCR |
| 3 | GGCATTGGTGTCATTGAGC | NEK10 upstream Rvs | qRT-PCR |
| 4 | GCATGAATCCACAGAAGCTG | NEK10 5' Fwd | qRT-PCR |
| 5 | TACGCTGAGGATGTTTGCTG | NEK10 5' Rvs | qRT-PCR |
| 6 | GAGCCCAACTTTTTCACAGC | NEK10 3' Fwd | qRT-PCR |
| 7 | CCAATTCAATGCTGGTTGG | NEK10 3' Rvs | qRT-PCR |
| 8 | TCAGTGGAGAAGGAGTTGGAC | KRT5 Fwd | qRT-PCR |
| 9 | CTGCCATATCCAGAGGAAACAC | KRT5 Rvs | qRT-PCR |

TABLE 1-continued

Oligonucleotide Primers.

| SEQ ID NO | Sequence | Name | Application |
|---|---|---|---|
| 10 | CCAAAAGCCCAGAGAAAGC | SCGB1A1 Fwd | qRT-PCR |
| 11 | AGTTGGGGATCTTCAGCTTC | SCGB1A1 Rvs | qRT-PCR |
| 12 | TGGATCACGGACAACTTCTG | FOXJ1 Fwd | qRT-PCR |
| 13 | GAGGCACTTTGATGAAGCAC | FOXJ1 Rvs | qRT-PCR |
| 14 | GCTCTTTGAGTTGATGCCTGTC | DNAH5 Fwd | qRT-PCR |
| 15 | CAGCGGCAATGTAGTTCAAG | DNAH5 Rvs | qRT-PCR |
| 16 | AGACAAATCGCTCCACCAAC | 18S Fwd | qRT-PCR |
| 17 | CCTGCGGCTTAATTTGACTC | 18S Rvs | qRT-PCR |
| 18 | TCTGGGGCATTGATGTTTTACA | NEK10 full length cDNA Fwd | cloning |
| 19 | CCCCATGGCATCTTGGTCTT | NEK10 full length cDNA Rvs | cloning |
| 20 | GTTCCCCAGAACGAACGGAT | FOXJ1 promoter Fwd | cloning |
| 21 | CATGTCTGCGGGGACTCTC | FOXJ1 promoter Rvs | cloning |
| 22 | GCCCGGCACAAAATTAAGCA | NEK10 promoter Fwd | cloning |
| 23 | GATGCAGAGGAAGCAGCAGT | NEK10 promoter Rvs | cloning |
| 24 | CACCGGTCTGAGCCCGCCATCAGGG | sgNEK10a oligo 1 | cloning |
| 25 | AAACCCCTGATGGCGGGCTCAGACC | sgNEK10a oligo 2 | cloning |
| 26 | CACCGGCGGGTGGACACAGAGCTCG | sgNEK10b oligo 1 | cloning |
| 27 | AAACCGAGCTCTGTGTCCACCCGCC | sgNEK10b oligo 2 | cloning |
| 28 | CACCGGCTGCTCTTCTCCATAGCCG | sgNEK10c oligo 1 | cloning |
| 29 | AAACCGGCTATGGAGAAGAGCAGCC | sgNEK10c oligo 2 | cloning |
| 30 | TTCCAGCCCAAGTGCAAAGA | NEK10 c.2317C>T sequencing amplicon Fwd | PCR |

TABLE 1-continued

Oligonucleotide Primers.

| SEQ ID NO | Sequence | Name | Application |
|---|---|---|---|
| 31 | TGATGAATGTTCCTTAAAACAAGCA | NEK10 c.2317C>T sequencing amplicon Rvs | PCR |

Immunoblotting

Protein lysates were prepared in lysis buffer containing 1% Triton X-100, 10 mM β-glycerol phosphate, 10 mM pyrophosphate, 40 mM HEPES pH 7.4, 2.5 mM $MgCl_2$, and one mini tablet of EDTA-free protease inhibitor (Roche) per 10 mL. Lysates were subjected to SDS-PAGE electrophoresis and transferred to PVDF membranes before immunoblotting with the indicated antibodies. Primary antibodies and working dilutions were as follows: rabbit anti-NEK10 (Sigma HPA038941, lot R35857, 1:1000), mouse anti-NEK10 (Sigma WH0152110M1, lot 09058-1C9, 1:1000), rabbit anti-GAPDH (Abcam ab9485, 1:2500), mouse anti-FLAG M2 (Sigma F1804, lot SLBS3530V, 1:1000), rabbit anti-Raptor (Millipore 09-217, lot 3236353, 1:1000), mouse anti-β-actin (Santa Cruz sc-47778, lot K1718, 1:1000), mouse anti-acetylated α-tubulin (Sigma T7451, 1:1000). Secondary antibodies and dilutions were as follows: HRP-conjugated anti-rabbit IgG (Cell Signaling Technologies #7074, 1:3000), HRP-conjugated anti-mouse IgG (Cell Signaling Technologies #7076, 1:3000).

NEK10 cDNA Cloning

Total RNA was extracted with Trizol reagent according to the manufacturer's protocol before reverse transcription with the SuperScript IV system (Invitrogen) using oligo-dT priming. Full-length NEK10 cDNAs were amplified with Platinum SuperFi polymerase (Invitrogen), cloned into pCR-Blunt II-TOPO (Invitrogen) according to the manufacturer's protocol, and individual clones sequenced completely. Consensus control and NEK10G>C sequences cloned from each genotype were utilized for further experiments as indicated in the text. Cloning primers available in Table 1.

Linkage Analysis

Genomic DNA was extracted from whole blood using a standard protocol. Genome-wide genotypes were obtained using an Affymetrix Axiom SNP Chip platform (Affymetrix, Santa Clara, CA) following the manufacturer's instructions. Blocks of homozygosity were identified using AutoSNPa (dna.leeds.ac.uk/autosnpa/). Linkage analysis was performed on the SNP genotypes using the Allegro component of EasyLinkage software (Hoffmann K & Lindner T H easyLINKAGE-Plus-automated linkage analyses using large-scale SNP data. *Bioinformatics* 21, 3565-3567 (2005)). Statistical significance was assessed using a genome-wide LOD threshold of 3.3, corresponding to a type I error of 5%.

Immunofluorescence Microscopy (IF)

ALI samples were washed in PBS, fixed for 15 minutes in 4% paraformaldehyde (PFA), washed thrice in PBS, and cut free from their plastic supports. For centrin staining only, samples were fixed instead in ice-cold methanol for 15 minutes at −20° C. but otherwise processed identically. ALI membranes were then blocked (5% donkey serum+0.3% Triton X-100) for 1 hour at room temperature before incubation with the indicated primary antibodies overnight at 37°

C. in dilution buffer (1% BSA+0.3% Triton X-100). Membranes were washed 4 times in wash buffer (PBS+0.1% Triton X-100) before probing with fluorophore conjugated secondary antibodies for 1 hour at 37° C. in dilution buffer. DAPI was added to the secondary antibody solution for nuclear counterstaining. Membranes were washed 4 additional times in wash buffer and once in PBS before mounting in Fluoromount-G (Southern Biotech). Confocal images were obtained with an Olympus FV10i confocal laser-scanning microscope with a 60× oil objective.

The following primary antibodies were used: mouse anti-acetyl-α-tubulin (Sigma T6793, 1:1000), mouse anti-MUC5AC (ThermoFisher MS-145, lot 145p1709c, 1:500), goat anti-CCSP (gift from B. Stripp, no lot data (non-commercial), 1:5000), chicken anti-KRT5 (Biolegend 905901, 1:500), rabbit anti-CETN1 (gift from I. Cheeseman, no lot data (non-commercial), 1:5000), rabbit anti-VANGL1 (Sigma HPA025235, lot c101664, 1:500). All secondary antibodies were Alexa Fluor conjugates used at 1:500 dilution (Life Technologies): gt anti-chicken 488 (A-11039, lot 1599396), dk anti-mouse 488 (A-21202, lot TF271737), dk anti-rabbit 488 (A-21206, lot TI271741), dk anti-mouse 594 (R37115), dk anti-rabbit 594 (R37119, lot TI271728).

Assessment of SCGB1A1-, MUC5AC-, and acetyl-α-tubulin-positive area was performed using automated scripts for object segmentation in ImageJ using the FIJI implementation (Schindelin J et al. Fiji: an open-source platform for biological-image analysis. *Nat. Methods* 9, 676-682 (2012)) and null hypothesis testing was performed using the 2-tailed Student's t-test. KRT5-positive area could not be quantitated as basal cells form an essentially contiguous layer. Centrin puncta were quantitated using automated scripts in ImageJ/FIJI which counted local maxima within ciliated cells. Basal body density was then calculated by dividing total puncta by cell number. Source code for scripts available on request. Null hypothesis testing was performed using the 2-tailed Student's t-test.

Lentivirus Cloning, Production, and HBEC Infection

NEK10:eGFP and FOXJ1:eGFP vectors were generated by amplifying the respective promoter regions from human genomic DNA and, using NEBuilder Gibson assembly (New England Biolabs), replacing the existing CMV promoter of the pLJM1 construct (Addgene #19319). The putative NEK10 promoter was identified as a conserved ~1.6 kb region bounding the NEK10 transcription start site and harboring epigenetic marks consistent with promoter function. The FOXJ1 promoter sequence was cloned using a previously described (Ostrowski et al. Targeting expression of a transgene to the airway surface epithelium using a ciliated cell-specific promoter. *Mol. Ther* 8, 637-645 (2003)) region as a guide. Gibson assembly was also used to generate FOXJ1 promoter-driven lentiviral expression vectors by replacing the pLJC2 vector (Addgene #87974) CMV promoter. NEK10 mutants were generated using a site-directed mutagenesis strategy followed by Gibson assembly into the aforementioned FOXJ1-driven expression vectors. Cas9/sgRNA-expressing lentiviral vectors were generated using the pLentiCRISPRv2 vector (Addgene #52961). Briefly, guide RNAs targeting NEK10 or the AAVS1 control locus were selected from our previously published (Wang T et al. Identification and characterization of essential genes in the human genome. Science 350, 1096-1101 (2015)) guide library (Addgene #1000000100), synthesized from annealed DNA oligonucleotides, cloned into BsmbI-digested pLentiCRISPRv2 vector, screened, and sequenced to confirm identity. Cloning primers available in Table 1.

Lentiviruses were produced as follows: HEK293T cells were transfected with lentiviral constructs and viral packaging plasmids psPAX2 (Addgene #12260) and pCMV-VSVG (Addgene #8454) using the X-tremeGeneHP reagent (Sigma). Viral supernatants were harvested and concentrated using the Lenti-X concentrator system (Takara) prior to use for HBEC infection. Low-passage HBECs were infected with concentrated lentivirus and, 48 h later, selected with 1 µg/ml puromycin for an additional 48 hours before ALI culture seeding.

Fluorescence-Activated Cell Sorting (FACS)

Mature ALI cultures were washed with PBS and incubated in TrypLE Select (Gibco) for 1 hour at 37° C. to liberate single cells. Cells were strained through a 70 um cell strainer to remove clumps and debris, washed in 1×PBS, and resuspended in a buffer containing 1% FBS, 1 mM EDTA, and 25 mM HEPES. Sorting was performed using a BD FACS Aria (BD Biosciences) running FACS Diva software and analysis was performed using FlowJo (version 10) software. GFP-positive cells were sorted after gating (FIG. 6I) on viable (by exclusion of vital dye) singlets (by FSC/SSC) and harvested for RNA isolation in Trizol.

ALI Live Phase Contrast Imaging

Mature ALI transwells were removed from their media to glass-bottomed tissue culture dishes and imaged under 40× objective magnification with phase contrast optics at 30 frames per second for a total of 300 frames using a Zeiss Z1 AxioObserver inverted microscope. The resulting 8-bit monochrome videos were processed in ImageJ/FIJI as follows: each 300 frame stack was duplicated and a new 299 frame stack (the "difference stack") generated by subtracting the (n+I)th frame from the nth frame. The mean of every pixel in the difference stack was then calculated and the resultant data output to a single TIF file visually representing the average pixel intensity change over the course of video, a surrogate for motion. This TIF file was pseudocolored using the "fire" lookup table to yield the final processed images. Data collected in a single experimental imaging session is displayed with identical brightness/contrast thresholds to allow direct visual comparison between experimental conditions. Source code for scripts available on request. For quantitation, mean intensity of TIF files were extracted in ImageJ, normalized per imaging session, and reported as relative intensity levels. Null hypothesis testing was performed using the 2-tailed Student's t-test.

Micro-Optical Coherence Tomography (µOCT)

µOCT was performed and analyzed as previously described (Liu L et al. Method for Quantitative Study of Airway Functional Microanatomy Using Micro-Optical Coherence Tomography. PLoS ONE 8, e54473 (2013); and Liu L et al. Imaging the subcellular structure of human coronary atherosclerosis using micro-optical coherence tomography. Nat. Med 17, 1010-1014 (2011)). In brief, periciliary liquid layer (PCL) depth and ciliary beat frequency (CBF) were directly assessed via cross-sectional images of the airway epithelium with high resolution (~1 µm) and high acquisition speed (20,480 Hz A-line rate resulting in 40 frames/s at 512 A-lines per frame across 1 mm lateral range). Quantitative analysis of images was performed in FIJI/ImageJ. To establish CBF, previously published custom code in Matlab (Mathworks) was used to quantify Fourier-transformed reflectance modulations of beating cilia. PCL depth was characterized directly by geometric measurement of the respective layers. For measurement of mucociliary transport (MCT), native mucus was washed away completely with PBS and 0.5 µm polystyrene beads (Invitrogen F8813) were added to the apical ALI surface prior to imaging. Particle tracking was performed using MosaicSuite in ImageJ (Sbalzarini I F & Koumoutsakos P Feature point tracking and trajectory analysis for video imaging in cell biology. J. Struct. Biol 151, 182-195 (2005)) and the resulting particle tracks analyzed in Matlab. Particles included for analysis were within 90 µm of the epithelial surface, present for at least 20 frames (0.5 s), and had a velocity vector within 10° of horizontal. Hypothesis testing was performed by Mann Whitney U-test or, when necessary to control for environmental (temperature, humidity, etc.) and instrument changes between imaging sessions, by linear mixed effects model.

Imaging Flow Cytometry

Single cells were generated from mature ALI as above, fixed in 2% PFA, and resuspended in PBS before analysis on an ImageStreamX MkII instrument (Amnis). The gating strategy was as follows: Starting with unclipped events using a centroid X gate, in-focus cells were obtained using a gradient RMS gate. Next, a liberal area vs. aspect ratio gate (R1) was employed to exclude clumps, followed by an area vs. GFP intensity plot to gate on GFP+ cells (R2), followed by a GFP morphology mask vs aspect ratio gate (R3) to exclude GFP doublets, and followed again by a final doublet removal step again gated on brightfield (R4). Finally, cells were gated on R6, cells with a minimal mean pixel value of 45 in the GFP channel. This strategy yielded 4,108 imaged single cells from NEK10WT and 3,513 imaged single cells from NEK10$^{G>C}$ ALI samples. From this parent population of unclipped, singlet, in-focus, GFP-positive cells we defined masks of whole cells and GFP-positive cell bodies. Major axis difference was calculated by subtracting the major axis of the GFP mask from the whole cell mask, and area difference was likewise calculated by subtracting the GFP mask area from the whole cell mask area. Null hypothesis testing was performed using the 2-tailed Student's t-test. For gallery images, we selected representative images centered on the medians of the indicated populations.

Clinical Histopathology

Age-matched patients who underwent pneumonectomy (cases 1-3) or lobectomy (case 4) at Massachusetts General Hospital between 2018-2019 were identified and their H&E stained clinical slides photographed in compliance with IRB 2016P001475. Well-preserved and well-oriented airway was photographed at 400× magnification and processed identically for all panels.

Scanning, Scanning/Transmission Electron Microscopy (SEM, STEM), Negative Stain EM ALI cultures were washed in PBS, fixed in 2% PFA/2.5% glutaraldehyde/0.1M sodium cacodylate for 15 minutes at room temperature, fixed in fresh fixative for 1 hour at 4° C., washed thrice in 0.1M sodium cacodylate, dehydrated, then sputter coated with gold. SEM images were acquired on a Zeiss Crossbeam 540 using secondary electron imaging. STEM samples were prepared identically before resin embedding, ultrathin section cutting, and imaging on a Zeiss Crossbeam 540 operating in STEM mode. For negative stain EM, samples were adsorbed onto 200 mesh carbon film copper grids for 1 min, rinsed for 30 sec with distilled water, then stained with 2% uranyl acetate for 1 min, again washed with distilled water, and imaged on a Zeiss Crossbeam 540. Resultant micrographs were analyzed in FIJI/ImageJ where individual cilia were measured; null hypothesis testing was performed using the 2-tailed Student's t-test.

Ciliary Isolation

Cilia were purified according to a previously published protocol with minor modifications (Ostrowski L E in Cell Biology (ed. Celis J E) 99-102 (Elsevier, 2005)). Mature ALI cultures were washed thrice in PBS before the addition of pre-chilled deciliation buffer (10 mM Tris pH 7.5, 50 mM NaCl, 10 mM CaCl$_2$, 1 mM EDTA, 7 mM β-mercaptoethanol, 0.1% Triton X-100, 1× Roche completeMINI protease inhibitor cocktail) and 1 minute of vigorous rocking at 4° C. Supernatants, containing cilia, were removed to pre-chilled 1.5 mL tubes and a second aliquot of deciliation buffer applied for 1 minute. Supernatants were then pooled and centrifuged 1 min at 1000×g to pellet debris. Supernatants were carefully removed and centrifuged 5 min at 12,000×g to pellet axonemes. Ciliary preparations were resuspended in chilled resuspension buffer (300 mM HEPES pH 7.3, 250 mM NaCl, 50 mM MgSO$_4$, 10 mM EGTA, 1 mM EDTA, 10 mM DTT, 1× Roche completeMINI protease inhibitor cocktail) before use for EM or immunoblotting. De-ciliated ALI cultures were harvested in lysis buffer (composition as above) and used for immunoblotting.

Phosphoproteomics and Analysis

ALI cultures were grown to maturity, washed in PBS, and lysed in urea lysis buffer containing: 20 mM HEPES (pH 8.0), 9.0 M urea, 1 mM sodium orthovanadate (activated), 2.5 mM sodium pyrophosphate, and 1 mM β-glycerolphosphate. Lysates were protease-digested prior to phosphopeptide enrichment using immobilized metal ion affinity chromatography (Fe-IMAC). Eluted peptides were then subjected to LC-MS/MS Analysis using an Orbitrap-Fusion Lumos (ESI-HCD dissociation) and the resulting spectra analyzed with the Thermo Scientific Proteome Discoverer implementation of the SEQUEST algorithm (Eng J K, McCormack A L & Yates J R An approach to correlate tandem mass spectral data of peptides with amino acid sequences in a protein database. *J Am Soc Mass Spectrom* 5, 976-989 (1994)). Each biological sample was run in duplicate injections. Searches were performed against the most recent update of the Uniprot *Homo sapiens* database with mass accuracy of +/−50 ppm for precursor ions and 0.02 Da for product ions. Results were filtered with mass accuracy of +/−5 ppm on precursor ions and presence of the intended motif. This dataset yielded 56,540 redundant modified peptide assignments to 14,805 modified sites. Data were normalized by median offset correction based on all the relative abundance values in the data set and expressed as log$_2$ fold changes for analysis. Publicly available data sets were used to establish gene lists for the motile ciliary proteome (Ostrowski L E et al. A Proteomic Analysis of Human Cilia Identification of Novel Components. *Mol Cell* Proteomics 1, 451-465 (2002)), PCD genes (MD MRK, PhD MZ & MD ML Primary Ciliary Dyskinesia. *Clinics in Chest Medicine* 37, 449-461 (2016)) (with Online Mendelian Inheritance in Man, OMIM®. Johns Hopkins University, Baltimore, MD MIM Number: 244400: 05/30/2019.omim.org/), non-PCD ciliopathy genes48, axonemal dyneins and assembly factors (HGNC sets "Dyneins, axonemal" and "Axonemal dynein assembly factors"), kinesins (HGNC set "Kinesins"), intraflagellar transport (Ishikawa H & Marshall W F Ciliogenesis: building the cell's antenna. *Nat Rev Mol Cell Biol* 12, 222-234 (2011)), radial spoke apparatus (HGNC RSPH gene family), central pair complex (Teves et al. Mammalian axoneme central pair complex proteins: Broader roles revealed by gene knockout phenotypes. *Cytoskeleton* 73, 3-22 (2016); Osinka et al. Ciliary Proteins: Filling the Gaps. Recent Advances in Deciphering the Protein Composition of Motile Ciliary Complexes. *Cells* 8, 730 (2019); and Zhao et al. Proteome of the central apparatus of a ciliary axoneme. *J Cell Biol* 218, 2051-2070 (2019)), and ciliary length control (Tammana et al. Centrosomal protein CEP104 (*Chlamydomonas* FAP256) moves to the ciliary tip during ciliary assembly. *J Cell Sci* 126, 5018-5029 (2013); Niwa et al. KIF19A Is a Microtubule-Depolymerizing Kinesin for Ciliary Length Control. *Dev. Cell* 23, 1167-1175 (2012); Lai et al. Functional characterization of putative cilia genes by high-content analysis. *Molecular Biology of the Cell* 22, 1104-1119 (2011); Vasudevan et al. Kinesin-13 regulates the quantity and quality of tubulin inside cilia. *Molecular Biology of the Cell* 26, 478-494 (2015); Piao et al. A microtubule depolymerizing kinesin functions during both flagellar disassembly and flagellar assembly in *Chlamydomonas*. *Proc. Natl. Acad Sci*. U.S.A 106, 4713-4718 (2009); Wang et al. Flagellar regeneration requires cytoplasmic microtubule depolymerization and kinesin-13. *Journal of Cell Science* 126, 1531-1540 (2013); and Broekhuis et al. Regulation of Cilium Length and Intraflagellar Transport by the RCK-Kinases ICK and MOK in Renal Epithelial Cells. *PLoS ONE* 9, e108470 (2014)). Gene ontology (GO) analysis was performed using published methods (Ashburner et al. Gene Ontology: tool for the unification of biology. *Nat Genet* 25, 25-29 (2000); and The Gene Ontology Consortium. The Gene Ontology Resource: 20 years and still GOing strong. *Nucleic Acids Res* 47, D330-D338 (2019)) utilizing the PANTHER overrepresentation test against the GO Ontology database (2019-10-08 release) and the "GO Biological Process Complete" annotation data set via publicly-available online interface.

Statistics and Reproducibility

Figure 1C:
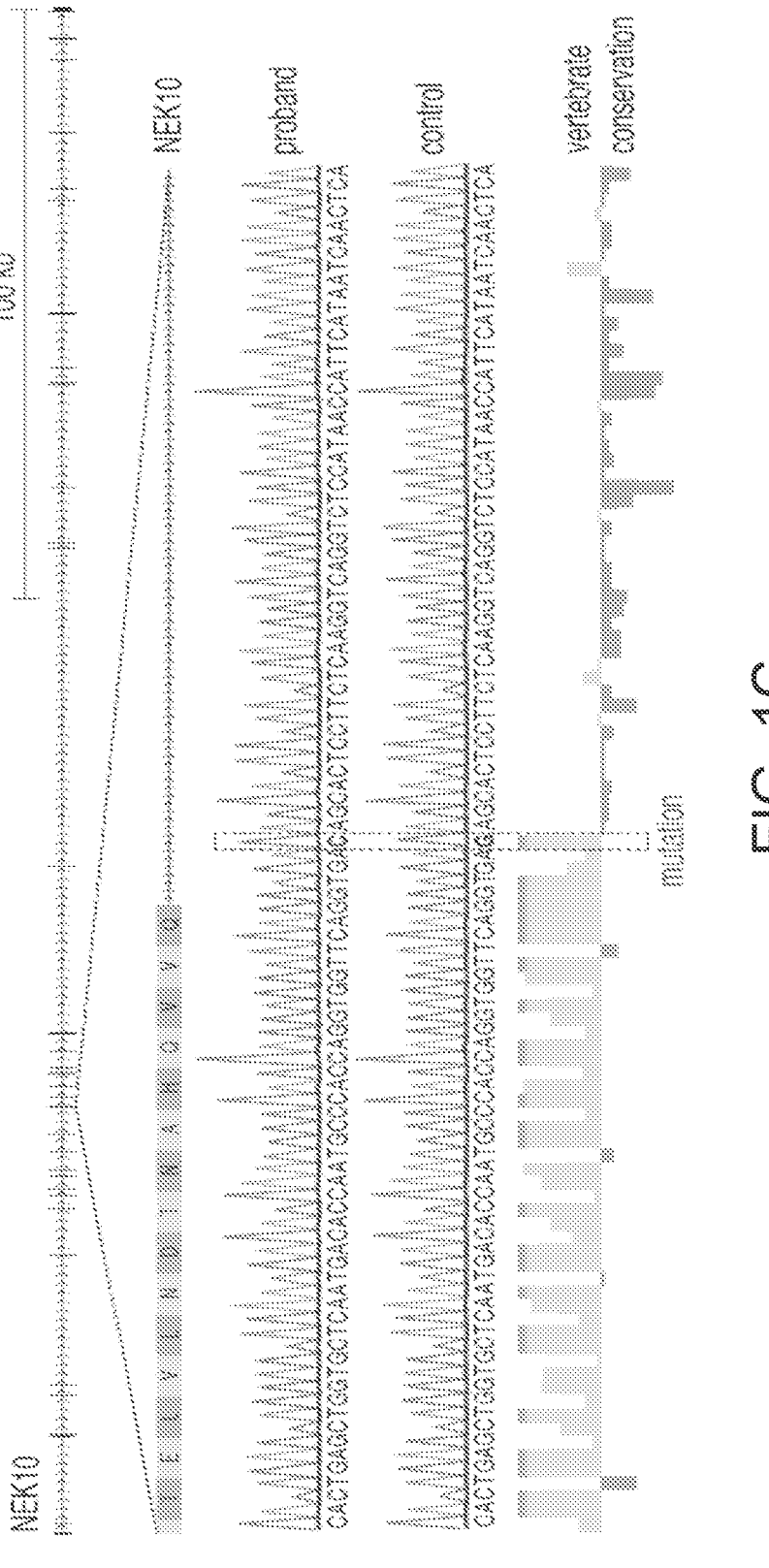
Figure 1D:
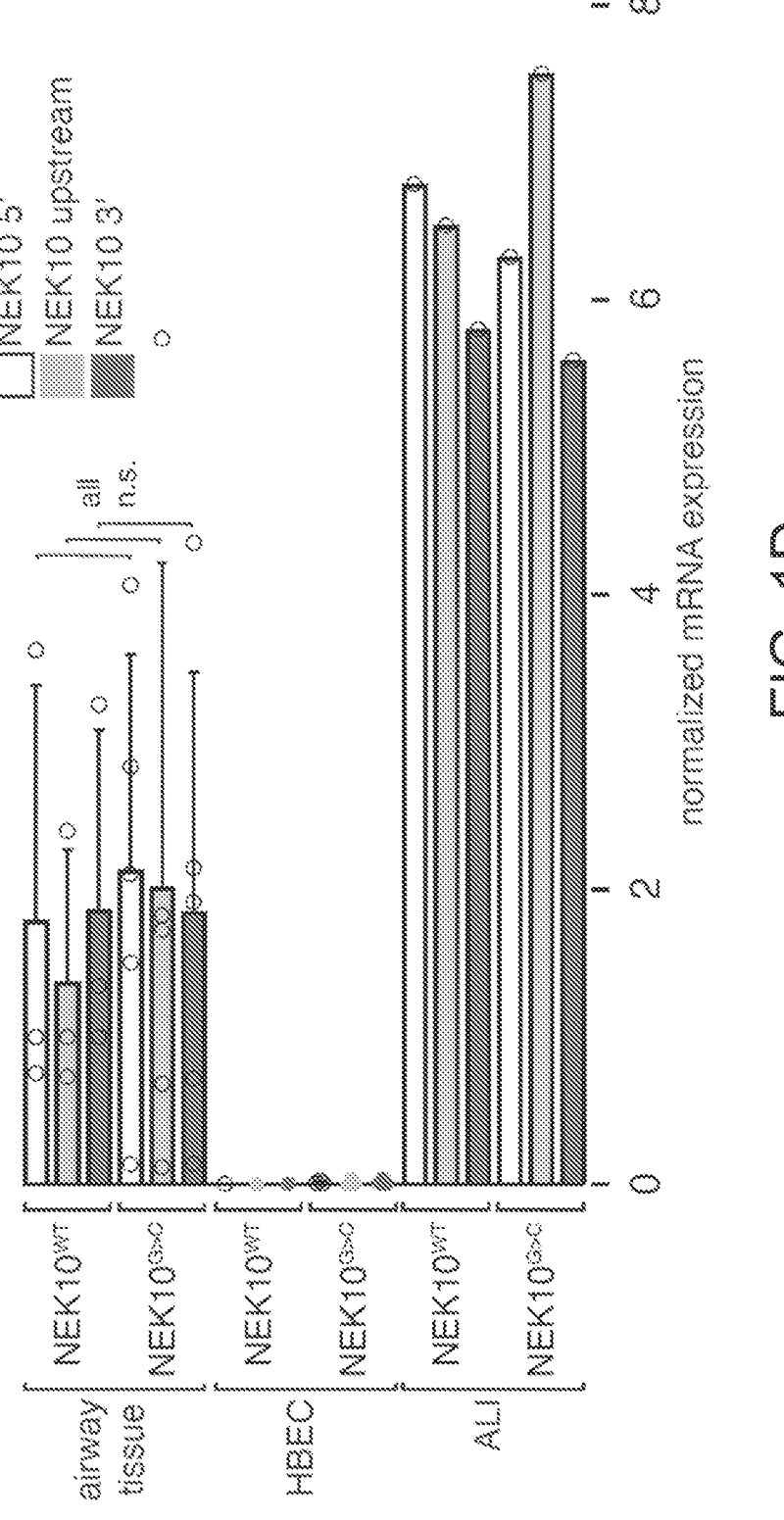
Figure 2A:
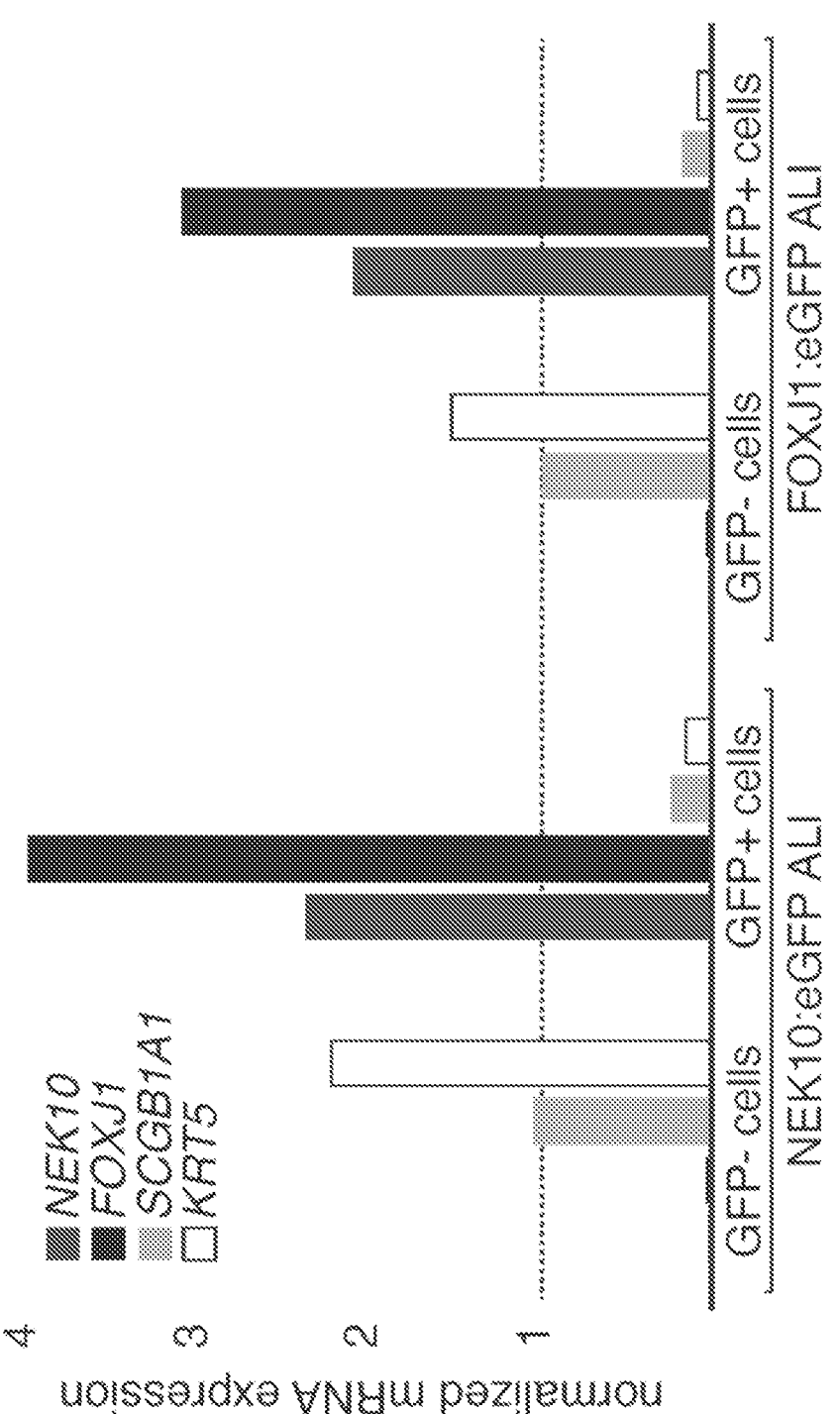
Figure 2D:
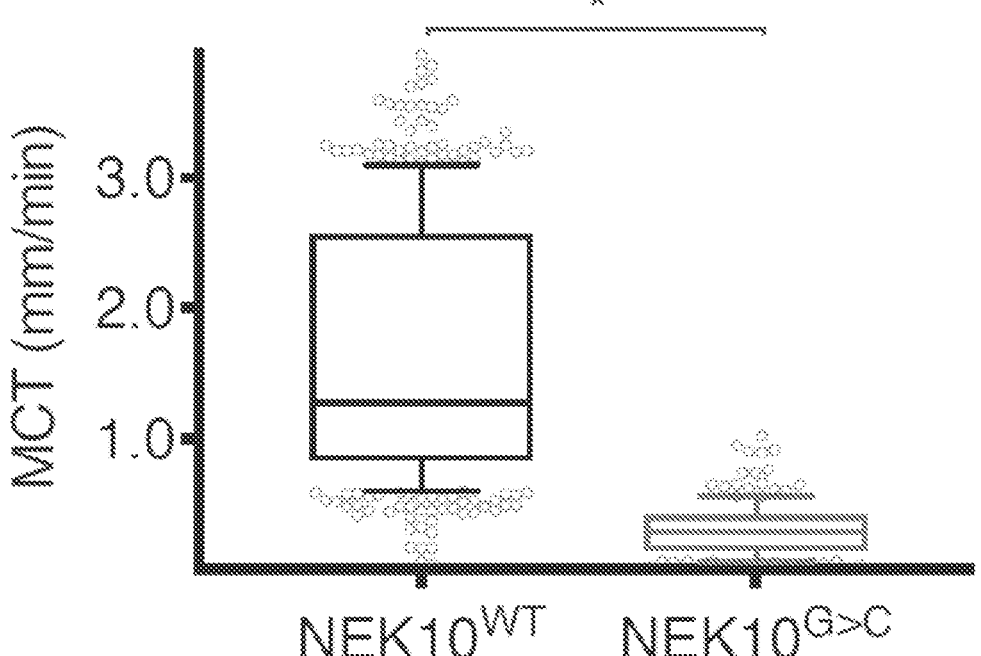
Figure 2E:
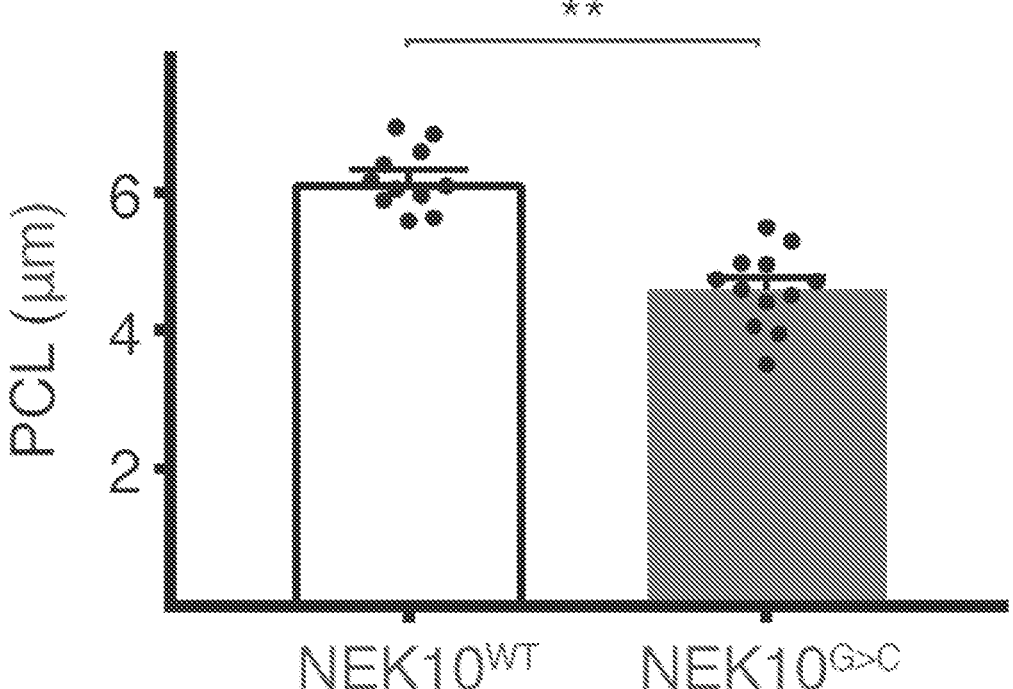
Figure 2G:
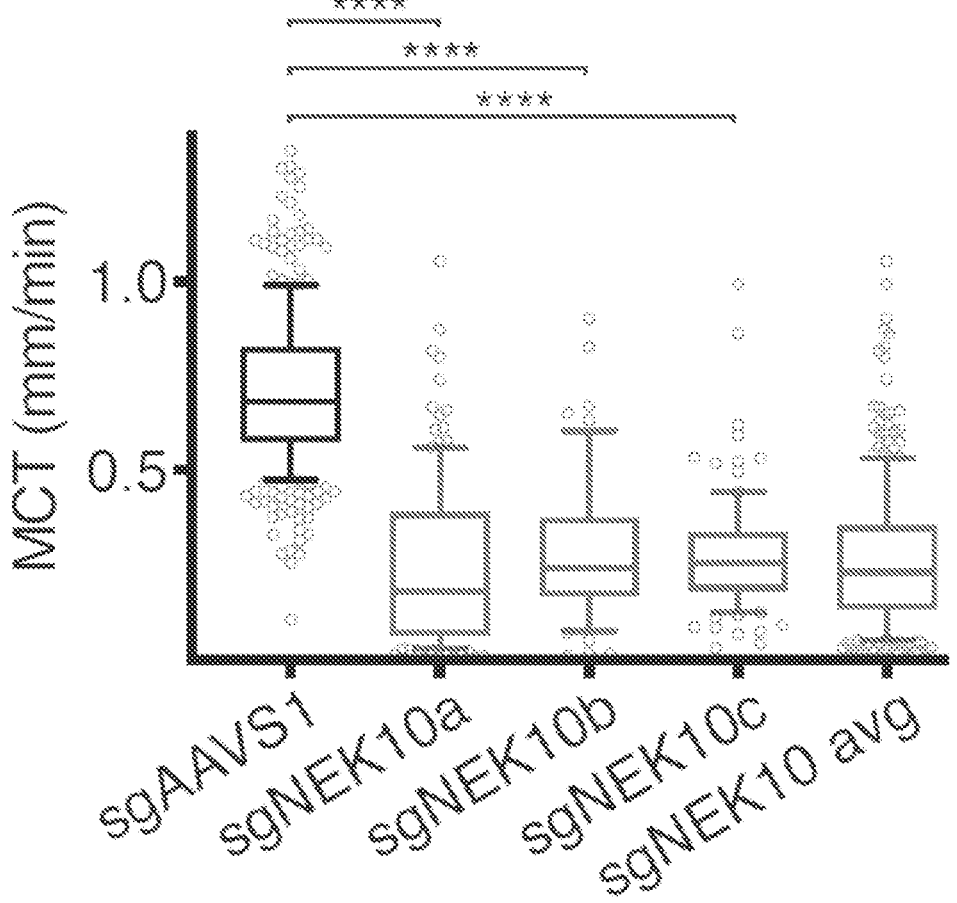
Figure 2H:
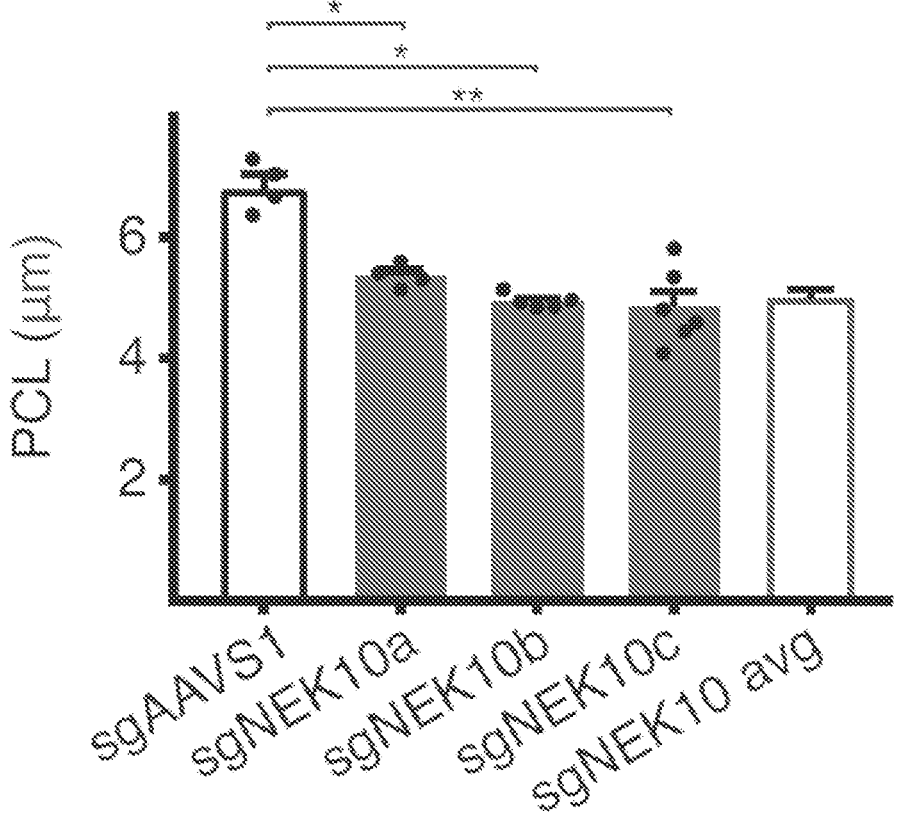
Figure 2I:
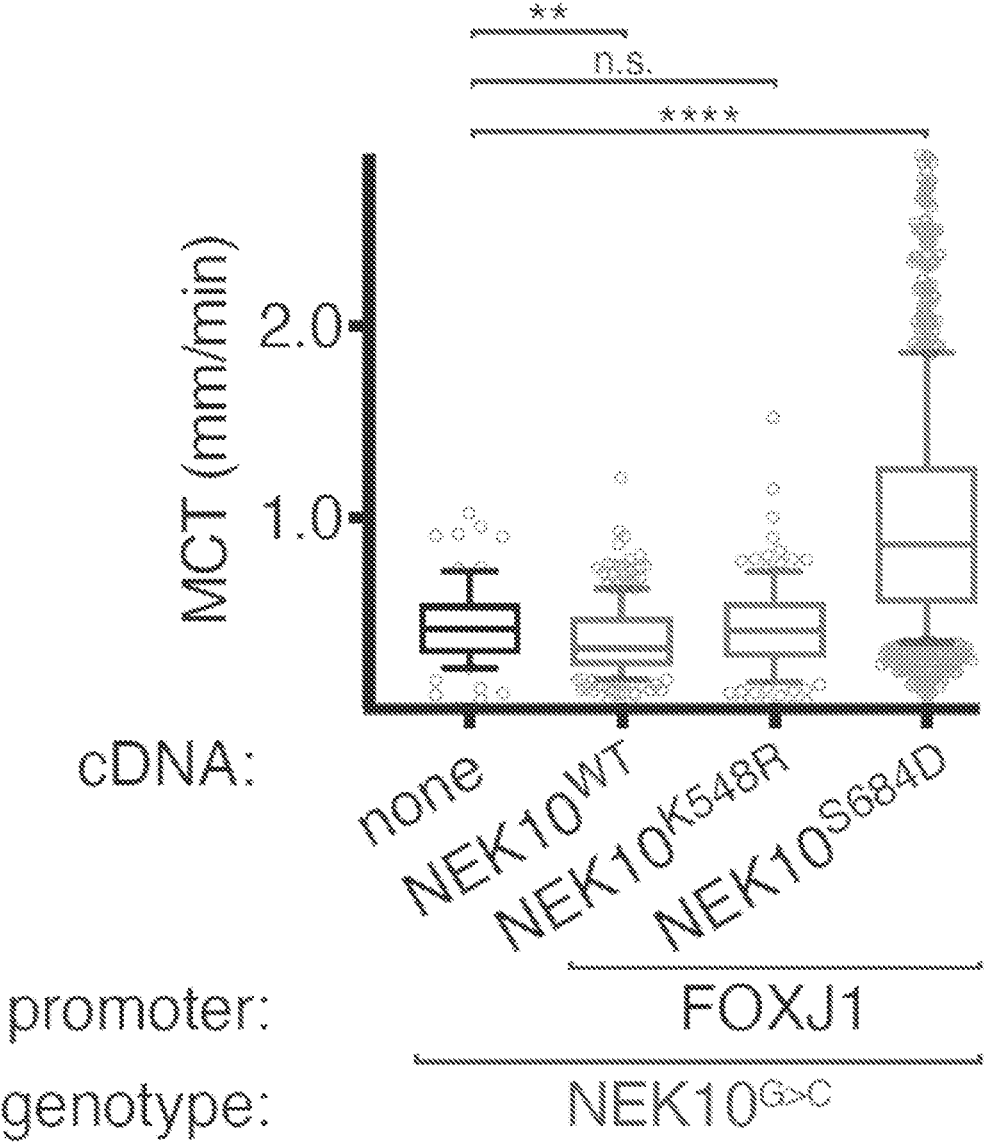
Figure 3A:
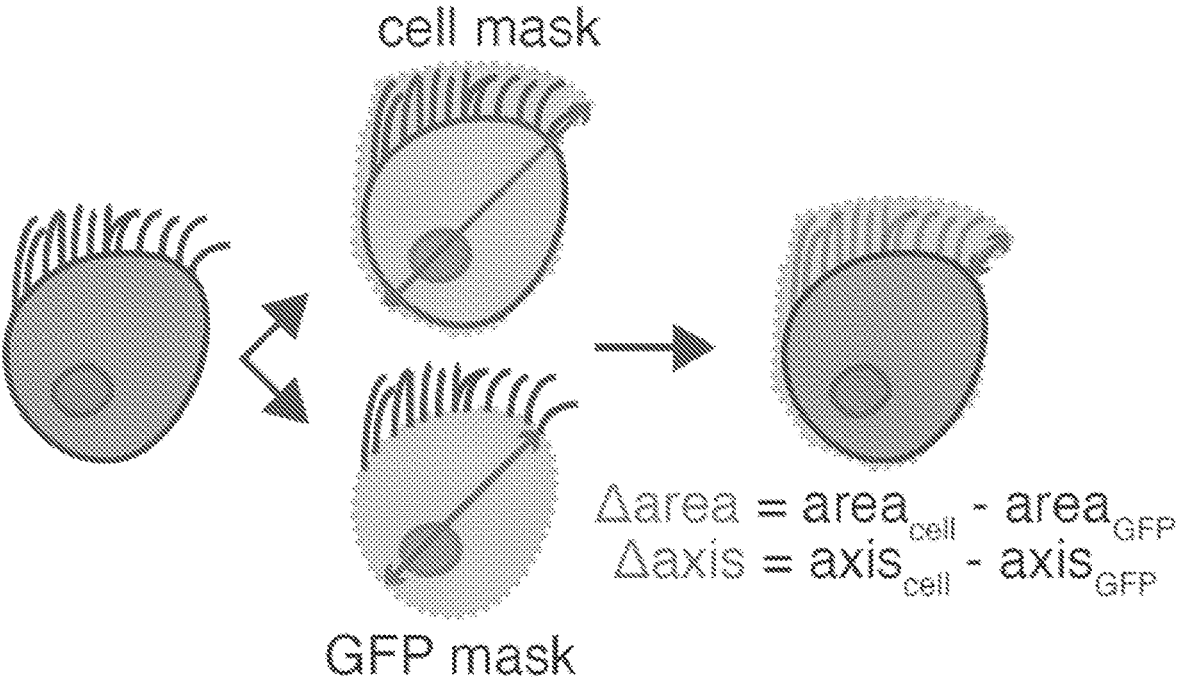
Figure 3B:
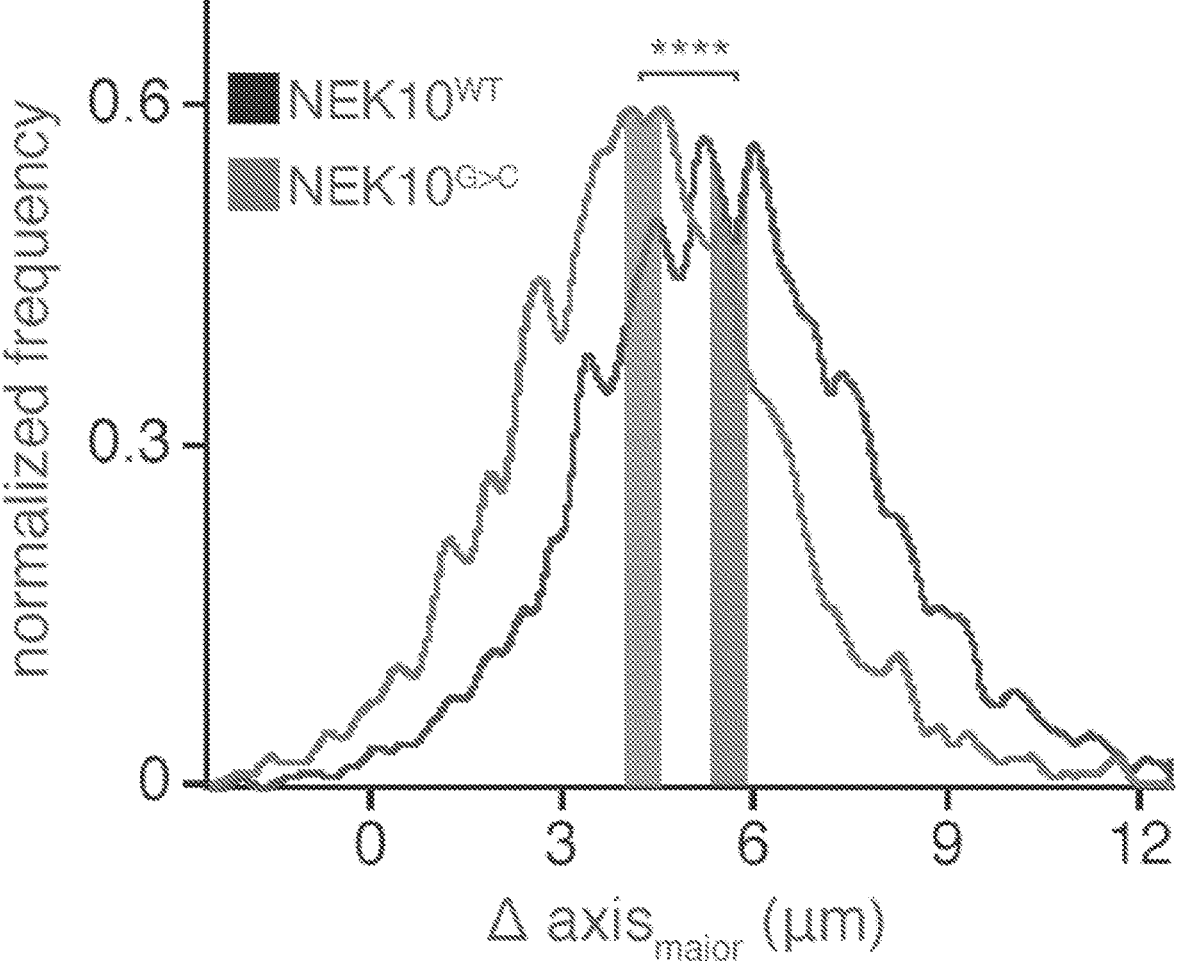
Figure 3C:
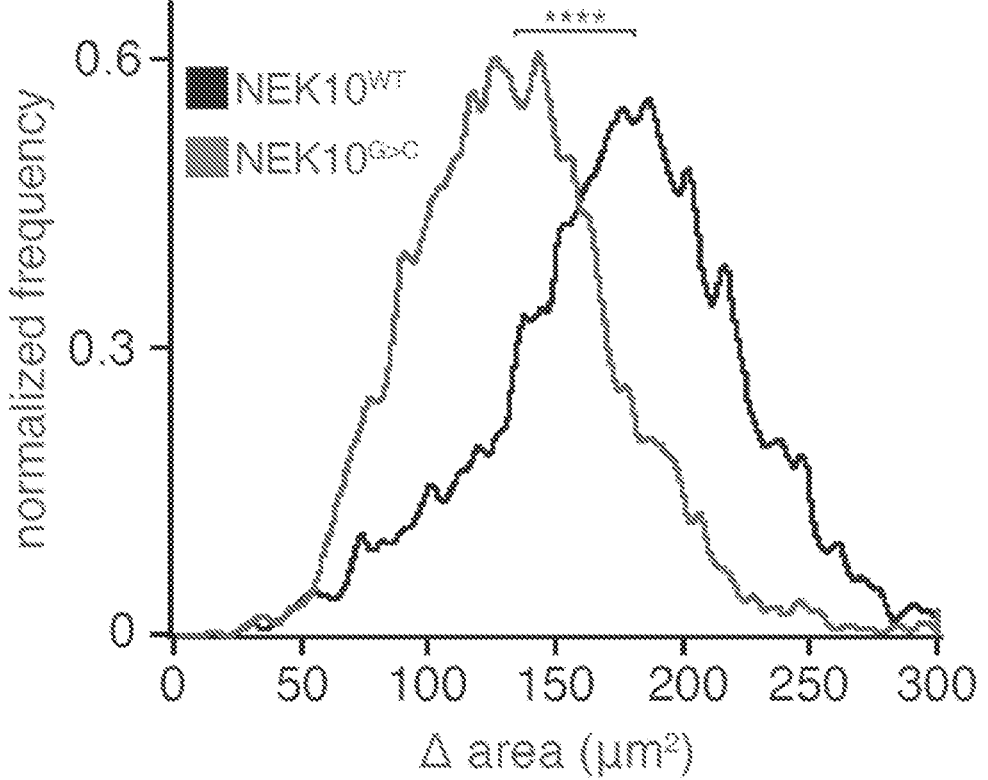
Figure 4A:
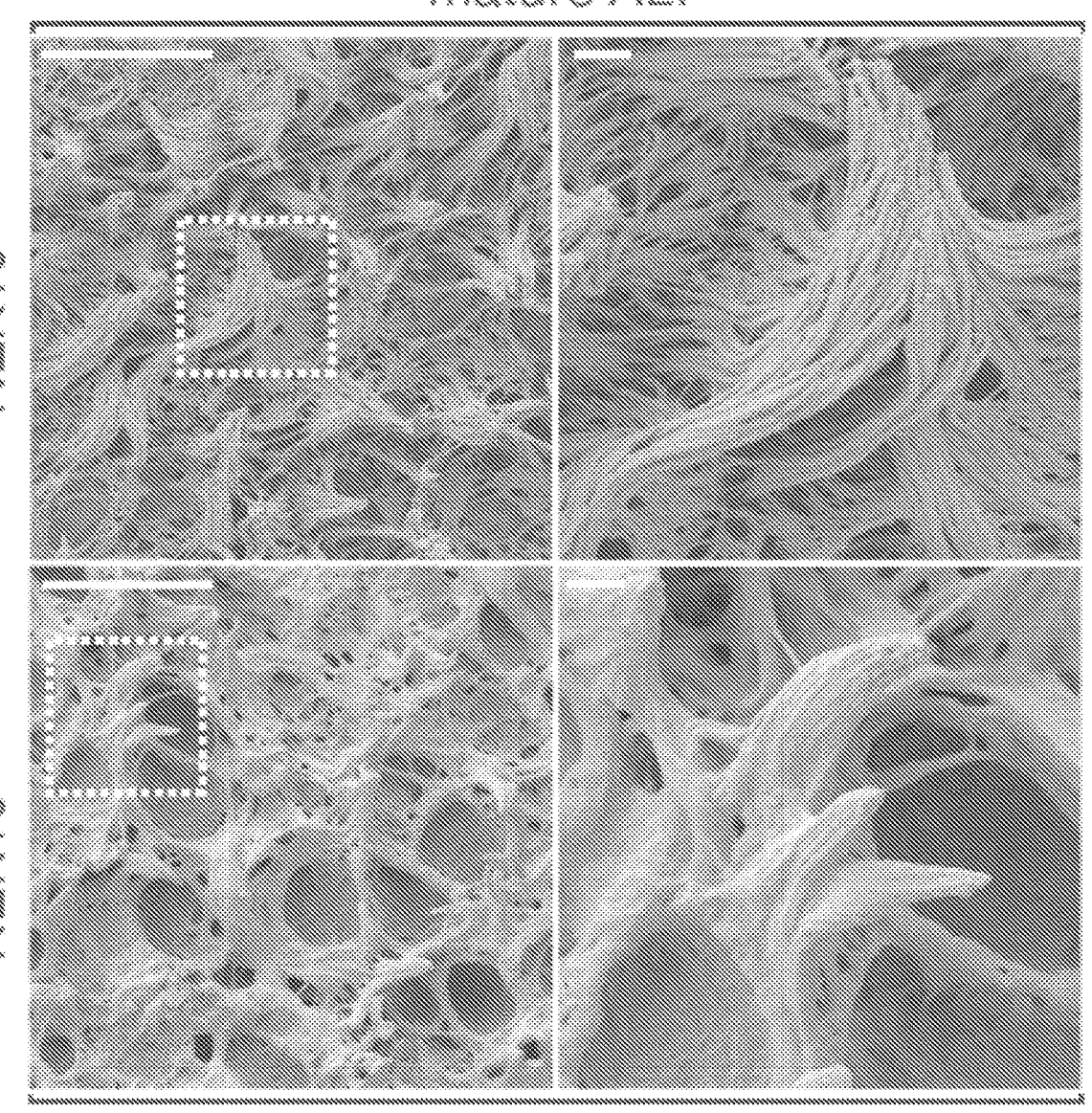
Figure 4B:
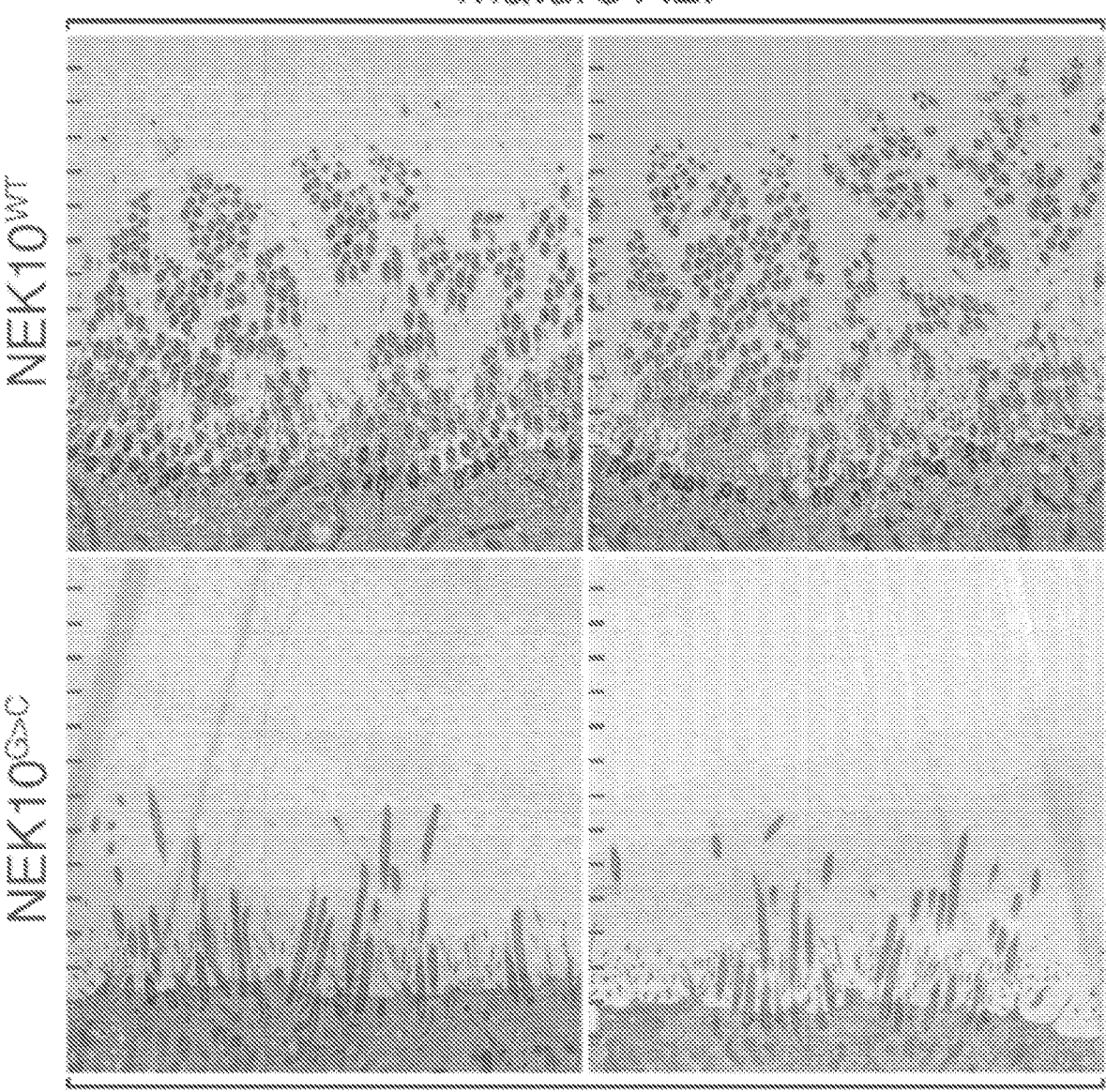
Figure 4C:
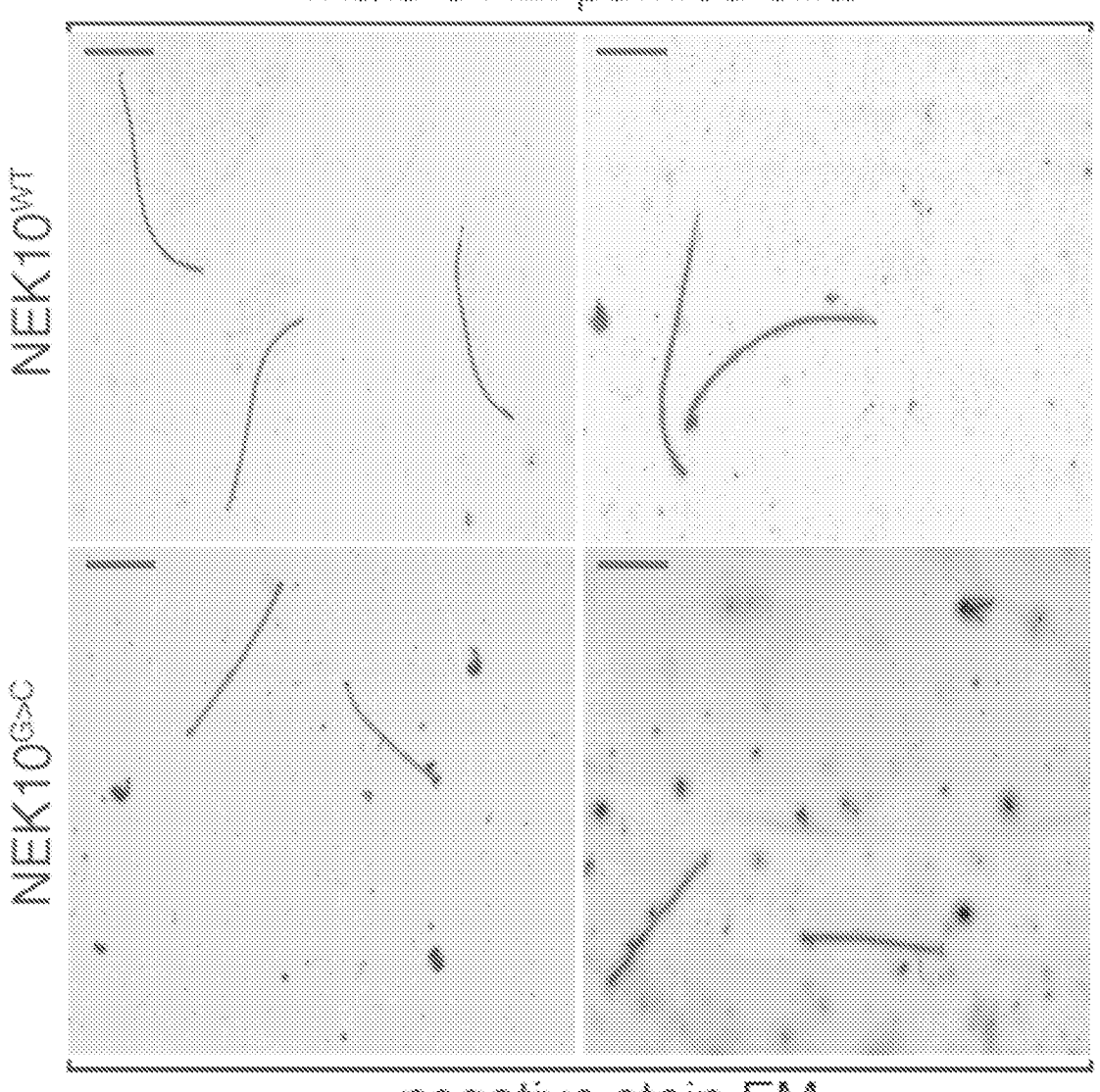
Figure 4D:
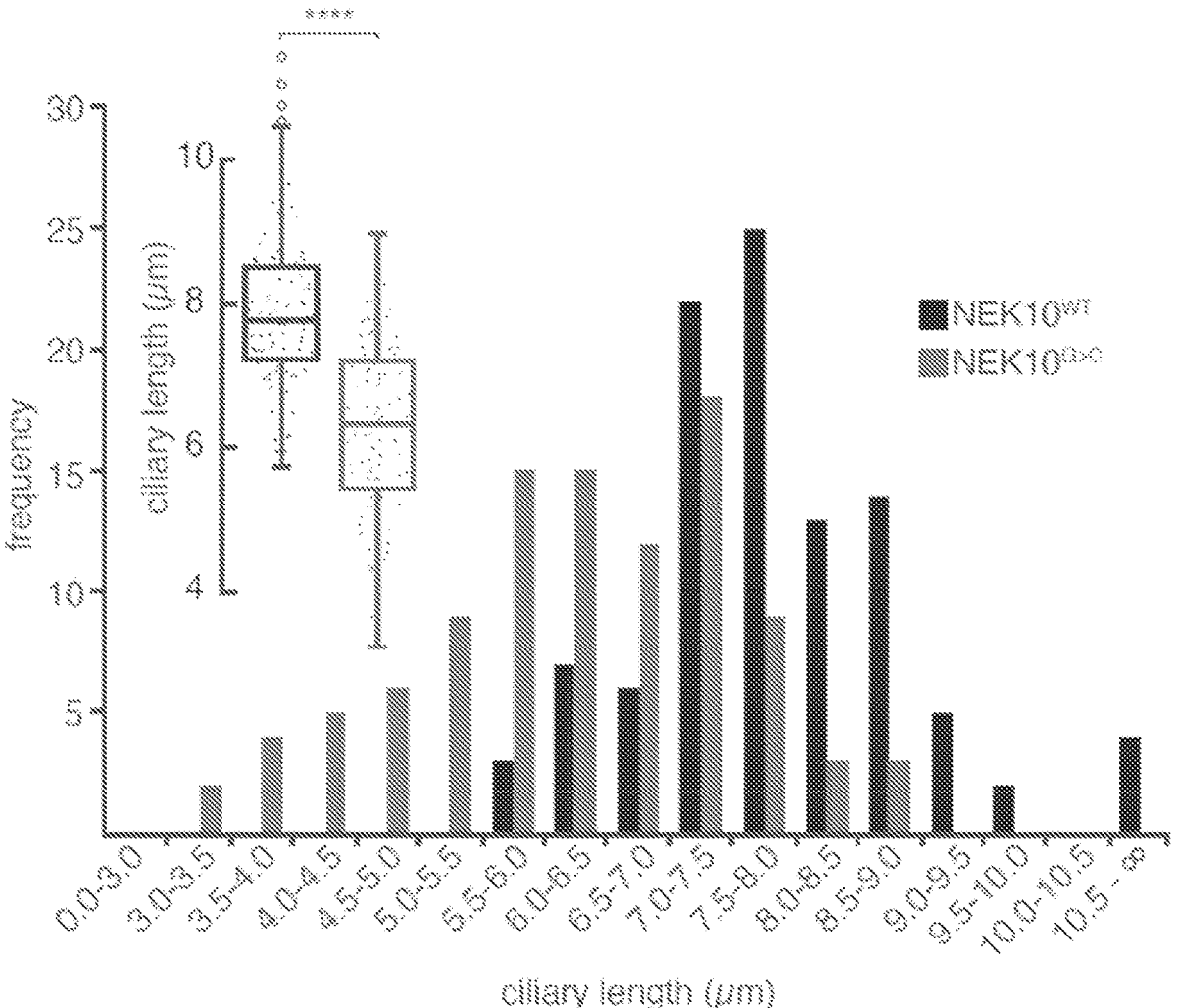
Figure 6A:
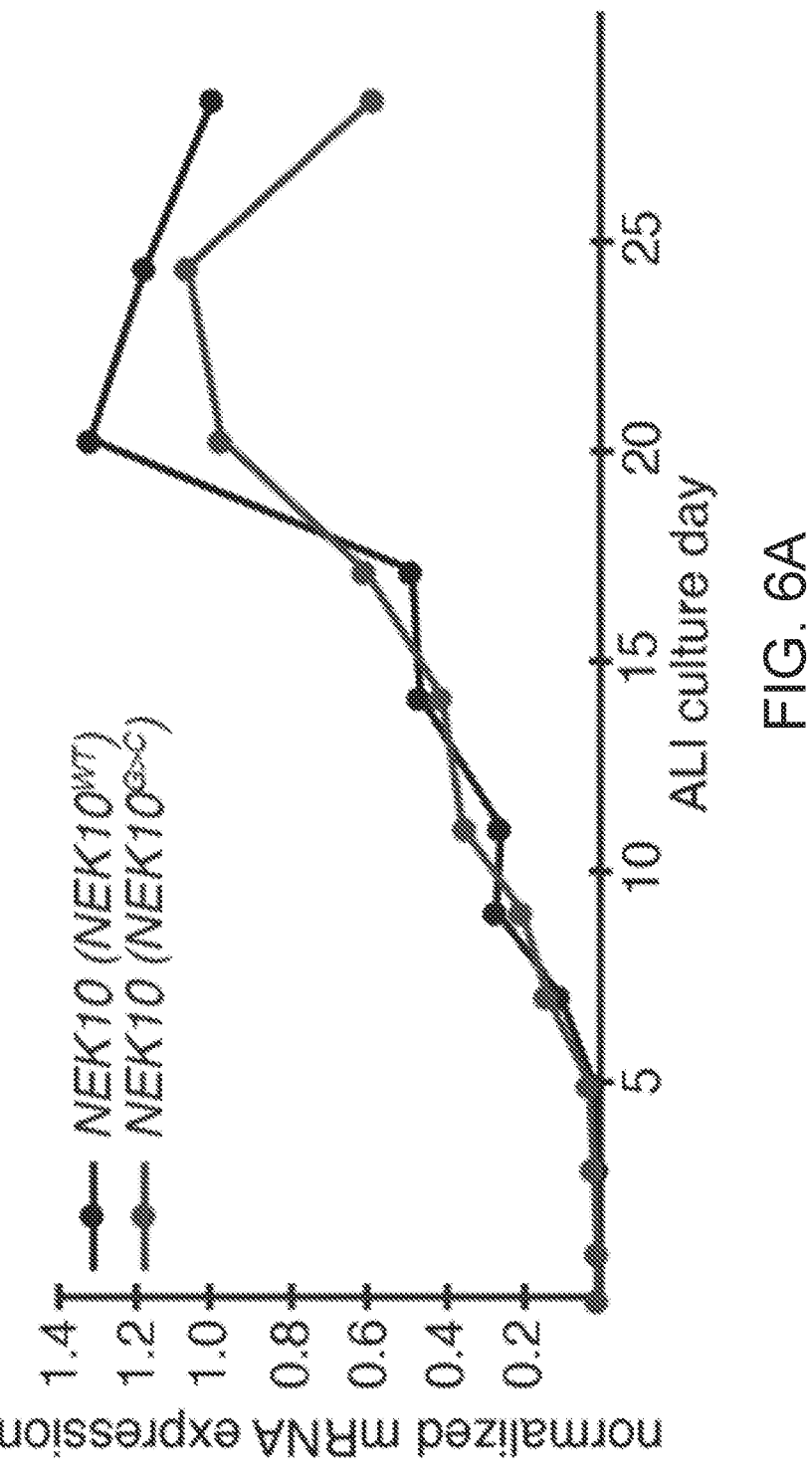
Figure 6B:
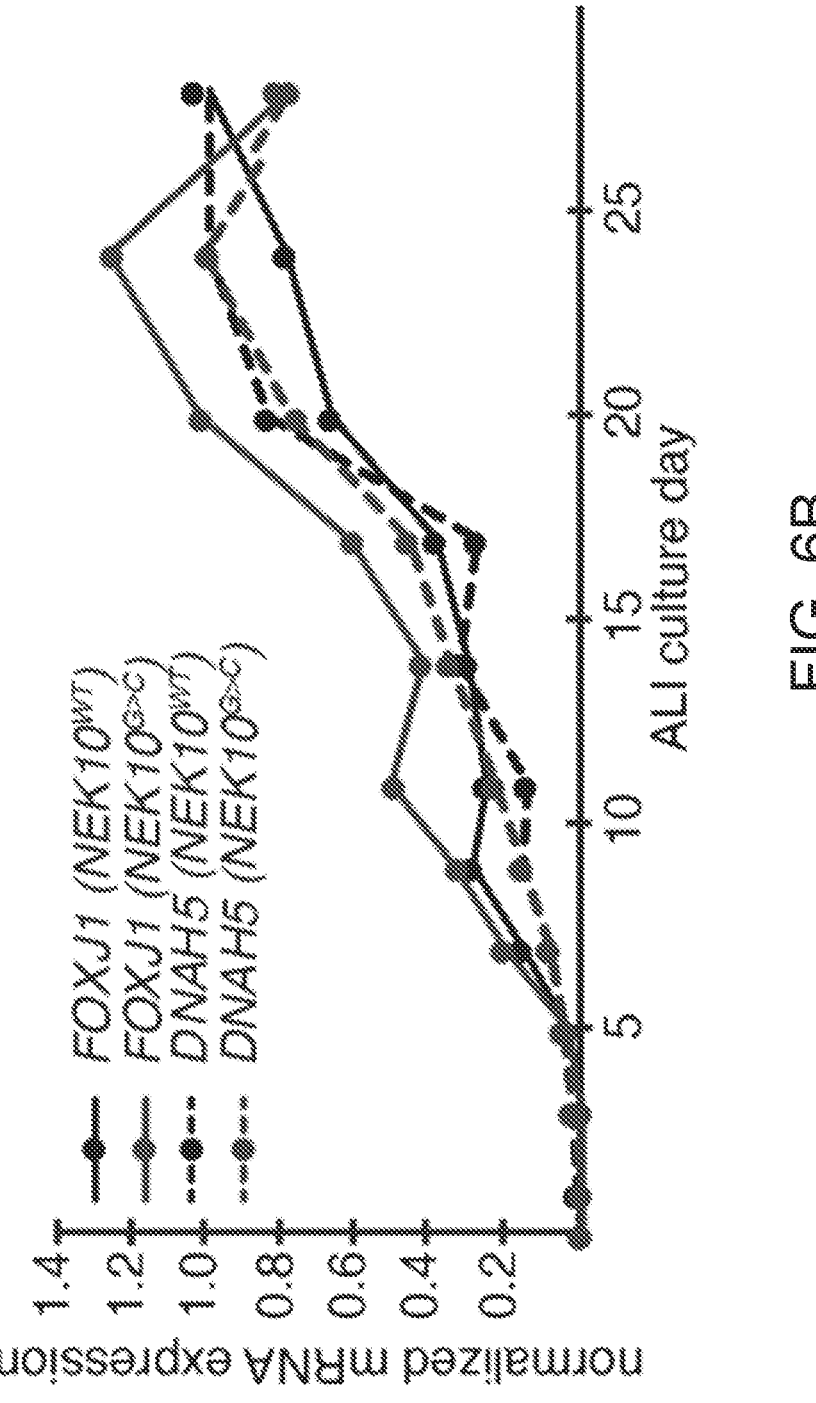
Figure 6C:
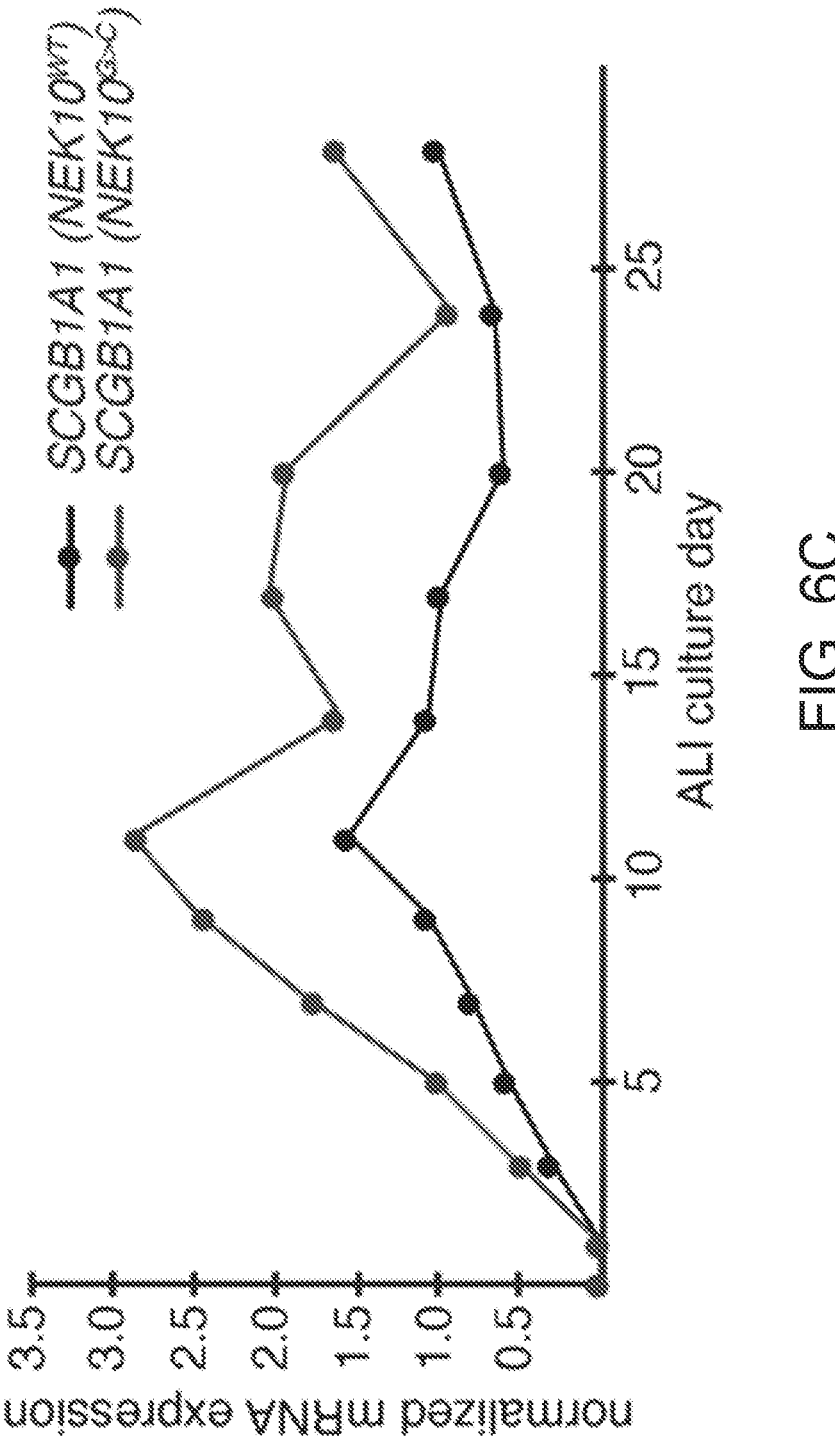
Figure 6D:
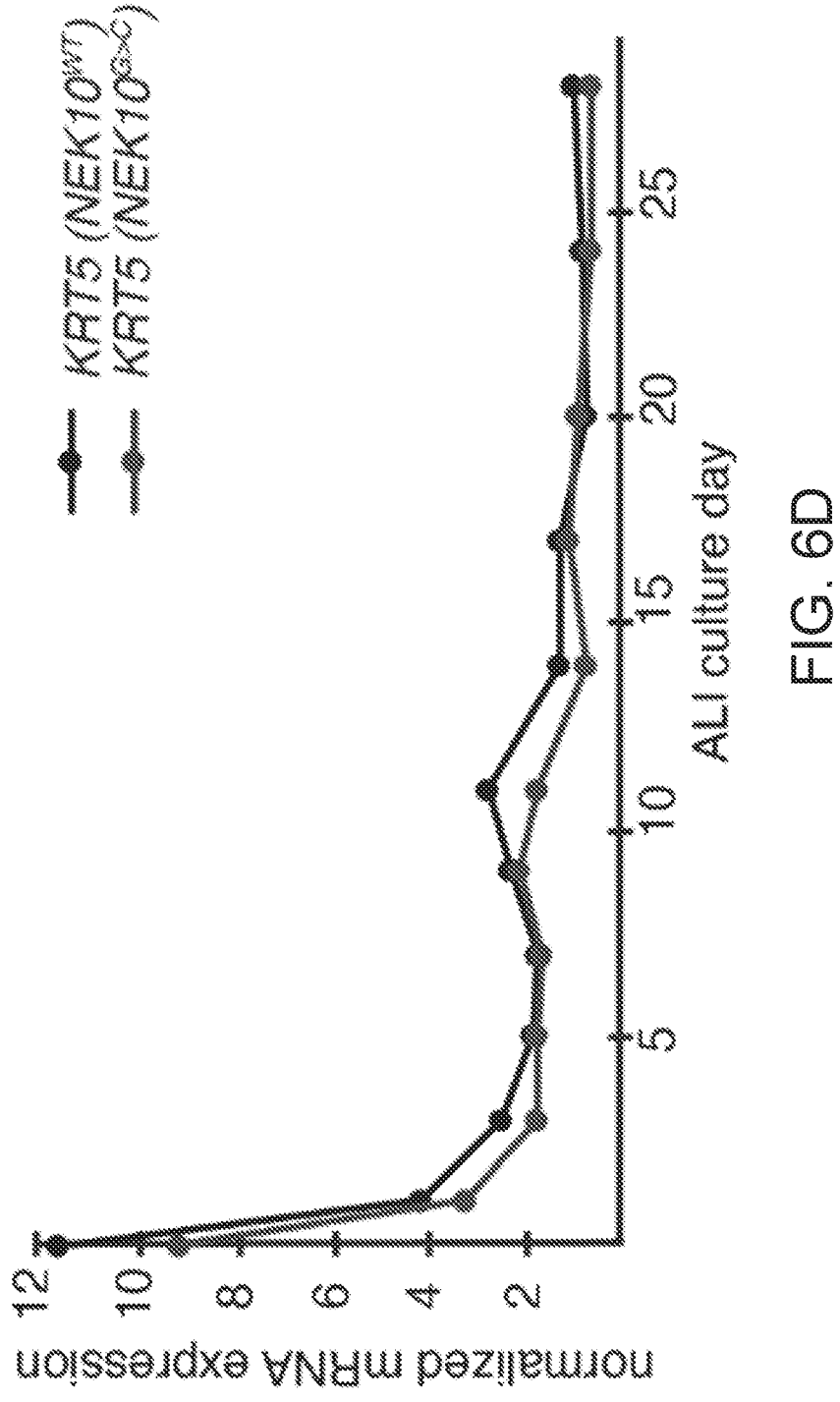
Figure 6E:
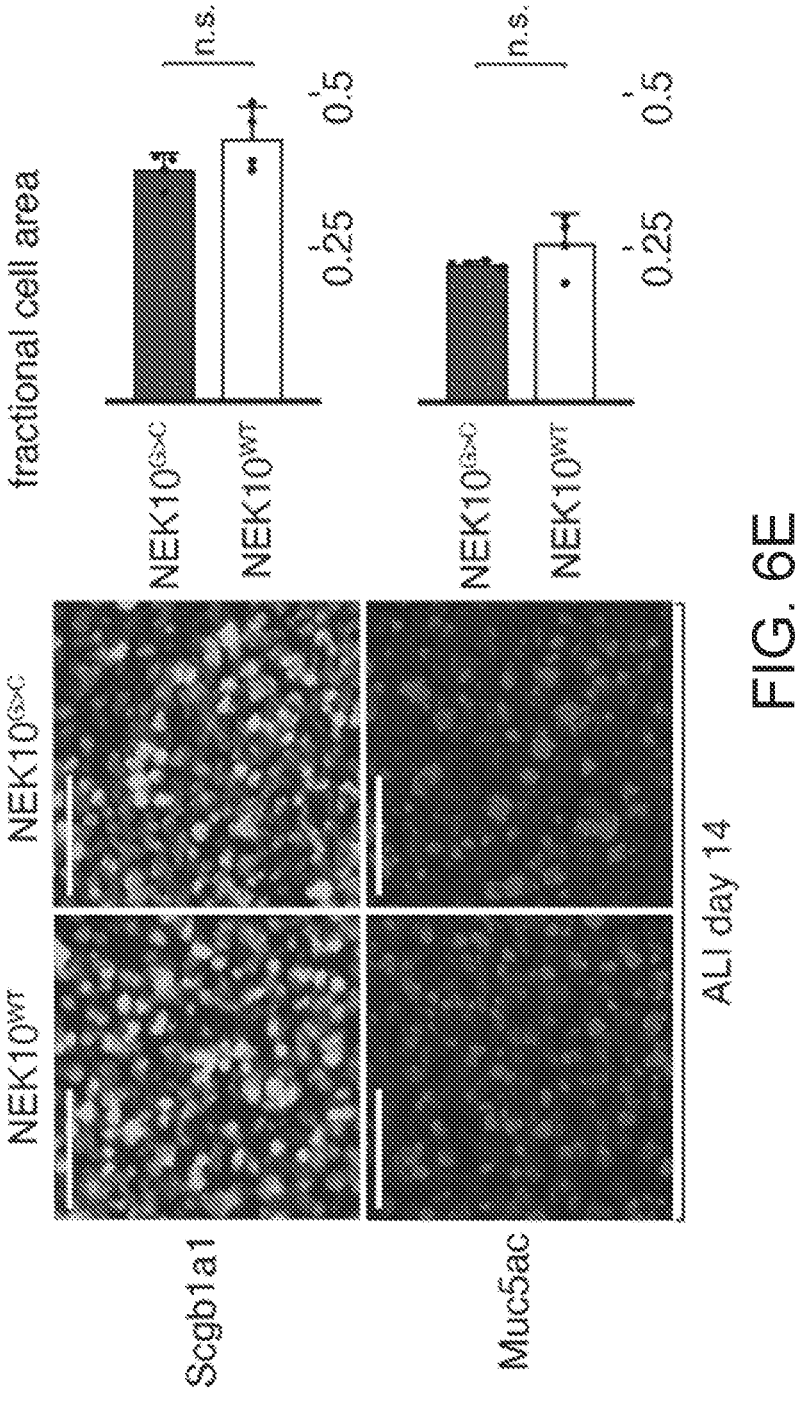
Figure 6F:
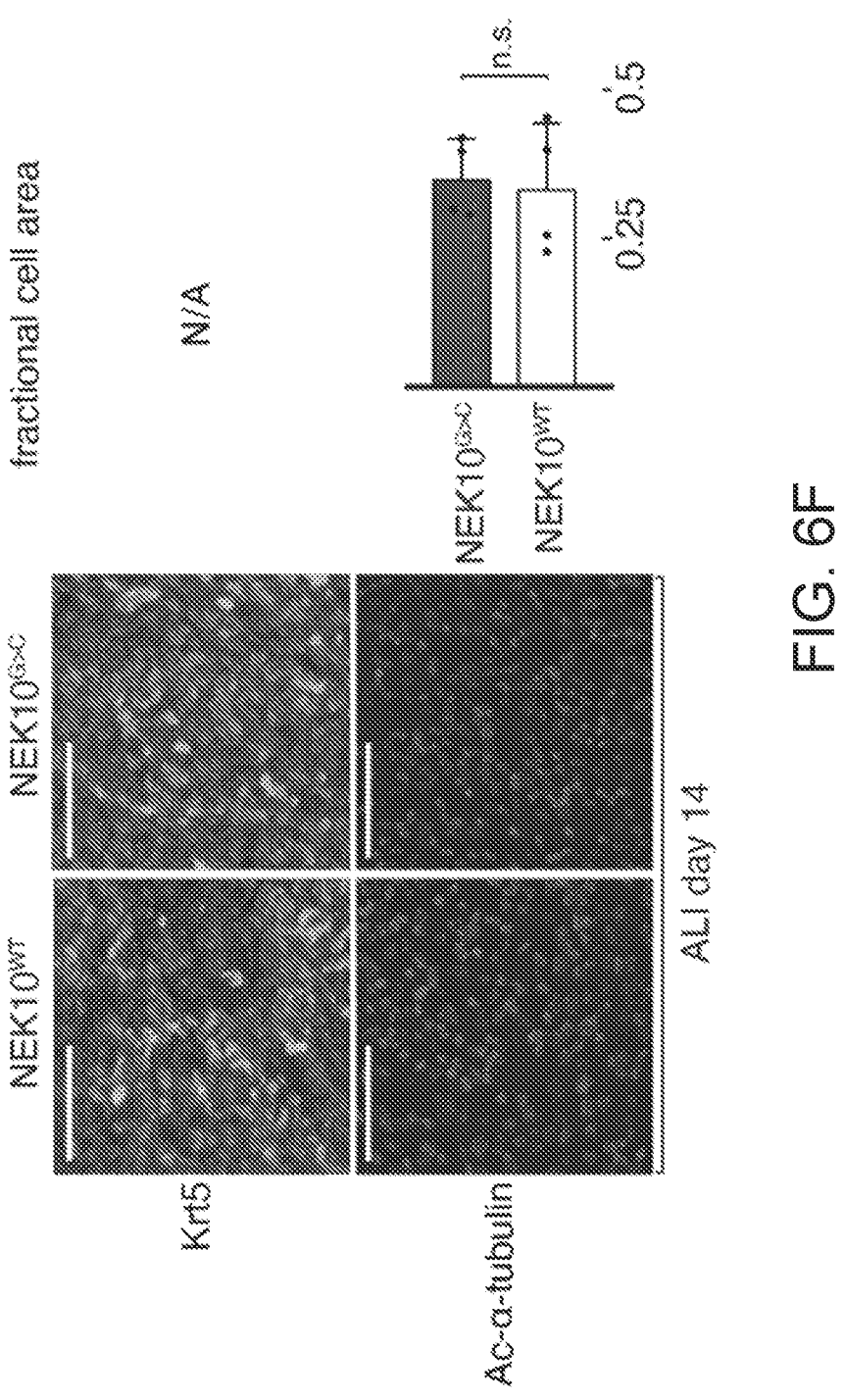
Figure 7A:
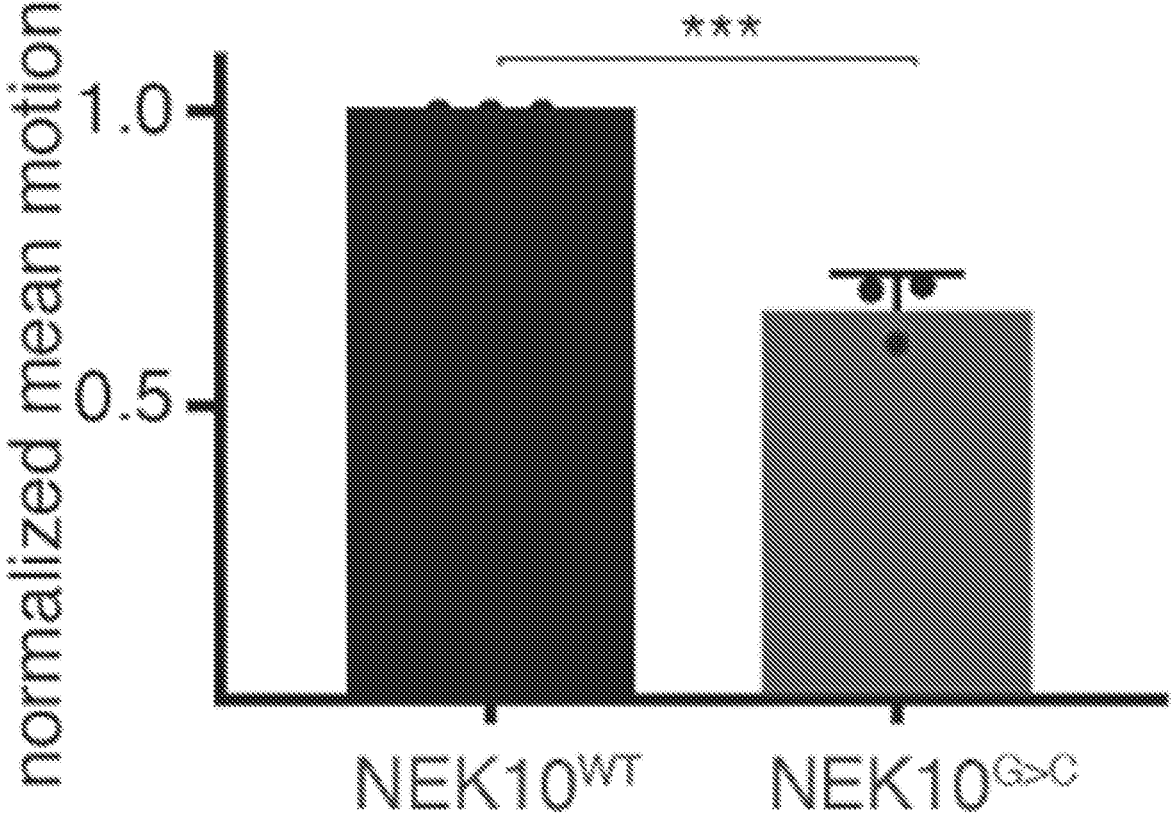
Figure 7B:
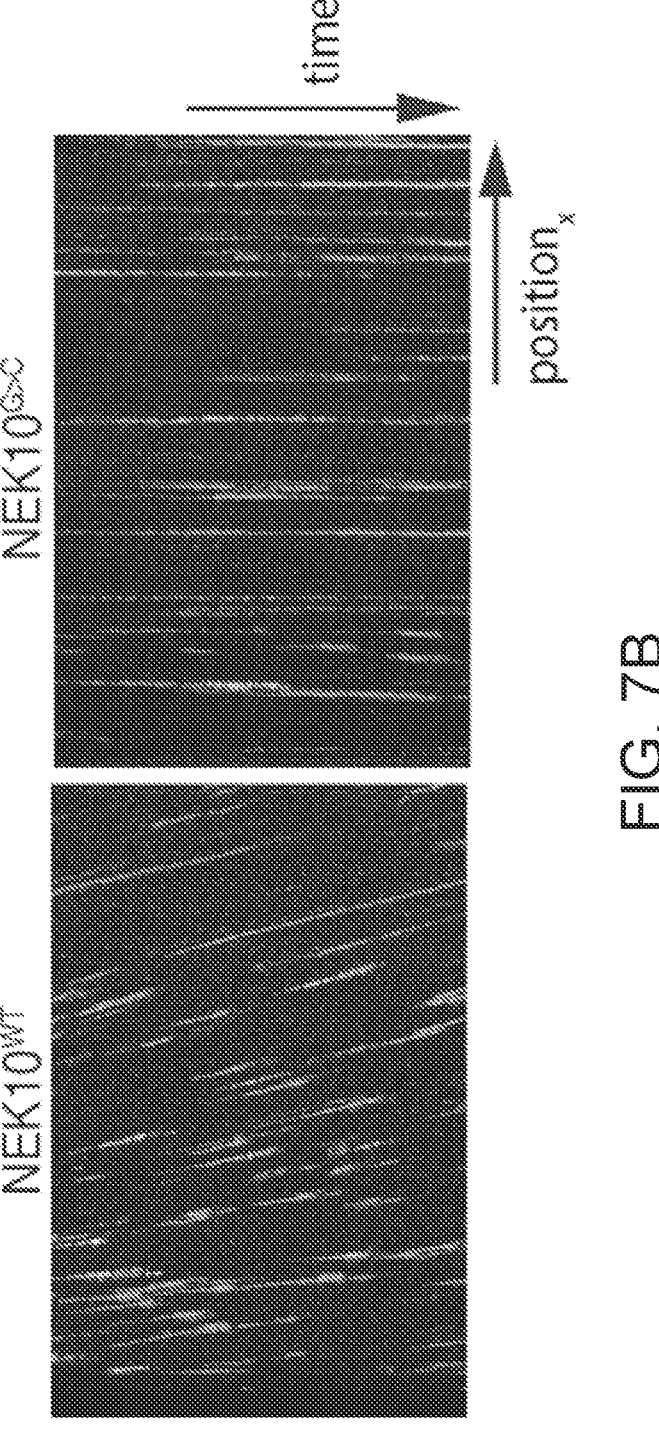
Figure 7C:
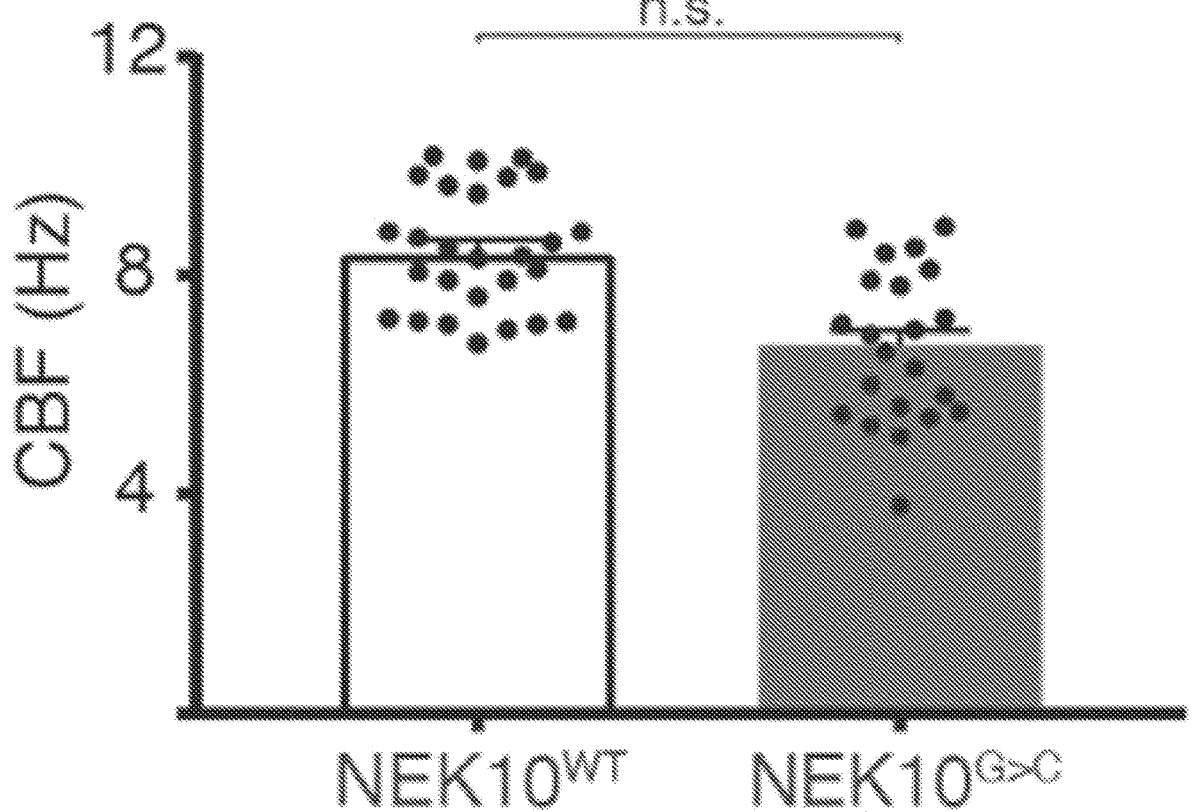
Figure 7D:
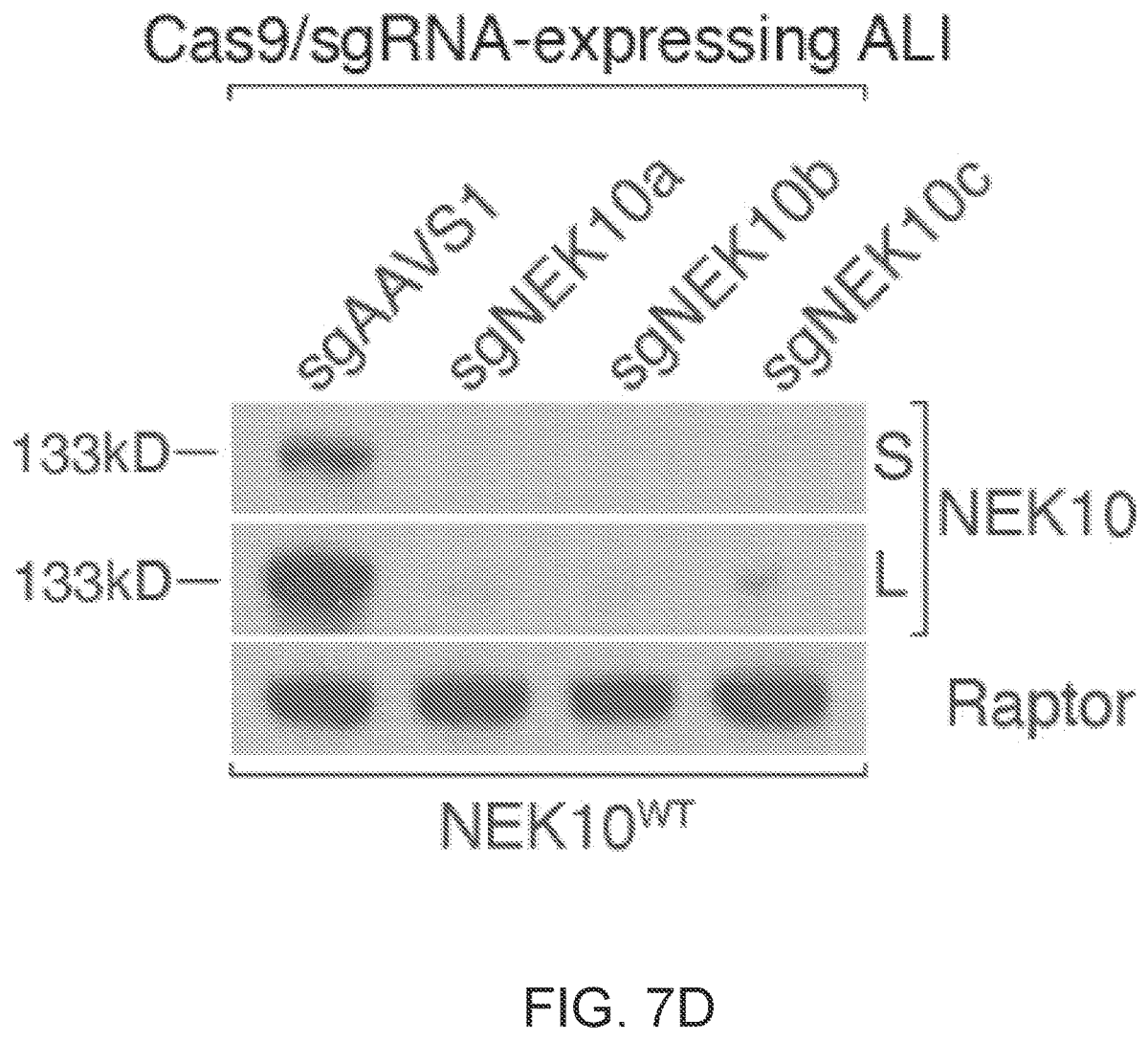
Figure 7E:
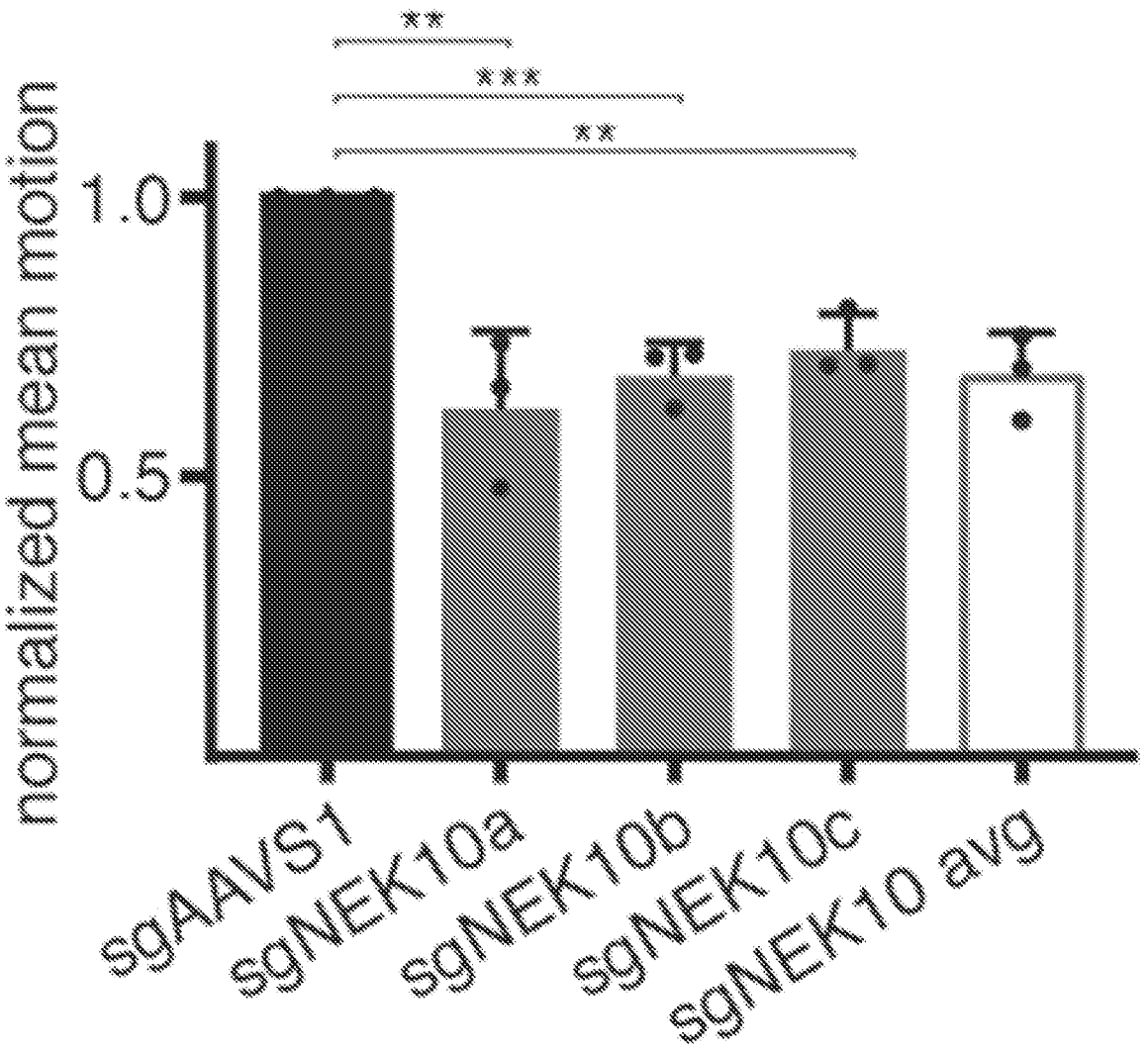
Figure 7F:
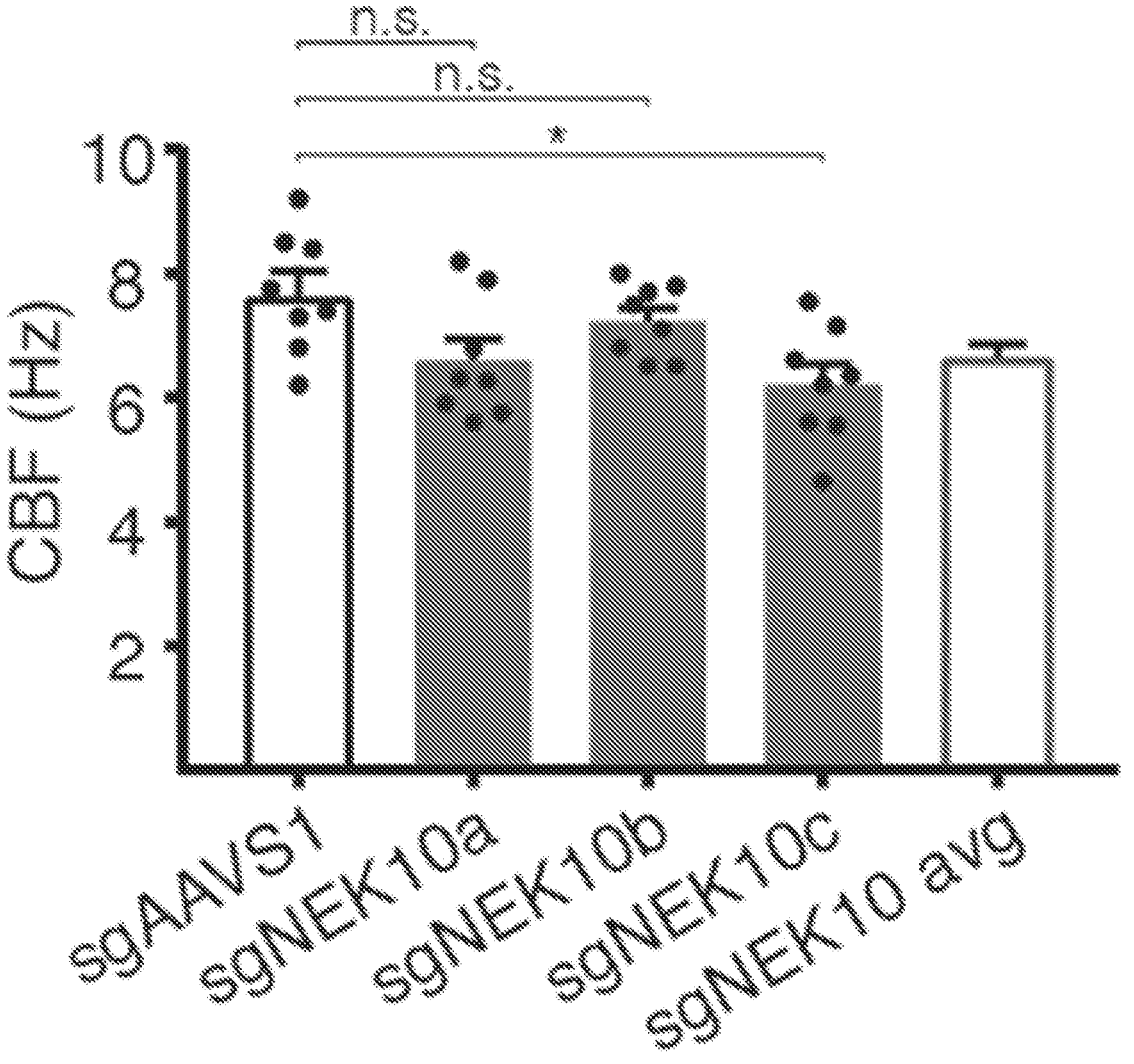
Figure 7G:
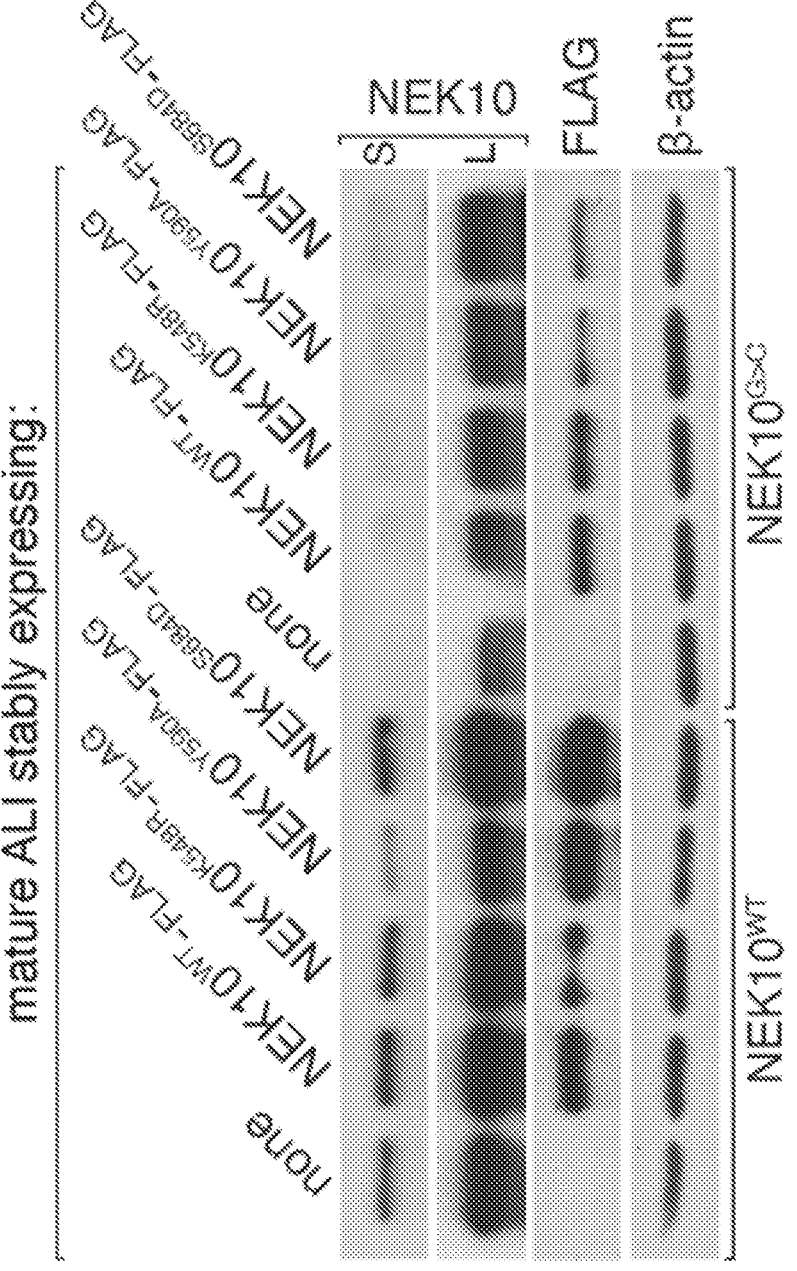
Figure 7H:
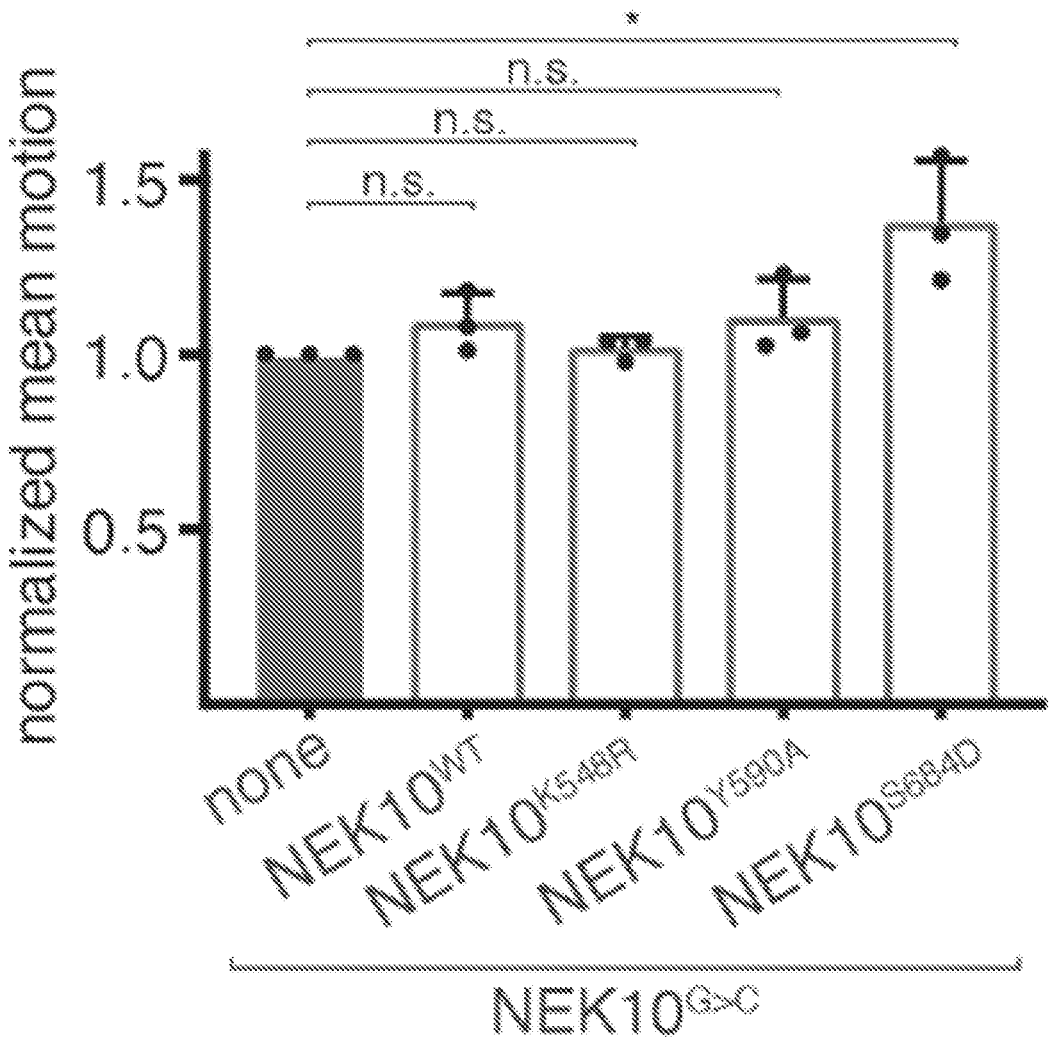
Figure 7I:
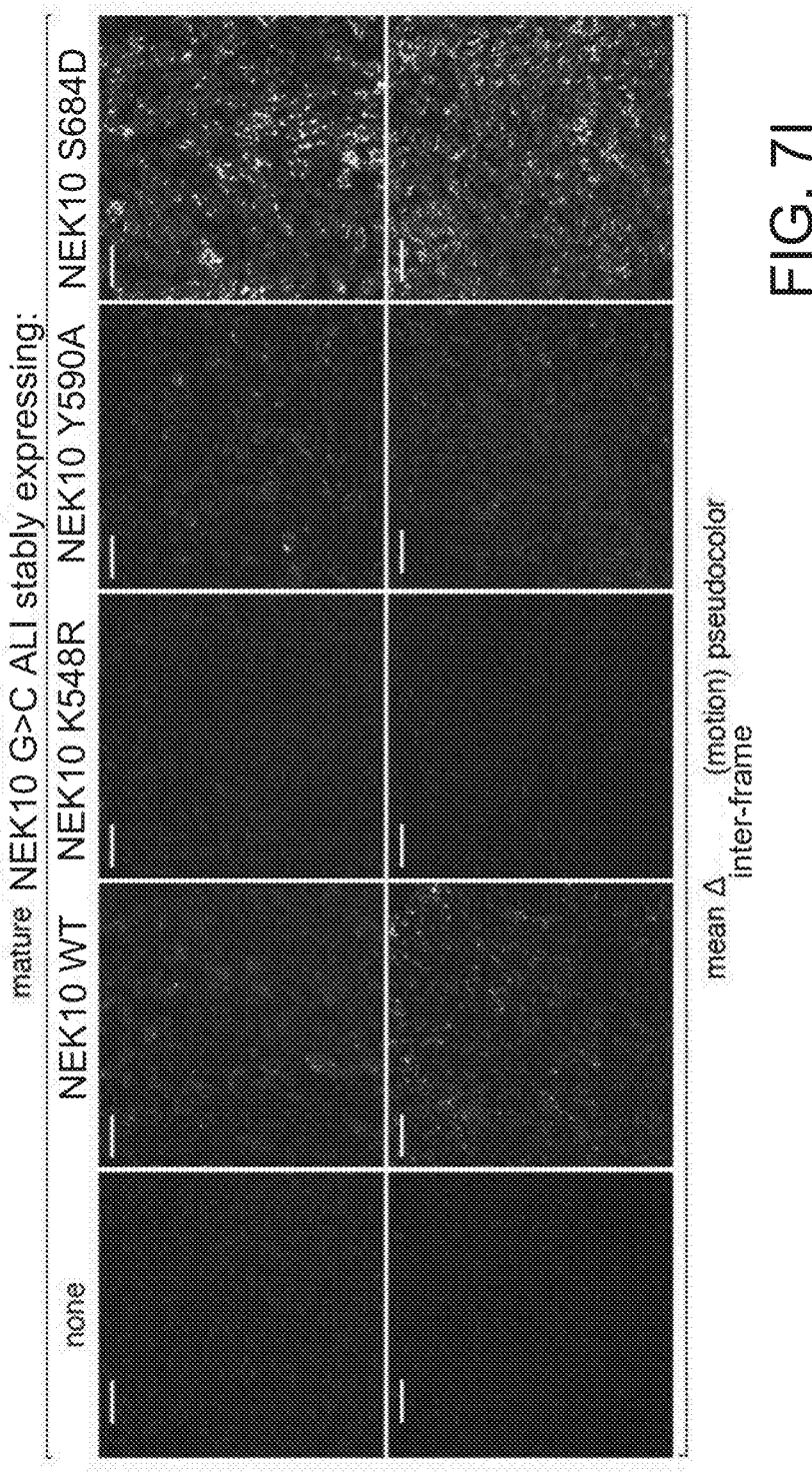
Figure 7J:
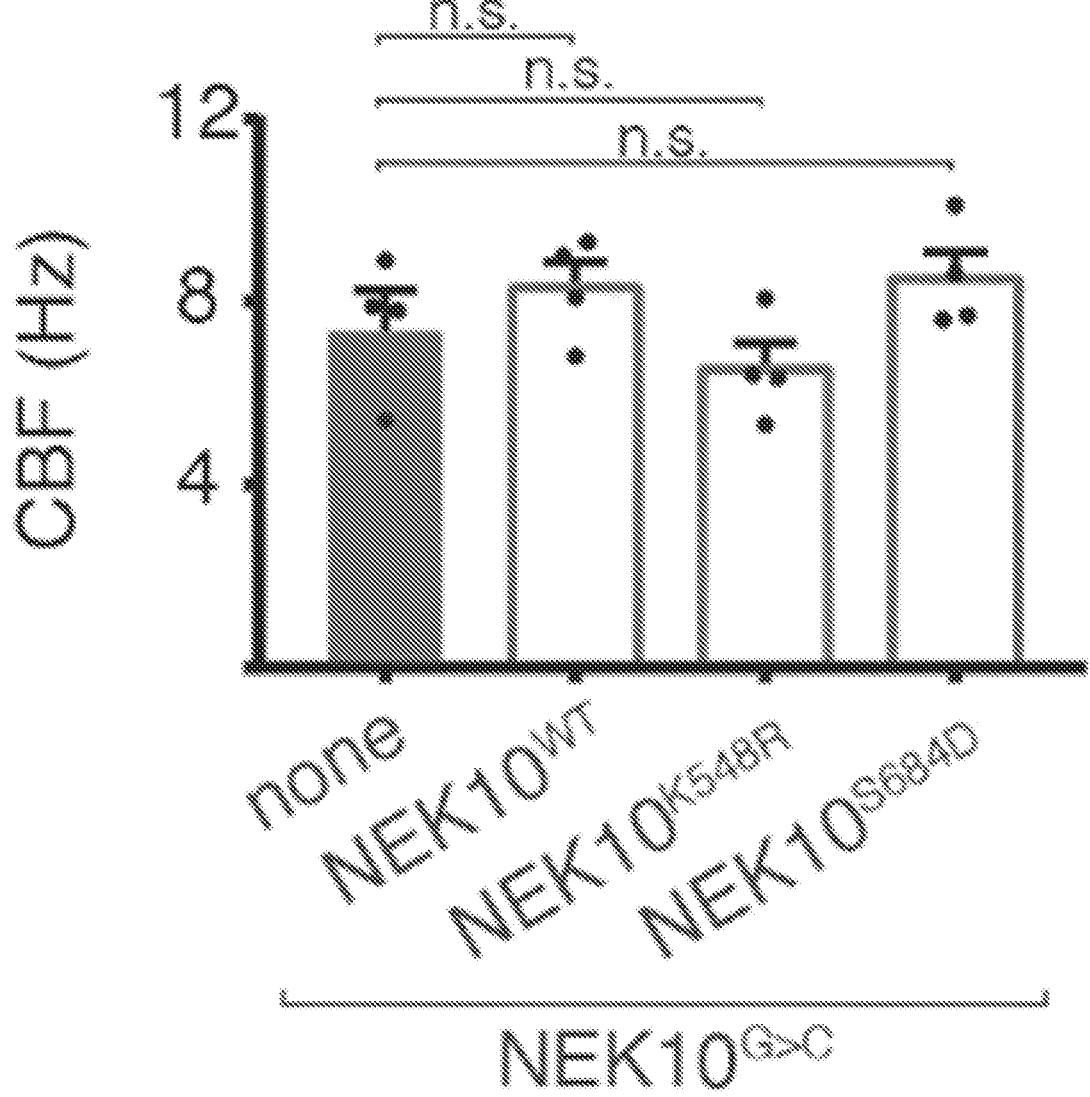

FIG. 1D: Statistical test: 2-tailed homoscedastic Student's t-test. Exact p-values for comparisons of 5', 3' and upstream amplicons 0.77, 0.65, 0.99, respectively. FIGS. 6E-6F: 2-tailed homoscedastic Student's t-test. Exact p-values for comparisons of Scgb1a1, Muc5ac, and Ac-α-tubulin 0.14, 0.21, 0.80, respectively. FIG. 2D: Statistical test: Linear mixed effects model (fixed effect: MCT, random effect: μOCT instrument session), exact p=0.0252. FIG. 2E: Linear mixed effects model (fixed effect: PCL, random effect: μOCT instrument session), exact p=0.0059. FIG. 2G: Statistical test: Mann-Whitney U test, exact p-values all <0.0001 (minimum calculable by software). FIG. 2H: Statistical test: Mann-Whitney U test, exact p-values=0.0286, 0.0159, 0.0095 for sgNEK10a, sgNEK10b, and sgNEK10c, respectively. FIG. 2I: Statistical test: Mann-Whitney U test, exact p-values=0.0086, 0.8967, <0.0001 for NEK10WT, NEK10K548R, NEK10S684D, respectively. FIG. 7A: Statistical test: 2-tailed homoscedastic Student's t-test. Exact p-value 0.00048. FIG. 7C: Statistical test: Linear mixed effects model (fixed effect: CBF, random effect: μOCT instrument session), exact p-value=0.1109. FIG. 7E: Statistical test: 2-tailed homoscedastic Student's t-test, exact p-values 0.0085, 0.0006, 0.0014 for sgNEK10a, sgNEK10b, and sgNEK10c, respectively. FIG. 7F: Statistical test: Mann-Whitney U test, exact p-values=0.0535, 0.3947, 0.0112 for sgNEK10a, sgNEK10b, and sgNEK10c, respectively. FIG. 7H: Statistical test: 2-tailed homoscedastic Student's t-test, exact p-values=0.1374, 0.4176, 0.1688, 0.0220 for NEK10WT, NEK10K548R, NEK10Y590A, NEK10S684D respectively. FIG. 7J: Statistical test: Mann-Whitney U test, exact p-values=0.3429, 0.4857, 0.8857 for NEK10WT, NEK10K548R, NEK10S684D respectively. FIG. 3B: Statistical test: 2-tailed homoscedastic Student's t-test, exact p-value=1.802×10−124. FIG. 3C: Statistical test: 2-tailed homoscedastic Student's t-test, exact p-value=0.0000 (minimum calculable by Microsoft Excel). FIG. 4D: Statistical test: 2-tailed homoscedastic Student's t-test, exact p-value 3.005×10−19. FIG. 9D: Statistical test: Fisher's Exact with false discovery rates listed for multiple hypothesis correction, p-values in table.

Data Availability Statement

Sequence data supporting the findings of this study have been deposited in NCBI GenBank, accession numbers MK806425 and MK806426 (embargoes released at publication). The mass spectrometry proteomics data have been deposited to the ProteomeXchange Consortium via the PRIDE partner repository with the dataset identifier PXD016600 (embargo released at publication) (Perez-Riverol et al. The PRIDE database and related tools and resources in 2019: improving support for quantification data. *Nucleic Acids Res* 47, D442-D450 (2019)). Plasmids pLRC1-NEK10p:NEK10-3XFLAG and pLRC1-FOXJ1p:NEK10-3XFLAG available for review and distribution at publication through Addgene (addgene.org, plasmid numbers 137030, 137031).

Figure 5A:
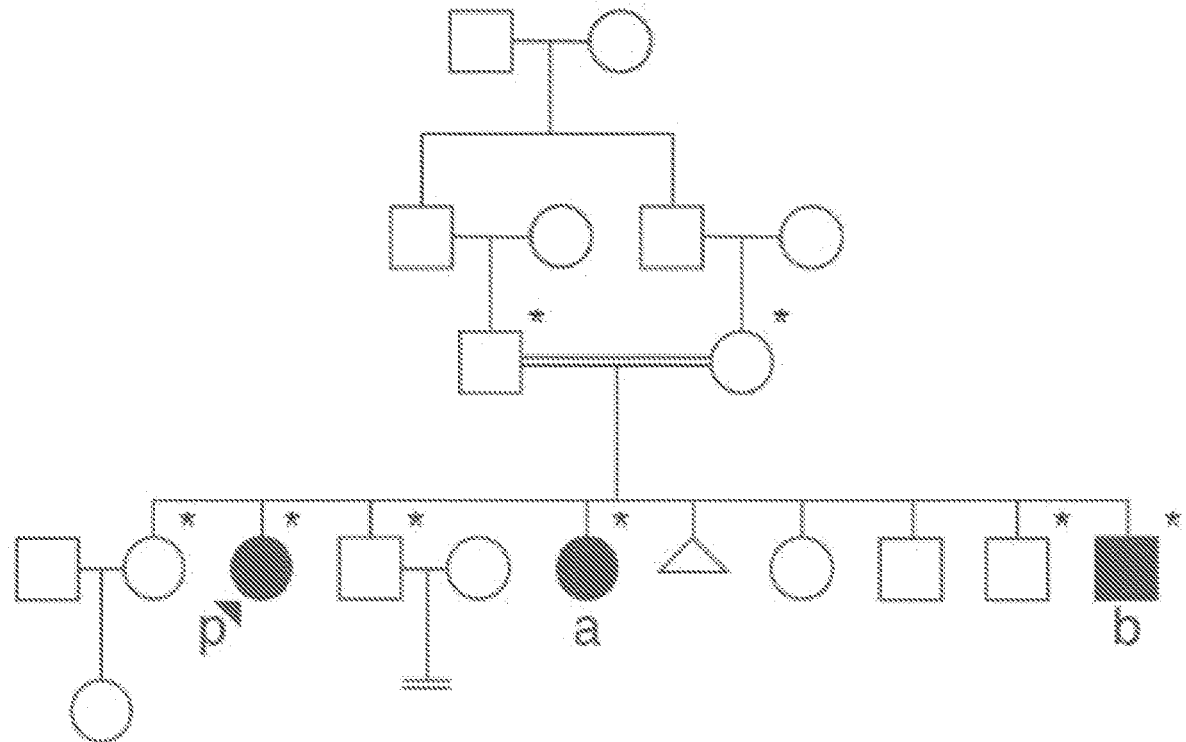
Figure 5B:
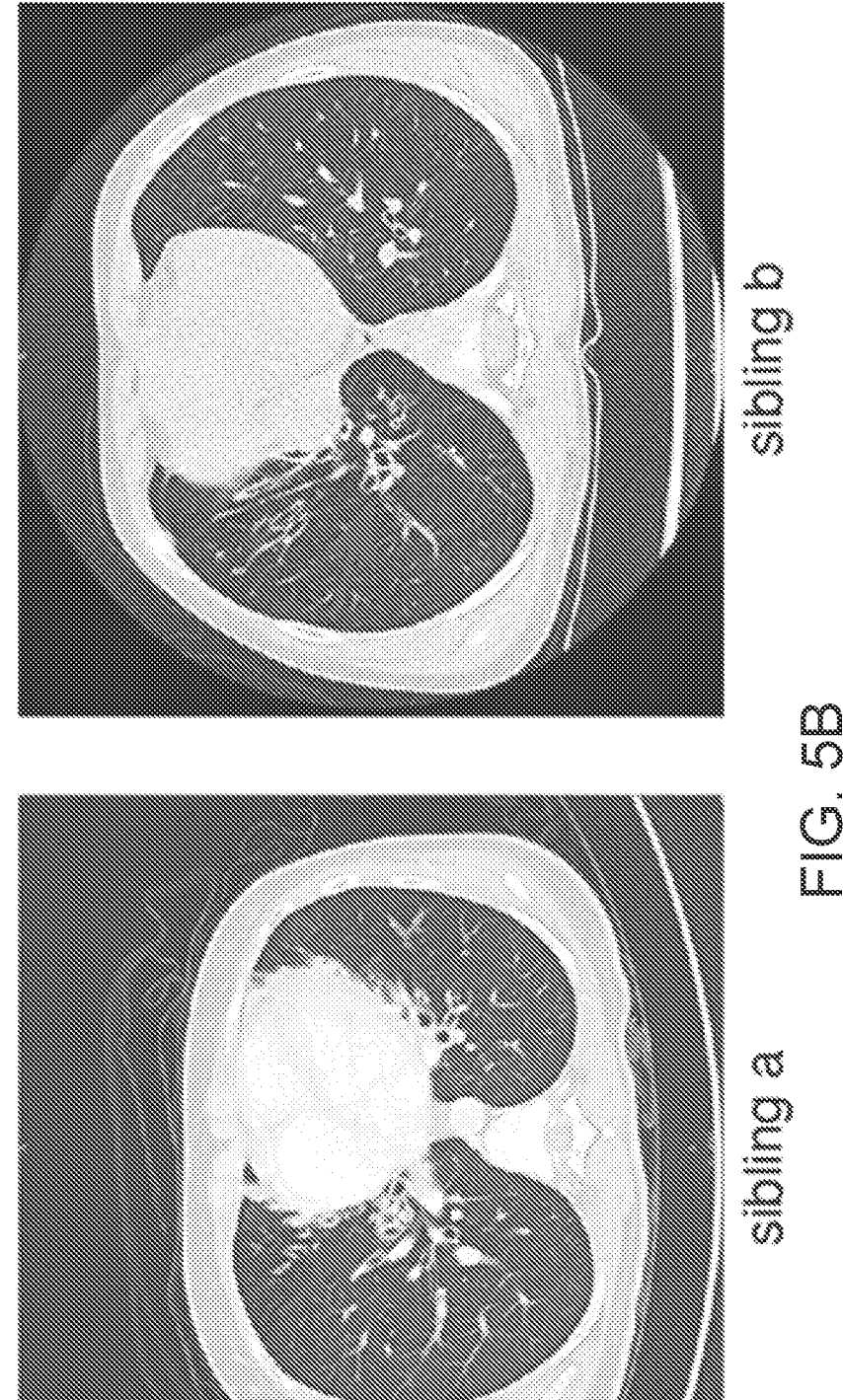
FIG. 5B includes representative images from chest computed tomography (CT) of siblings "a" and "b" from (FIG. 5A), arrows indicate regions of bronchiectatic lung.

Example 1: Familial Bronchiectasis is Associated with NEK10 Loss-of-Function A 31-year-old consanguineous woman was evaluated for idiopathic respiratory failure characterized by neonatal respiratory distress and recurrent bacterial sinopulmonary infections (FIG. 5A, Table 2). Chest imaging demonstrated extensive pan-lobar bronchiectasis without heterotaxy and nasal biopsies revealed normal ciliary radial ultrastructure (FIGS. 1A-1B). Cystic fibrosis and immunodeficiency were ruled out after extensive clinical and genetic testing. Similar but milder findings were present in 2 siblings (FIGS. 5A-5B, Table 2), strongly suggestive of autosomal recessive inheritance. Whole exome sequencing of affected individuals unexpectedly revealed homozygous intronic splice site mutations (NM_152534:c.1230+5G>C, "NEK10$^{G>C}$" hereafter) in NEK10, a serine/threonine kinase homologous to *Aspergillus nidulans* nimA ("never in mitosis a") but not previously implicated in human disease (Online Mendelian Inheritance in Man, OMIM. omim.org) (FIG. 1C). The functions of mammalian NEKs remain incompletely characterized; several, including NEK2 and NEK5/6/7/9 function like their fungal ortholog by regulating the cell cycle through phosphorylation of centrosome components and the mitotic spindle (Moniz et al. Nek family of kinases in cell cycle, checkpoint control and cancer. *Cell Division* 2011 6:1 6, 18 (2011)). Mutations in NEK1 and NEK8 cause polycystic kidney phenotypes in mice (Thiel et al. NEK1 Mutations Cause Short-Rib Polydactyly Syndrome Type Majewski. *The American Journal of Human Genetics* 88, 106-114 (2011); and Smith et al. Development of polycystic kidney disease in juvenile cystic kidney mice: insights into pathogenesis, ciliary abnormalities, and common features with human disease. *J Am. Soc. Nephrol* 17, 2821-2831 (2006)), in line with a role in regulation of primary cilia. Recent reports have proposed roles for NEK10 in cancer cell DNA damage response (Moniz & Stambolic Nek10 mediates G2/M cell cycle arrest and MEK autoactivation in response to UV irradiation. *Mol Cell Biol* 31, 30-42 (2011)) and in teleost fish nervous system and body axis specification (Porpora et al. Counterregulation of cAMP-directed kinase activities controls ciliogenesis. *Nat Comms* 9, 1224 (2018)) but, to date, no published work suggests any roles for NEKs in the respiratory system.

Figure 1E:
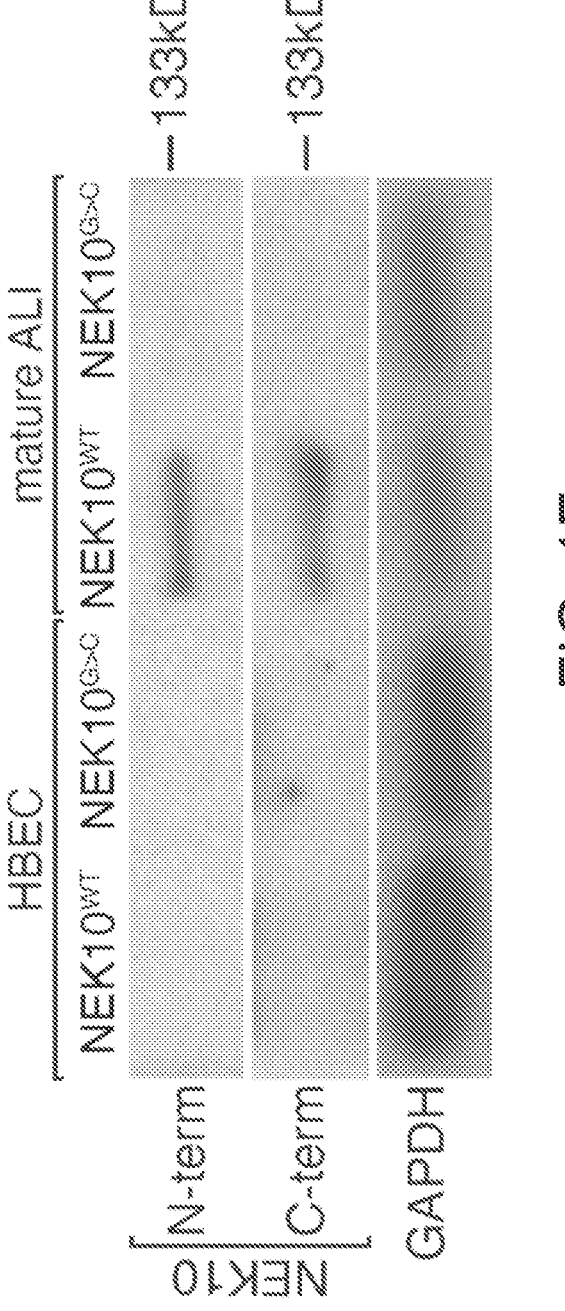
Figure 1F:
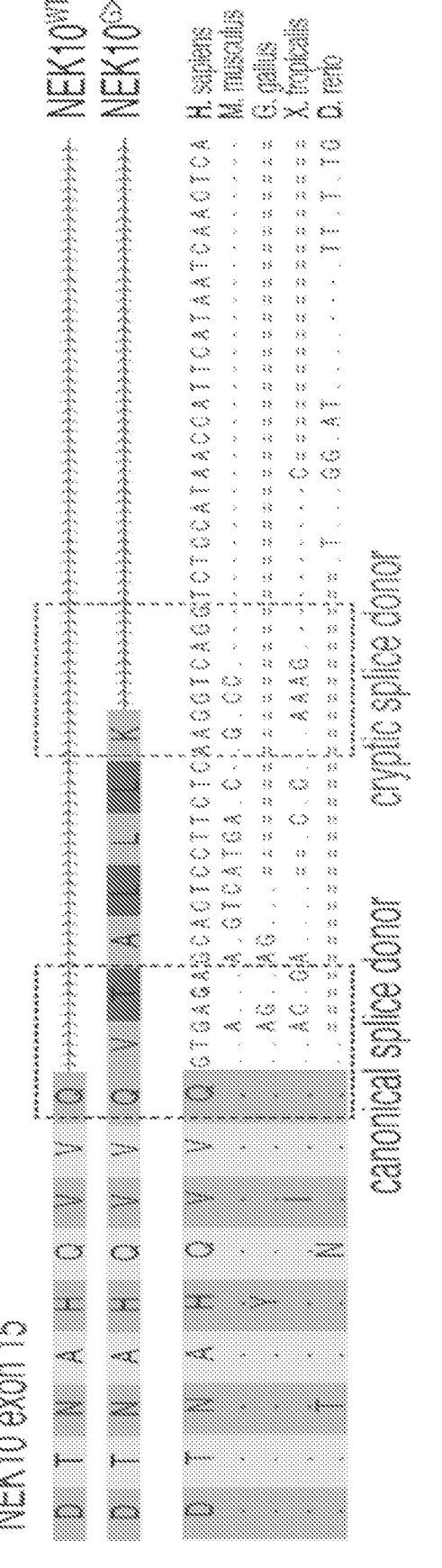
Figure 1G:
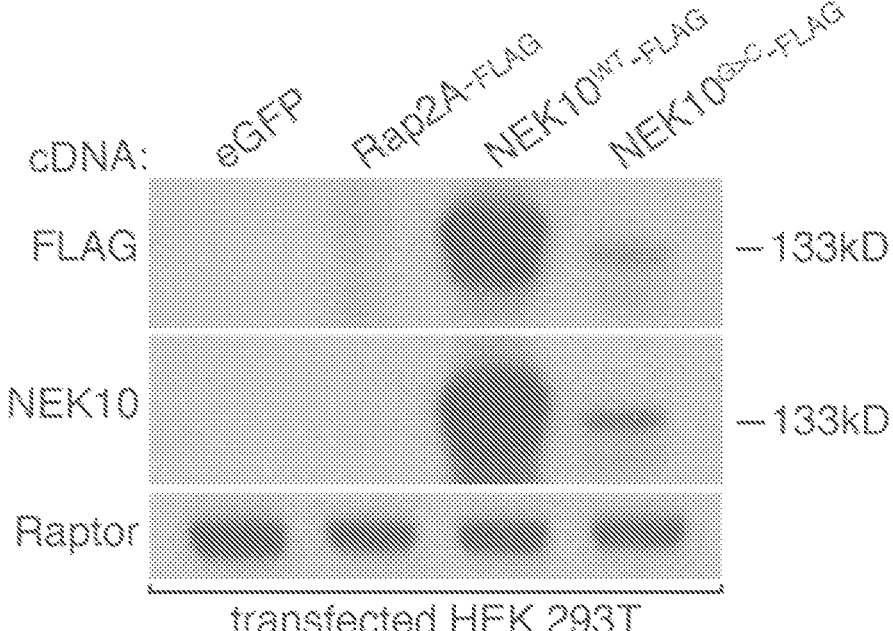
Figure 5C:
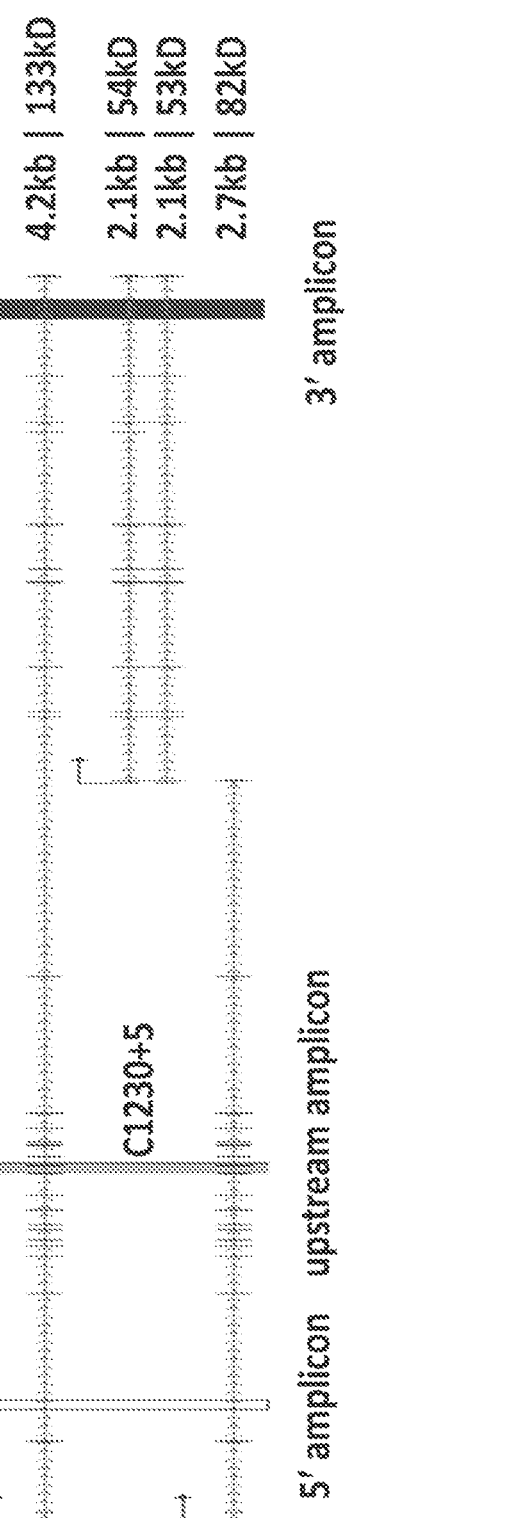
FIG. 5C includes a schematic of RefSeq-annotated NEK10 variants annotated with transcription start sites, transcript sizes, predicted protein molecular weights, and exon-exon junctions assayed by qRT-PCR in (FIG. 1D).
Figure 5D:
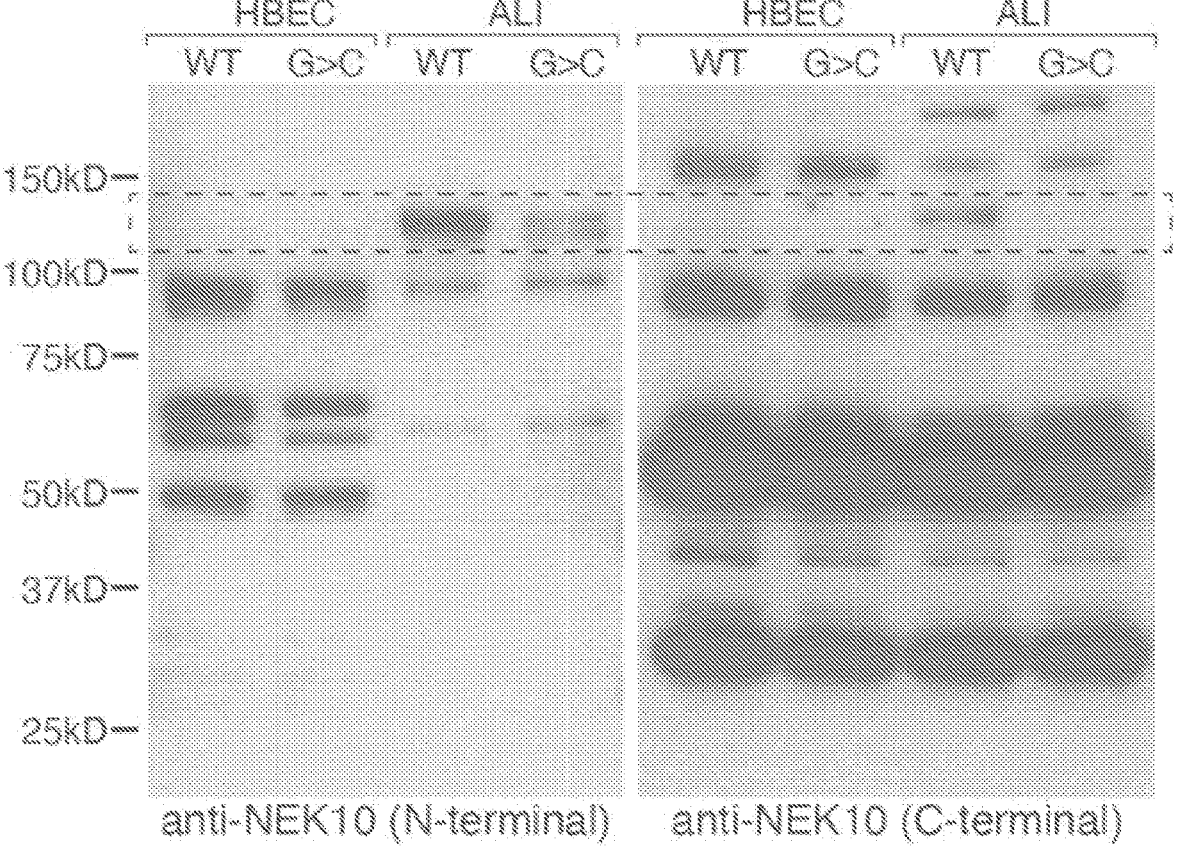
FIG. 5D includes a representative image from immunoblotting against indicated NEK10 epitopes; HBEC bands are non-specific, full-length 133 kDa NEK10 protein indicated with dashed box, representative of 3 experiments.

To study the effects of NEK10$^{G>C}$ in the lung, control and proband bronchial epithelial cells ("HBECs") obtained at the time of bilateral lung transplantation were isolated and cultured. Although NEK10 mRNA was robustly expressed in airway tissue it was essentially undetectable both in NEK10$^{WT}$ and NEK10$^{G>C}$ HBECs, suggesting its expression might be restricted to mature airway cells (FIG. 1D). Therefore, analysis was performed using differentiated control and patient-derived HBECs at an air-liquid interface (ALI), a well-validated method for generating airway epithelium in vitro (Fulcher et al. in Human Cell Culture Protocols 107, 183-206 (Humana Press, 2005)). Unexpectedly, both control and mutant ALI samples demonstrated robust NEK10 mRNA expression (FIG. 1D, FIG. 5C) despite immunoblotting evidence that NEK10$^{G>C}$ encodes a loss of function allele (FIG. 1E, FIG. 5D). To elucidate the mechanism by which NEK10$^{G>C}$ impairs protein expression, full-length cDNAs from mutant ALI was sequenced, revealing the mutation-dependent in-frame insertion of 7 amino acids, which could have rendered NEK10 unstable (FIG. 1F). To test this hypothesis, epitope-tagged NEK10 constructs were expressed in HEK293T cells, and it was found, as in ALI cultures, that the mutant protein was severely under-expressed—supporting a destabilizing effect of NEK10$^{G>C}$ causing loss-of-function (FIG. 1G).

Figure 1H:
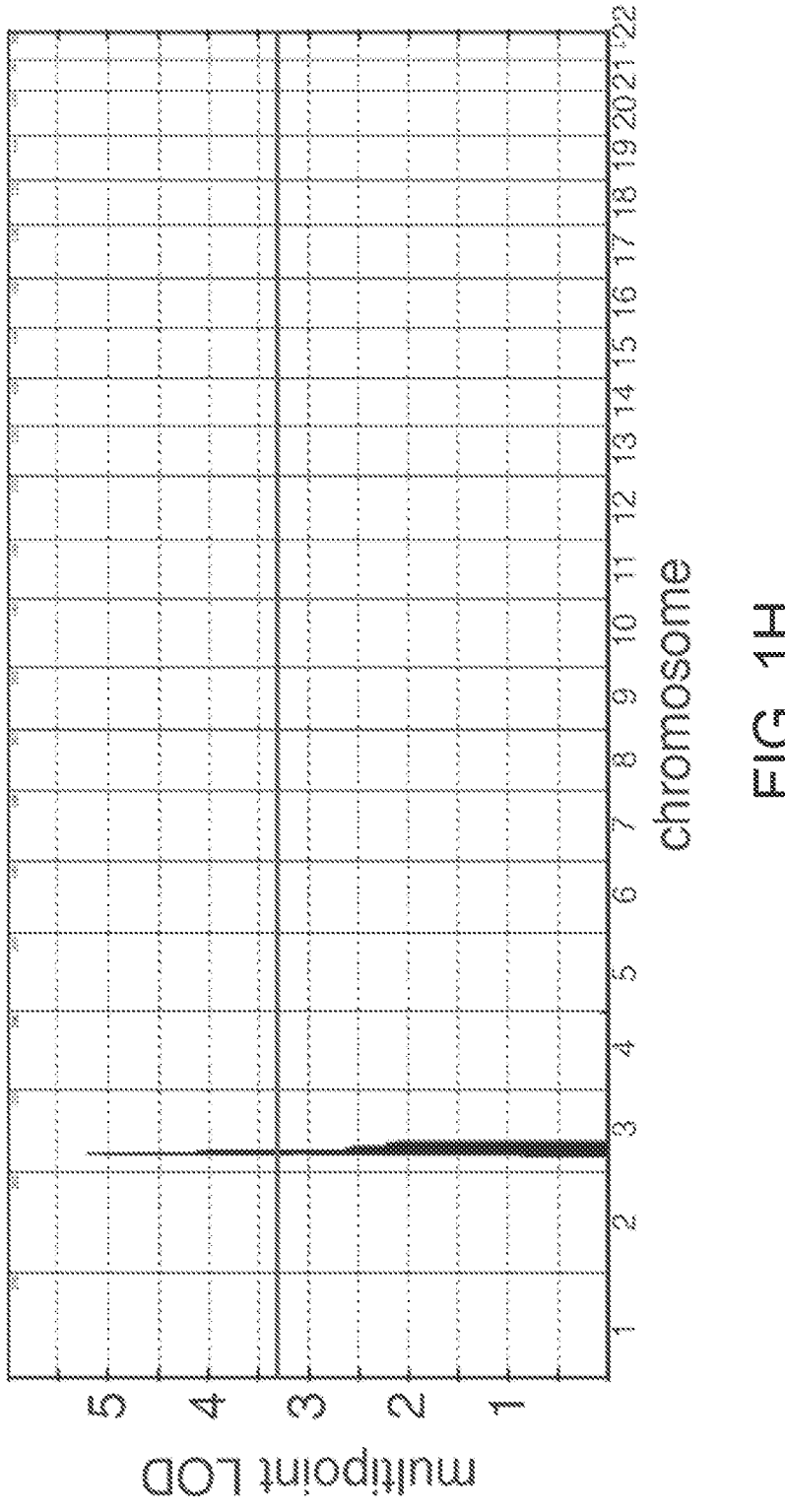

Further studies were performed to determine whether NEK10 mutations might underlie other cases of unexplained bronchiectasis. Indeed, further sequencing revealed 6 additional patients from 4 families harboring homozygous NEK10 mutation and exhibiting bronchiectasis (FIGS. 5E-5O). The first, an 11-year-old girl, had homozygous c.1869dupT mutation resulting in frameshift and premature stop (His624Serfs*4). The second, a 15-year-old girl, had homozygous c.2243C>T mutation causing substitution of leucine for a highly conserved proline (Pro748Leu) within the kinase domain. The third, a 23-year-old woman, had homozygous c.1373+1G>T mutation causing exon skipping, frameshift, and premature stop (Cys437Thrfs*9). The fourth, fifth, and sixth were siblings with homozygous c.2317C>T mutation resulting in mutation of a highly conserved arginine to cysteine (Arg773Cys). Notably, clinical assays revealed normal nasal ciliary ultrastructure by EM, normal nasal nitric oxide (nNO) levels, no evidence of heterotaxy, and only very subtle abnormalities by clinical high-speed video-microscopy (HSVM) in all tested individuals, suggesting such patients might escape detection during standard PCD evaluation (Knowles et al. Primary Ciliary Dyskinesia. *Clinics in Chest Medicine* 37, 449-461 (2016)) (Table 2). Linkage analysis incorporating kindreds 1-3 yielded a single, highly significant genome-wide linkage signal (pLOD 5.2), defining a 7.3 Mb interval which includes the NEK10 locus (FIG. 1H). Conversely, healthy individuals with biallelic inactivating NEK10 mutation are completely absent from publicly available variant databases (Karczewski et al. Variation across 141,456 human exomes and genomes reveals the spectrum of loss-of-function intolerance across human protein-coding genes. *bioRxiv* 49, 531210 (2019)).

Together, these data provide strong genetic and clinical evidence that NEK10 represents a novel and bonafide autosomal recessive bronchiectasis locus

TABLE 2

Clinical Characteristics of Bronchiectasis Patients Harboring Biallelic NEK10 Mutations.

| | Patient | | | | | | | | |
|---|---|---|---|---|---|---|---|---|---|
| | 1 | 2 | 3 | 4 | 5 | 6 | 7 | 8 | 9 |
| Kindred | 1 | 1 | 1 | 2 | 3 | 4 | 5 | 5 | 5 |
| Individual | 1 | 2 | 3 | 1 | 1 | 1 | 1 | 2 | 3 |
| Mutation | c.1230 + 5G > C | c.1230 + 5G > C | c.1230 + 5G > C | c.1869dupT | c.2243C > T | c.1373 + 1G > T | c.2317C > T | c.2317C > T | c.2317C > T |
| Mutation copy number | homozygous | homozygous | homozygous | homozygous | homozygous | homozygous | homozygous | homozygous | homozygous |
| Mutation effect | insertion, protein de-stabilization | insertion, protein de-stabilization | insertion, protein de-stabilization | frameshift, premature stop | kinase domain Pro -> Leu missense | exon skipping, premature stop | Arg -> Cys missense | Arg -> Cys missense | Arg -> Cys missense |
| Sex | F | F | M | F | F | F | F | F | F |
| Age at evaluation | 31 | 27 | 8 | 11 | 15 | 23 | 31 | 29 | 26 |
| Neonatal respiratory distress? | yes | no | no | not reported | not reported | yes | no | no | no |
| Situs | solitus | solitus | solitus | solitus | solitus | solitus | solitus | solitus | solitus |
| CT findings | multi-lobar bron-chiectasis (RML, RLL, lingula, LLL) | multi-lobar bron-chiectasis (RML, RLL, lingula, LLL) | RML bron-chiectasis | RML bron-chiectasis by CXR, CT refused | multi-lobar bron-chiectasis (LLL, RML, RLL, lingula) | multi-lobar bron-chiectasis (RML, LLL) | multi-lobar bron-chiectasis (LLL, RML, lingula) | multi-lobar bron-chiectasis (RML, RLL, LLL) | multi-lobar bron-chiectasis (RLL, LLL, RML, lingula) |
| Upper airway symptoms | yes, recurrent sinusitis | yes, recurrent sinusitis | mild | yes, recurrent sinusitis | yes, recurrent sinusitis | yes, chronic rhinosinusitis with otitis | yes, recurrent sinusitis | yes, recurrent sinusitis, childhood otitis | yes, recurrent sinusitis |
| Nasal NO | unavailable | unavailable | unavailable | unavailable | unavailable | normal (250 nl/min) | normal (428 nl/min) | normal (328 nl/min) | normal (339 nl/min) |
| CF testing | normal (by genetic testing) | normal (by sweat test) | normal (by sweat test) | normal (by sweat test and sequencing) | normal (by sweat test) | normal (by sweat test) | normal (by genetic testing) | normal (by genetic testing) | normal (by genetic testing) |
| HSVM | unavailable | unavailable | unavailable | unavailable | unavailable | nearly normal; subtle beating defect with slightly reduced beating amplitude; normal CBF | Vigorous beat, subtle waveform defect with slightly reduced amplitude, and very mild dys-coordination; normal CBF | | |
| FEV1 (% p) | reduced, 28% p | reduced, 60% p | unavailable | unavailable | reduced | normal | reduced, 90% p | reduced, 87% p | reduced, 86% p |
| FVC (% p) | reduced, 35% p | reduced, 71% p | unavailable | unavailable | reduced | normal | reduced, 99% p | reduced, 89% p | reduced, 85% p |
| Clinical TEM | normal | unavailable | unavailable | unavailable | unavailable | normal | normal | normal | normal |
| Respiratory pathogens | P. aeruginosa, M. avium | P. aeruginosa | no microbiology available | H. influenzae | H. influenzae | H. influenzae | S. aureus, P. aeruginosa, H. infuenzae | S. aureus, M. avium | S. aureus, P. aeruginosa, H. infuenzae |

Figure 6G:
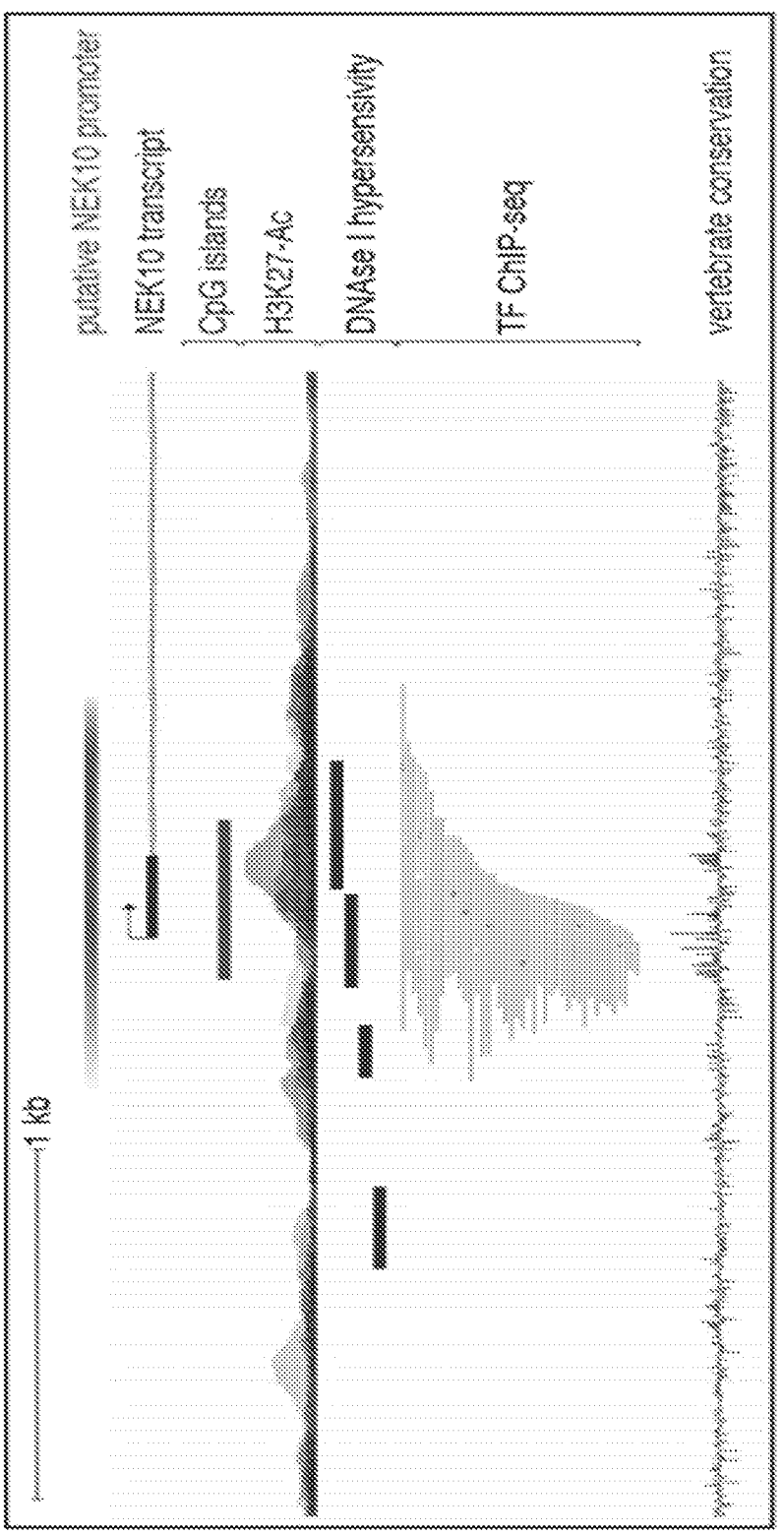
Figure 6H:
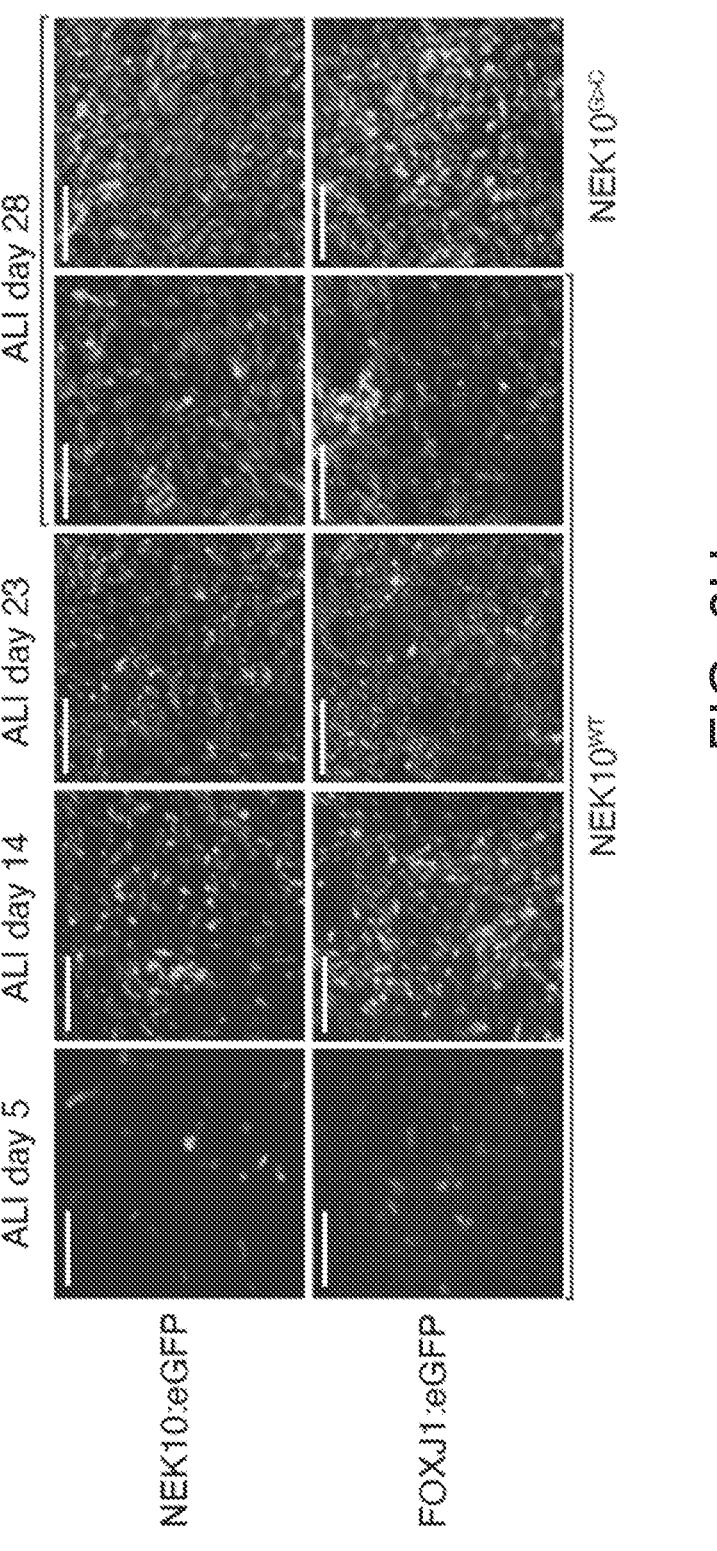

Example 2: NEK10 is a Ciliated Cell-Specific Gene Required for Effective Mucociliary Transport Given NEK roles in cell cycle regulation, it was initially hypothesized that NEK10 is required for the specification of one or more cell types involved in mucociliary clearance. Quantitative reverse-transcriptase PCR (qRT-PCR) revealed that NEK10 is robustly induced during airway epithelial differentiation, coincident with the acquisition of markers for ciliated and secretory cells and the depletion of stem cell markers (FIGS. 6A-6D). However, NEK10$^{G>C}$ cultures induced and repressed these markers with identical kinetics as control and produced similar numbers of secretory, gob-let, and multiciliated cells (MCCs, FIGS. 6E-6F). These data suggested NEK10 might instead function specifically within one of the specialized cells important for mucociliary clear-ance. To elucidate its expression domain, ALI cultures in which eGFP is expressed under the control of the NEK10 promoter (NEK10:eGFP) were generated. The NEK10 pro-moter directs expression within a subset of ALI cells in a differentiation-dependent manner (FIGS. 6G-6I). FACS-pu-rified GFP+ cells from mature NEK10:eGFP ALI revealed a 149-fold enrichment of the MCC marker FOXJ114 with reciprocal depletion of secretory and basal cell marker transcripts (FIG. 2A), while confocal imaging confirmed GFP positivity restricted to cells harboring apical cilia (FIG. 2B). Conversely, FACS-purified ciliated cells from FOXJ1: eGFP ALI enriched NEK10 152-fold (FIGS. 6H-6I, FIG.

2A). These findings establish NEK10 as a ciliated cell-specific gene in human airway induced during, but dispensable for, differentiation of this cell type.

Figure 2C:
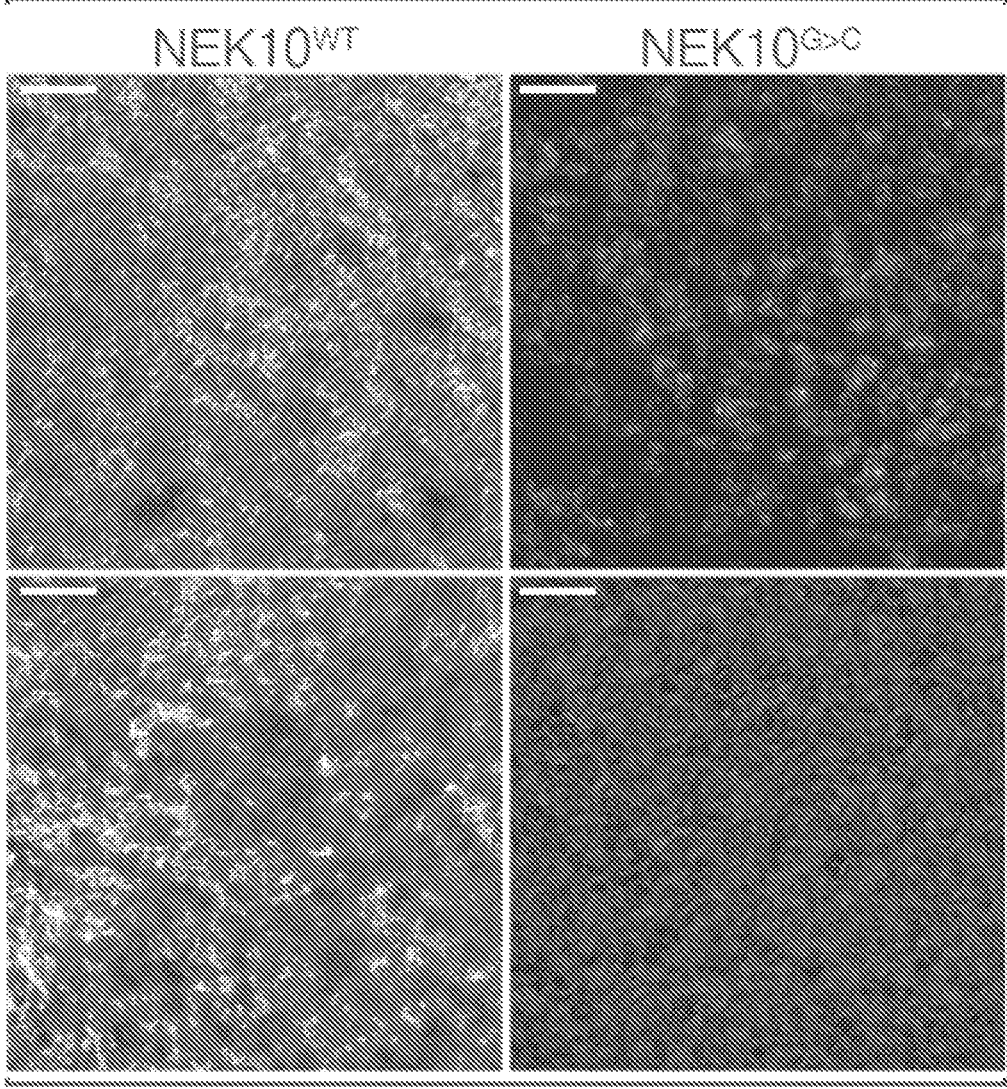
Figure 2F:
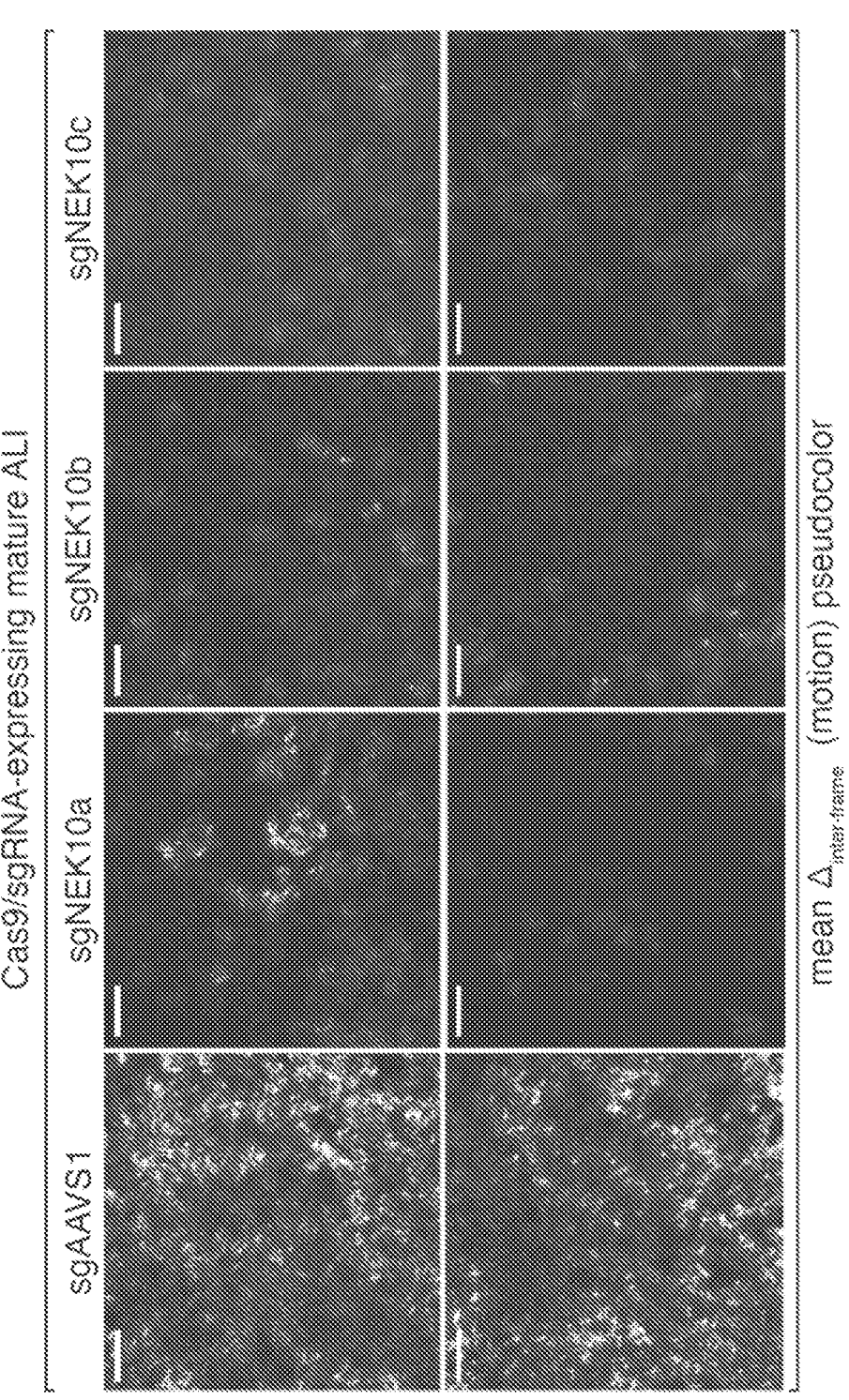

To explore what functional roles NEK10 plays in MCCs, live ALI cultures were imaged with high-framerate phase contrast microscopy, exposing a striking reduction in overall ciliary motion in NEK10$^{G>C}$ cultures (FIG. 2C, FIG. 7A). Given this abnormality, advanced MCC functional phenotyping was performed using micro-optical coherence tomography (μOCT), a state of the art high-resolution live imaging technique capable of quantitatively interrogating multiple ciliary parameters (Liu et al. Method for Quantitative Study of Airway Functional Microanatomy Using Micro-Optical Coherence Tomography. *PLoS ONE* 8, e54473 (2013)). Unlike control cultures, which robustly transport polystyrene beads added to the apical ALI surface, near-absence of mucociliary transport (MCT) in NEK10$^{G>C}$ ALI (FIG. 2D, FIG. 7B) was noted, as well as reduction in depth of the periciliary liquid layer (PCL, FIG. 2E). Surprisingly, normal ciliary beat frequency in mutant ALI (FIG. 7C) was measured, again suggesting a mode of dysfunction distinct from classical PCD. While these data suggested a causative role for NEK10 loss-of-function in MCC dysfunction, they could not rule out that secondary genetic or acquired changes in proband-derived cells were in fact responsible (Knowles et al. Primary Ciliary Dyskinesia. Recent Advances in Diagnostics, Genetics, and Characterization of Clinical Disease. *Am. J. Respir. Crit. Care Med.* 188, 913-922 (2013)). Therefore, CRISPR/Cas9-mediated NEK10 loss-of-function ALI cultures ("NEK10$^{KO}$" hereafter) were generated by genetically disrupting the NEK10 locus in wild-type HBECs. Immunoblotting confirmed efficient depletion of NEK10 while live microscopy of NEK10$^{KO}$ ALI revealed, as in NEK10$^{G>C}$, a dramatic reduction in ciliary motion (FIG. 2F, FIGS. 7D-7E). NEK10$^{KO}$ ALI were also subjected to μOCT imaging, and severe reduction in maximal particle transport velocity and thinning of the PCL, again without change in CBF (FIGS. 2G-2H, FIG. 7F), was found.

Figure 2J:
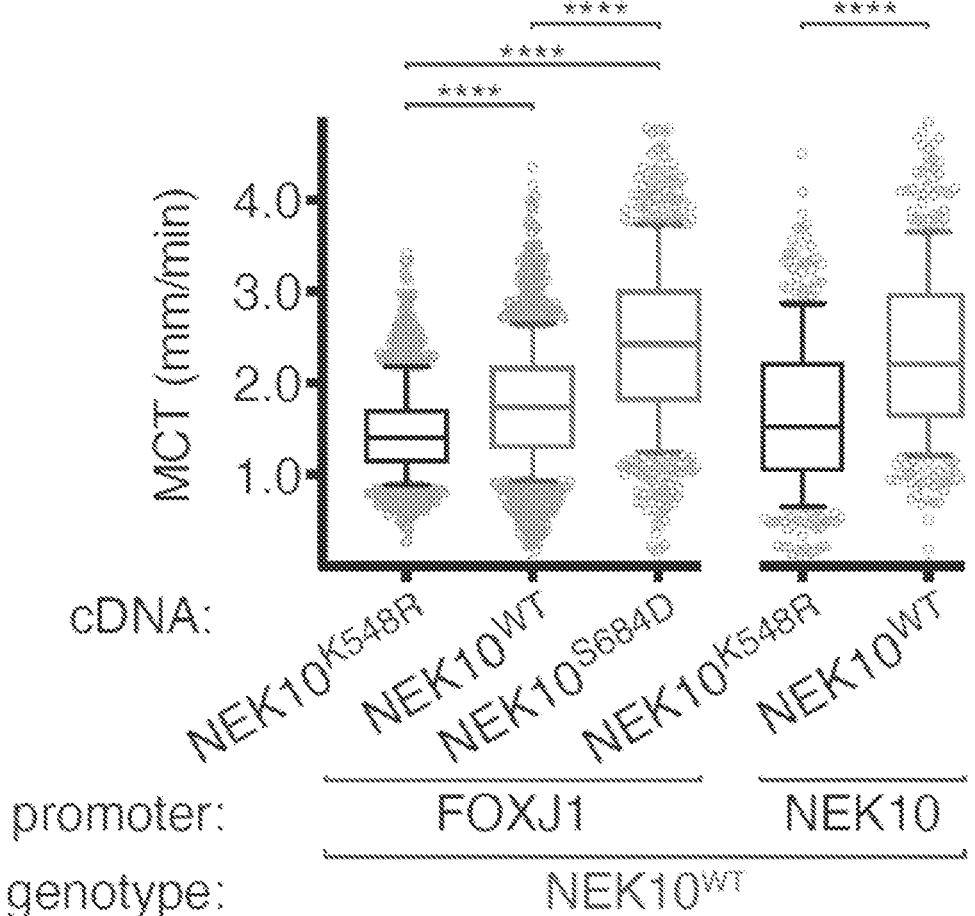

Given a recent report of catalysis-independent roles for NEKs (He et al. NEK7 is an essential mediator of NLRP3 activation downstream of potassium efflux. *Nature* 530, 354-357 (2016)), studies were performed to understand whether kinase activity per se is necessary for NEK10 function in MCCs. Therefore, NEK0G>C ALI were generated with FOXJ1 promoter-driven re-expression of NEK10$^{WT}$ or, alternatively, point mutants predicted to inactivate (NEK10$^{K548R}$) (Carrera et al. The conserved lysine of the catalytic domain of protein kinases is actively involved in the phosphotransfer reaction and not required for anchoring ATP. *PNAS* 90, 442-446 (1993)) or putatively hyperactivate (NEK10$^{S684D}$, NEK10$^{Y590A}$) activity based on prior studies of paralogous NEK kinases (Moniz et al. Nek family of kinases in cell cycle, checkpoint control and cancer. *Cell Division* 2011 6:1 6, 18 (2011); Moniz L Characterization of NimA-related Kinase 10 (NEK10): A Role in Checkpoint Control (2010); and Richards et al. An Autoinhibitory Tyrosine Motif in the Cell-Cycle-Regulated Nek7 Kinase Is Released through Binding of Nek9. *Mol Cell* 36, 560-570 (2009)). Despite sub-physiological expression of transduced NEK10 variants, live microscopy demonstrated a striking increase in motility upon expression of NEK10$^{S684D}$ partial rescue with NEK10$^{WT}$ and NEK10$^{Y590A}$, but no effect with catalytic-dead NEK10$^{K548R}$ (FIG. 7G-7I). μOCT demonstrated that CBF was again unaffected by NEK10 status but that particle transport was significantly increased upon expression of NEK10$^{S684D}$ (FIG. 2I, FIG. 7J). Experiments were performed to determine whether ectopic activation of NEK10 signaling in wild-type ALI cultures could augment mucociliary transport to supraphysiological levels. Indeed, expression of NEK10$^{WT}$ or NEK10$^{S684D}$ under the control of the FOXJ1 promoter significantly increased transport velocity compared to catalytic-dead NEK10K$^{548R}$, a phenotype also reproduced with the more transcriptionally active NEK10 promoter (FIG. 2J).

Together, these data establish (1) a ciliated cell-specific NEK10 kinase activity requirement for effective airway mucociliary transport, (2) that NEK10 activity is constrained by the serine 684 activation loop residue, and (3) that potentiating NEK10 activity may represent a strategy for augmenting mucociliary transport.

Figure 3E:
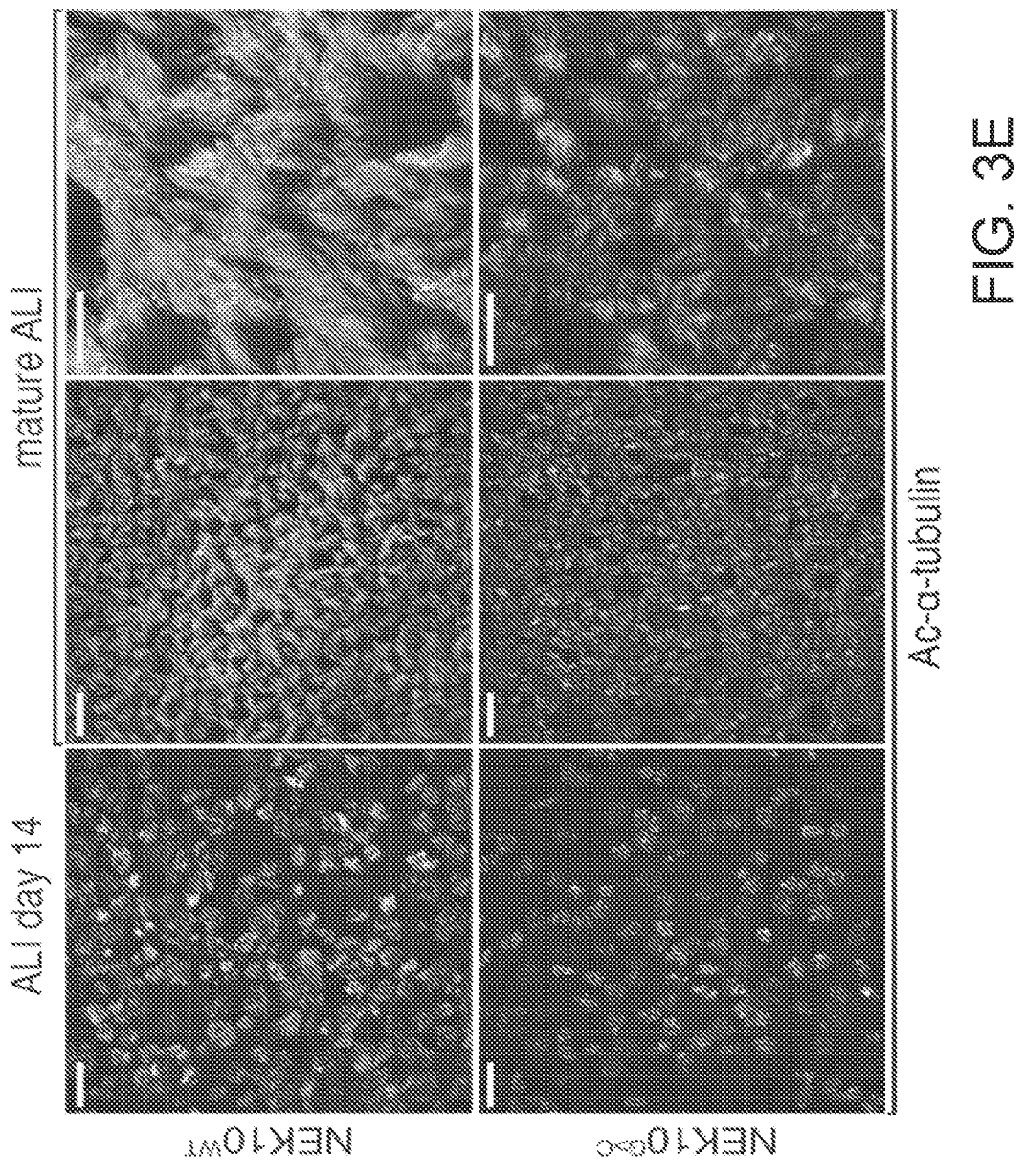
Figure 8A:
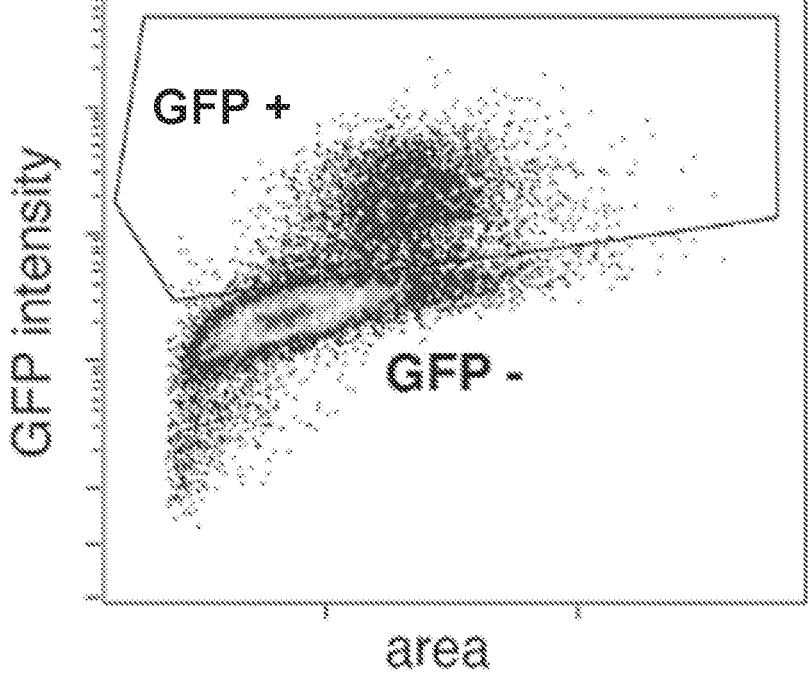
FIGS. 8A-8E include data showing that experimental manipulation of NEK10 activity alters ciliated cell morphology.
Figure 8B:
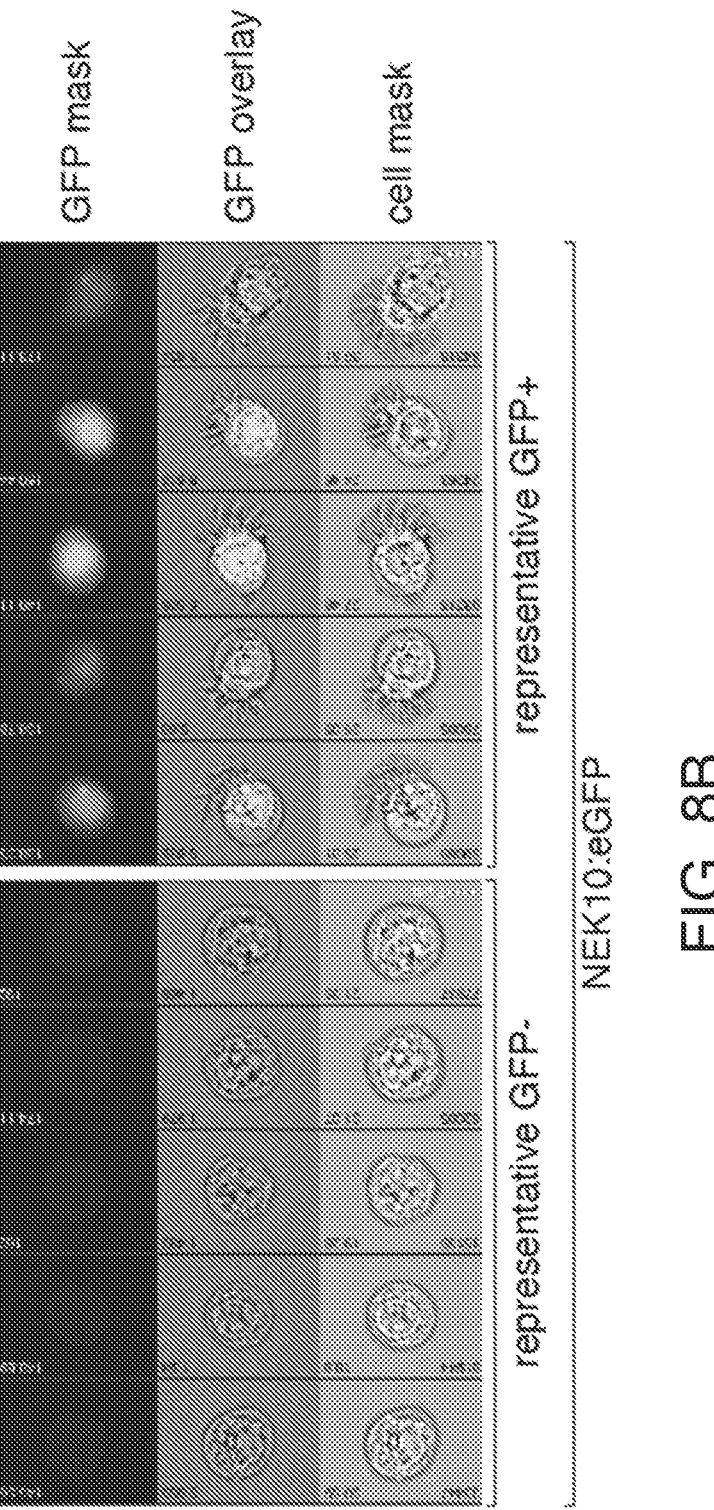
Figure 8C:
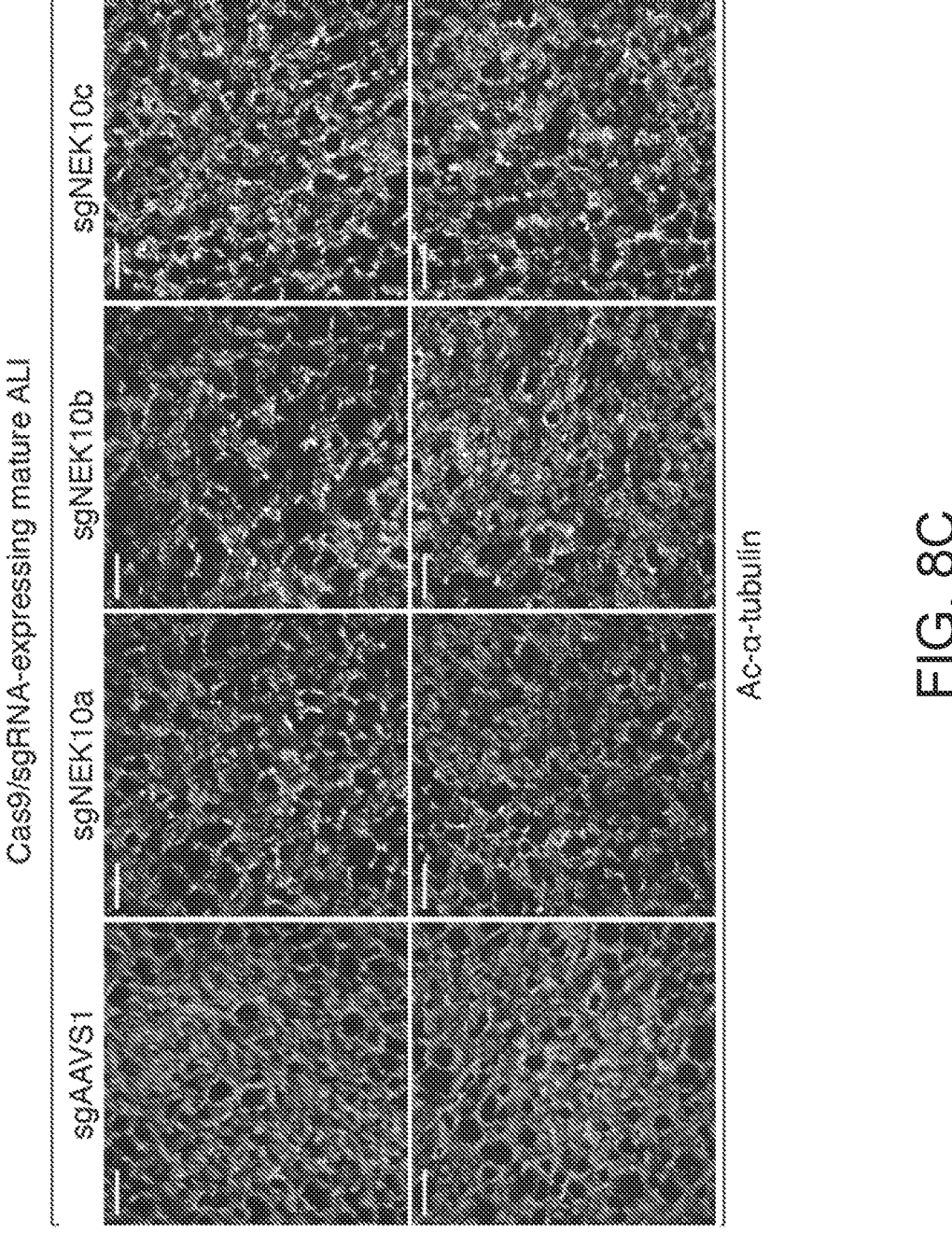
Figure 8D:
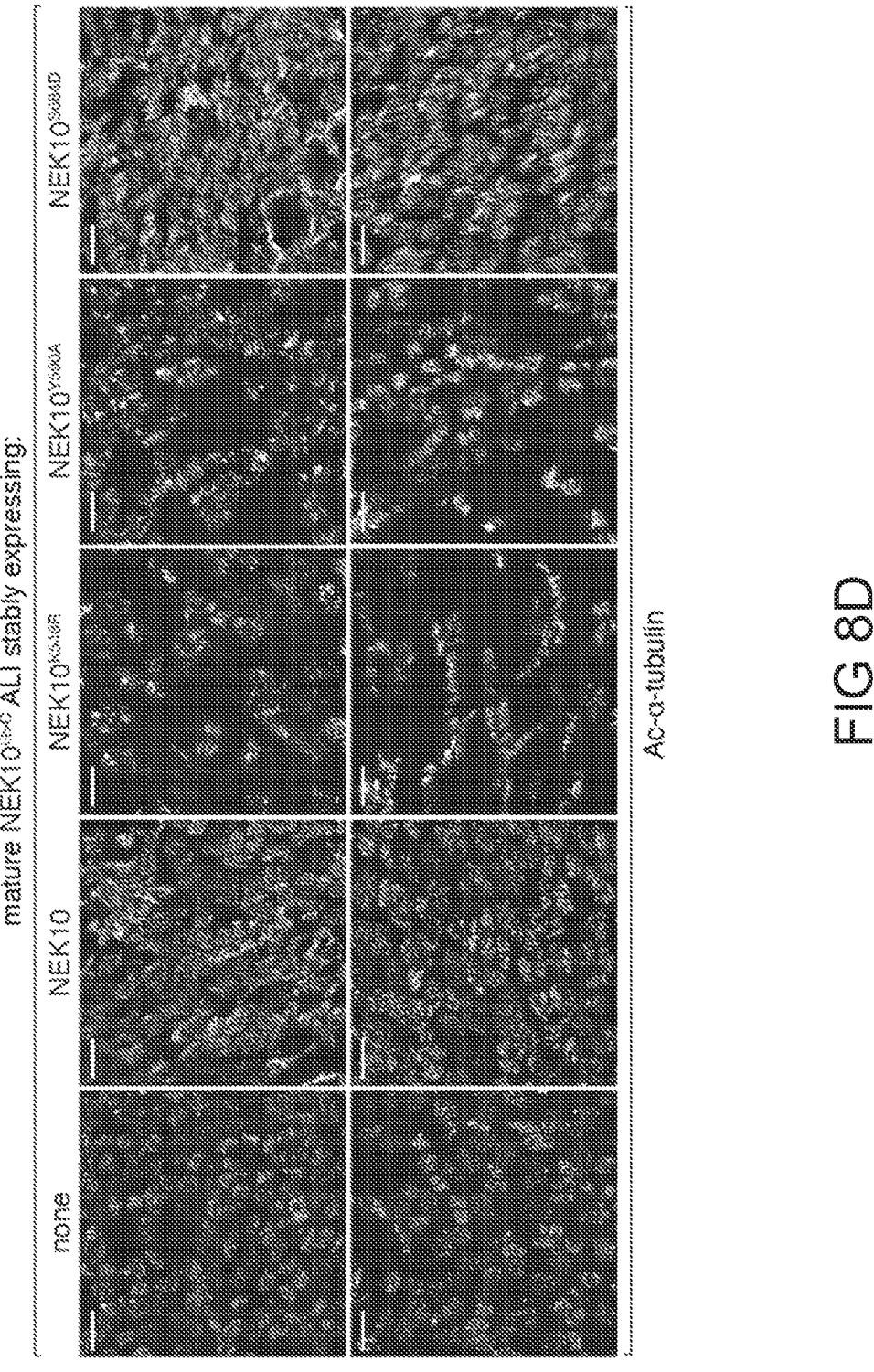

Example 3: Morphologically Abnormal Ciliated
Cells are Present in NEK10-Deficient Airways Next, studies were performed to understand the mechanisms by which NEK10 regulates MCC function. To evaluate whether mutant MCCs harbor some physical abnormality, mutant MCCs were analyzed using imaging flow cytometry (IFC), which allows the capture of thousands of single cells for statistically robust morphology analysis (Doan et al. Diagnostic Potential of Imaging Flow Cytometry. *Trends in Biotechnology* 36, 649-652 (2018)). After gating singlet MCCs from NEK10:eGFP ALI (FIGS. 8A-8B) per-cell ciliary area as well as ciliary zone thickness were measured, revealing a clear and statistically significant reduction in both parameters in mutant MCCs (FIGS. 3A-3C). Representative single cells corroborated this finding, demonstrating a hypoplastic ciliary layer in NEK10$^{G>C}$ MCCs (FIG. 3D). To validate this finding using an orthogonal method, NEK10$^{G>C}$ ALI were subjected to confocal IF against acetylated α-tubulin. Again, it was found that mutant ALI harbored strikingly abnormal, hypoplastic-appearing cilia (FIG. 3E). NEK10$^{KO}$ ALI phenocopied this morphology while NEK10$^{S684D}$-complemented NEK10$^{G>C}$ ALI reversed it (FIGS. 8C-8D), indicating this phenotype is specifically attributable to NEK10 kinase activity.

Figure 3F:
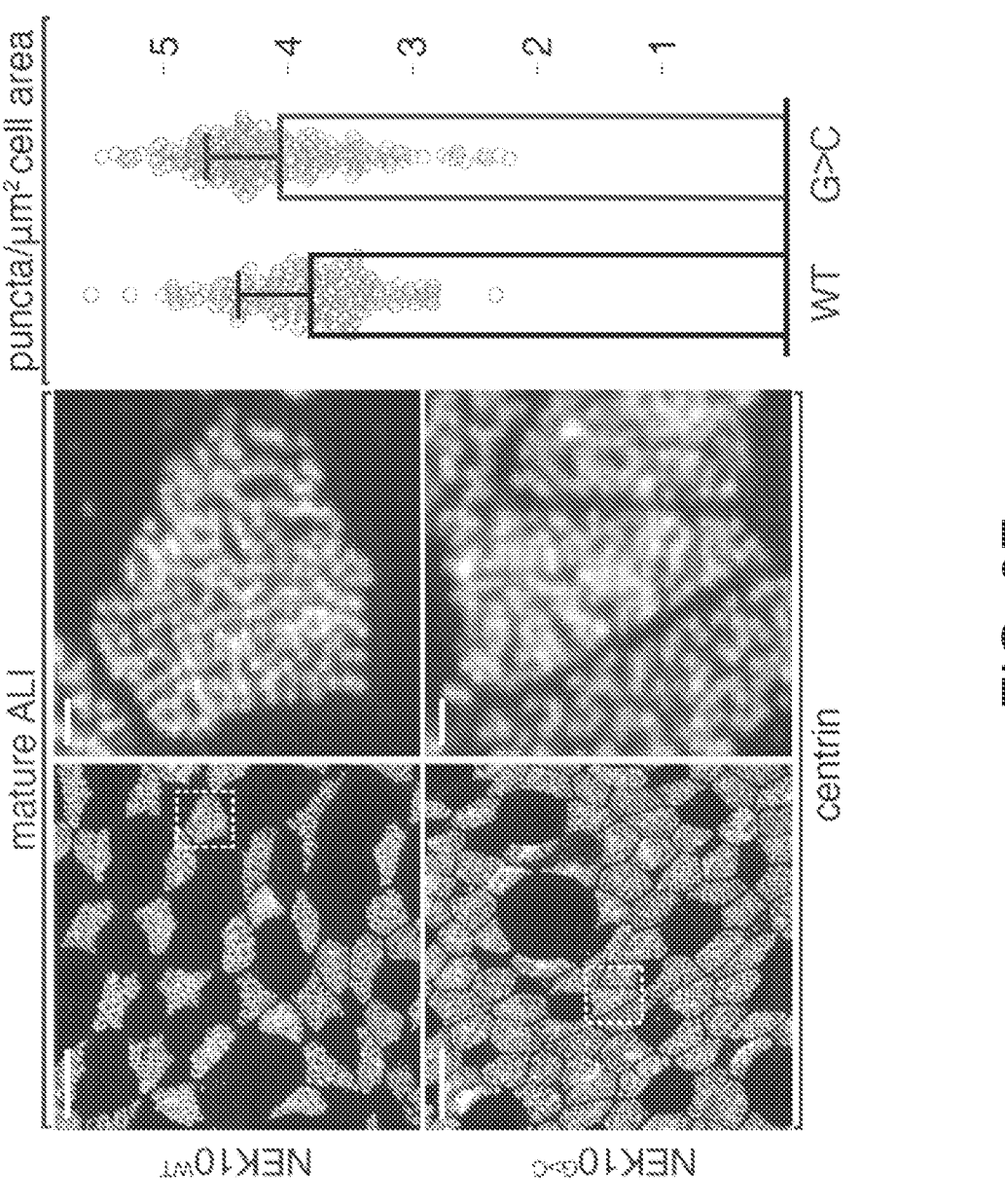
Figure 3G:
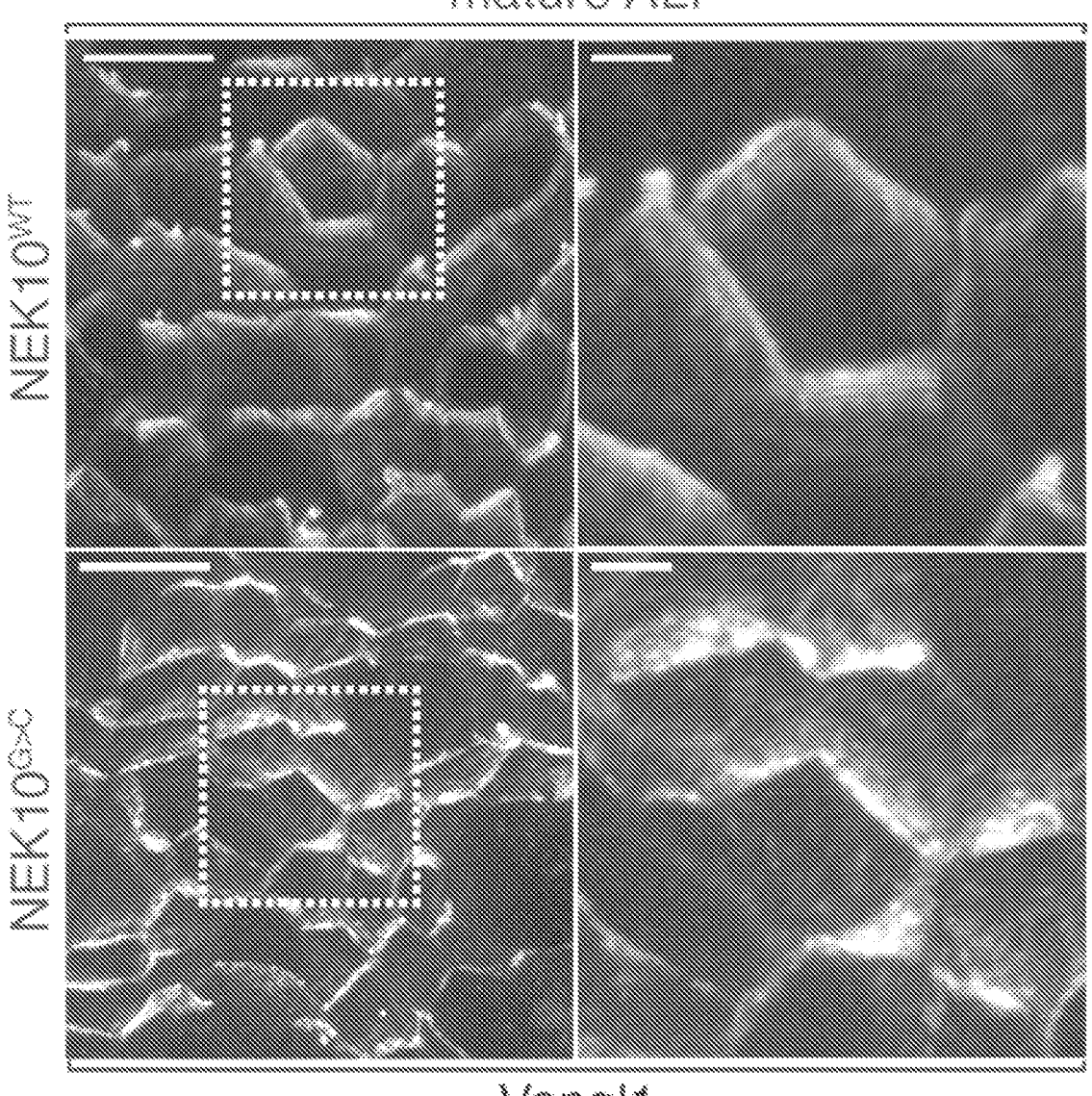
Figure 3H:
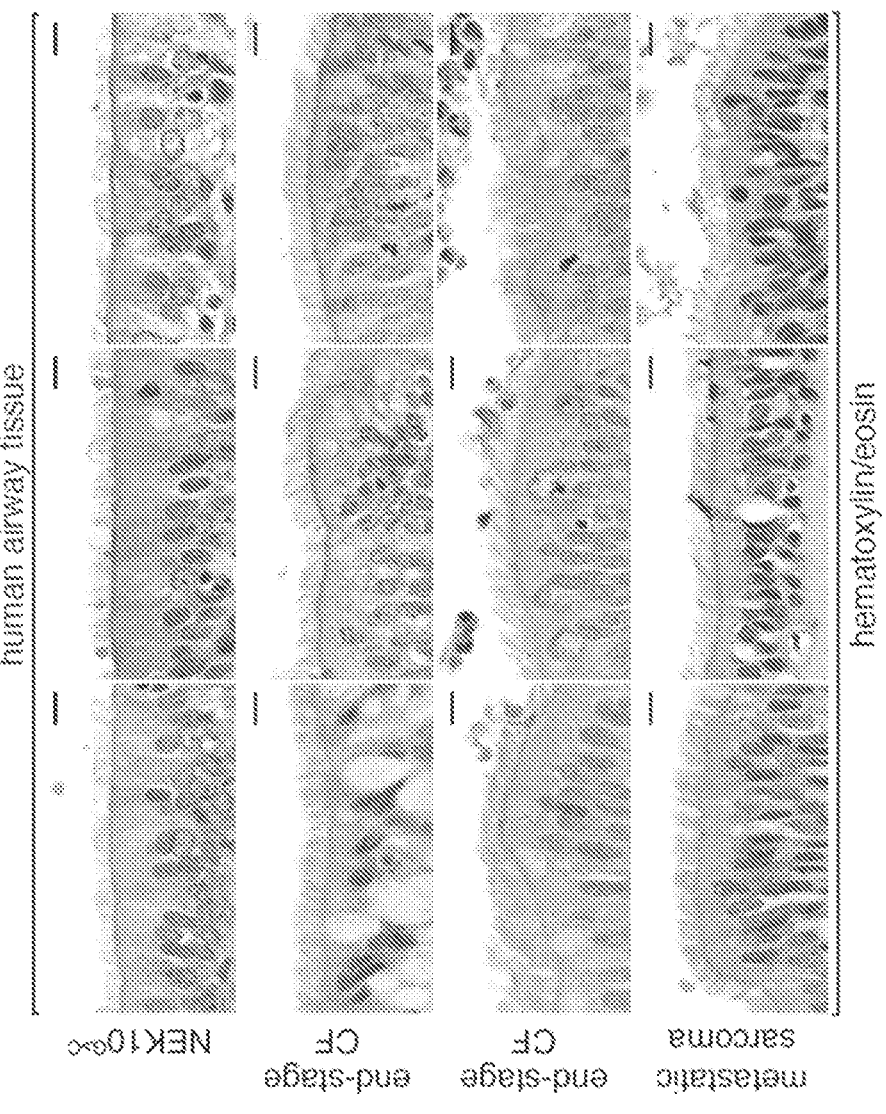
Figure 8E:
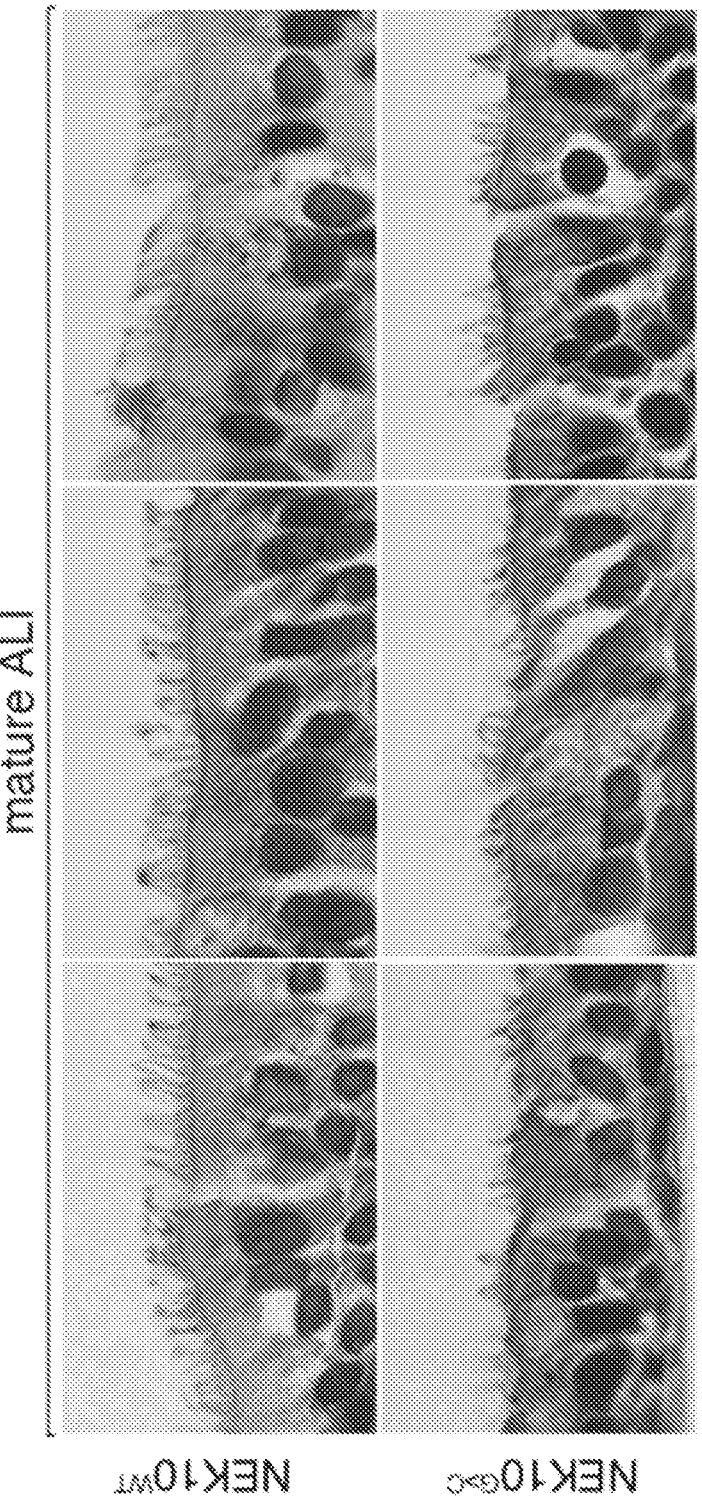

Previously described human mutations (Wallmeier et al. Mutations in CCNO result in congenital mucociliary clearance disorder with reduced generation of multiple motile cilia. *Nat Genet* 46, 646-651 (2014); and Boon et al. MCIDAS mutations result in a mucociliary clearance disorder with reduced generation of multiple motile cilia. *Nat Comms* 5, 4418 (2014)) are known to impair the nucleation and density of motile cilia, and therefore MCC basal body density was evaluated by IF, but no reduction was found to account for the NEK10$^{G>C}$ phenotype (FIG. 3F). In light of links between planar cell polarity (PCP) and ciliogenesis (Vladar et al. Airway epithelial homeostasis and planar cell polarity signaling depend on multiciliated cell differentiation. *JCI Insight* 1, 183 (2016)), it was also confirmed that NEK10 activity is dispensable for MCC planar polarization (FIG. 3G). Finally, in order to validate ALI culture findings in human patients, airway tissue from the explanted lungs of the proband was compared with airway from non-bronchiectatic as well as end-stage CF patients. As in ALI cultures (FIG. 8E), histological analysis revealed ciliary hypoplasia only in NEK10 mutant airway (FIG. 3H)—indicating this phenotype does not reflect a non-specific consequence of severe bronchiectasis and suggesting that NEK10 deficiency produces short motile cilia in vivo, a previously undescribed human genetic phenotype.

Figure 9A:
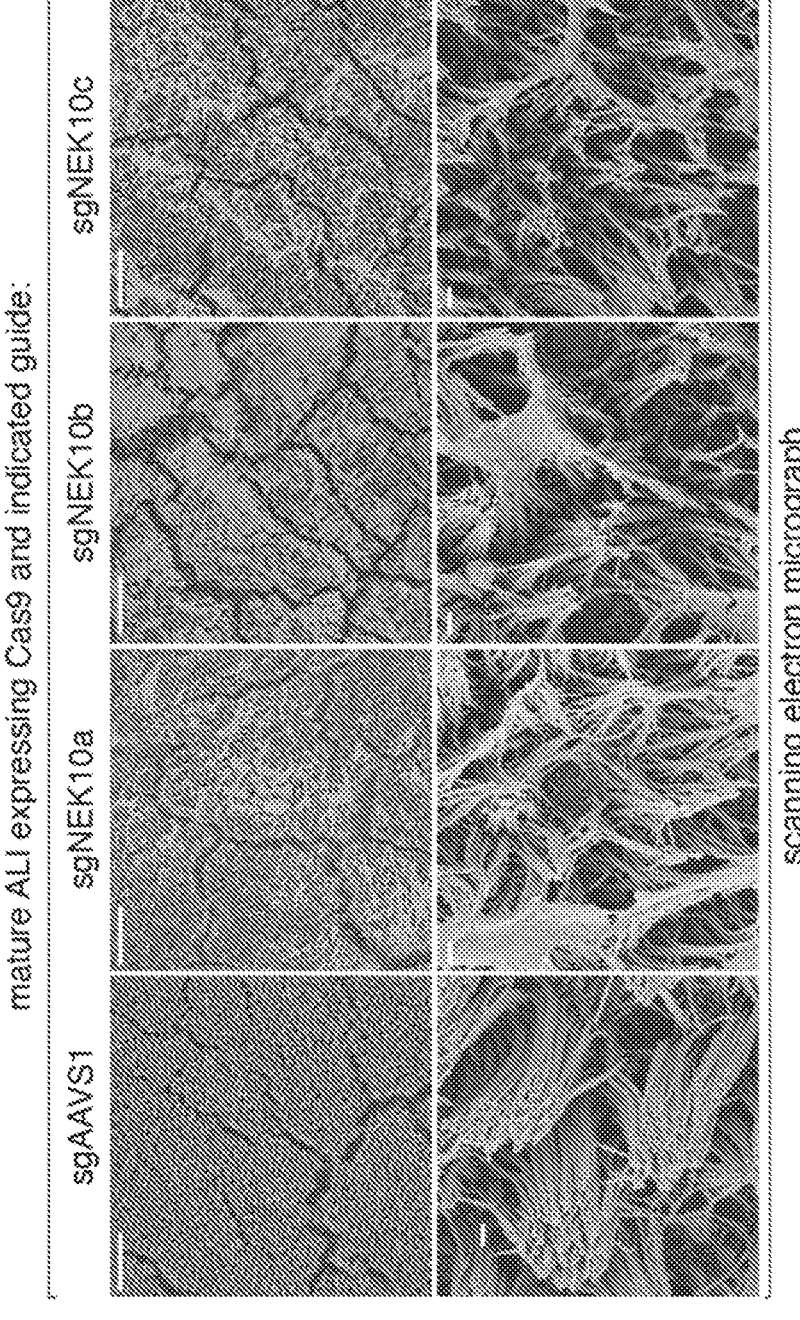
Figure 9B:
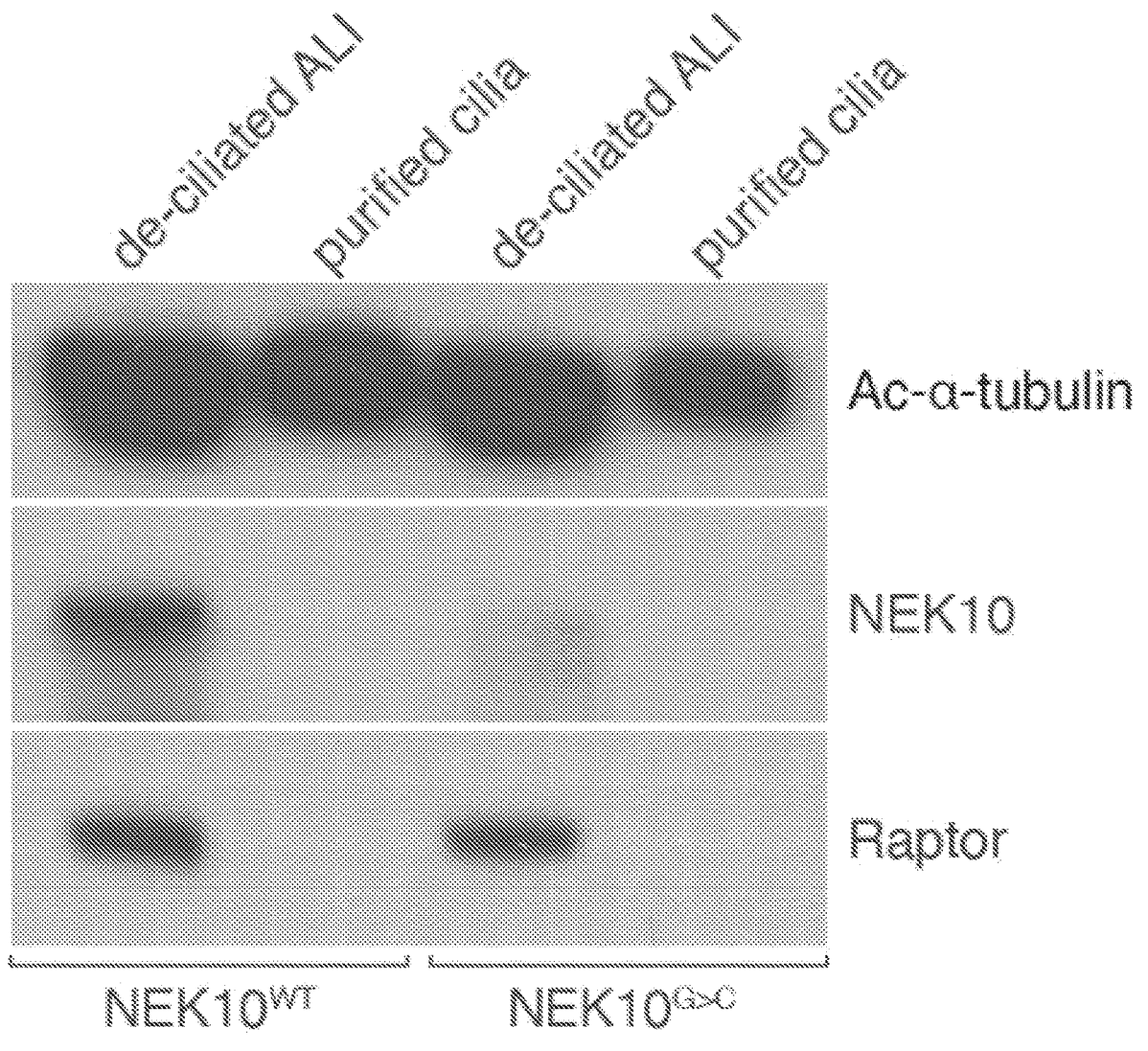
Figure 9C:
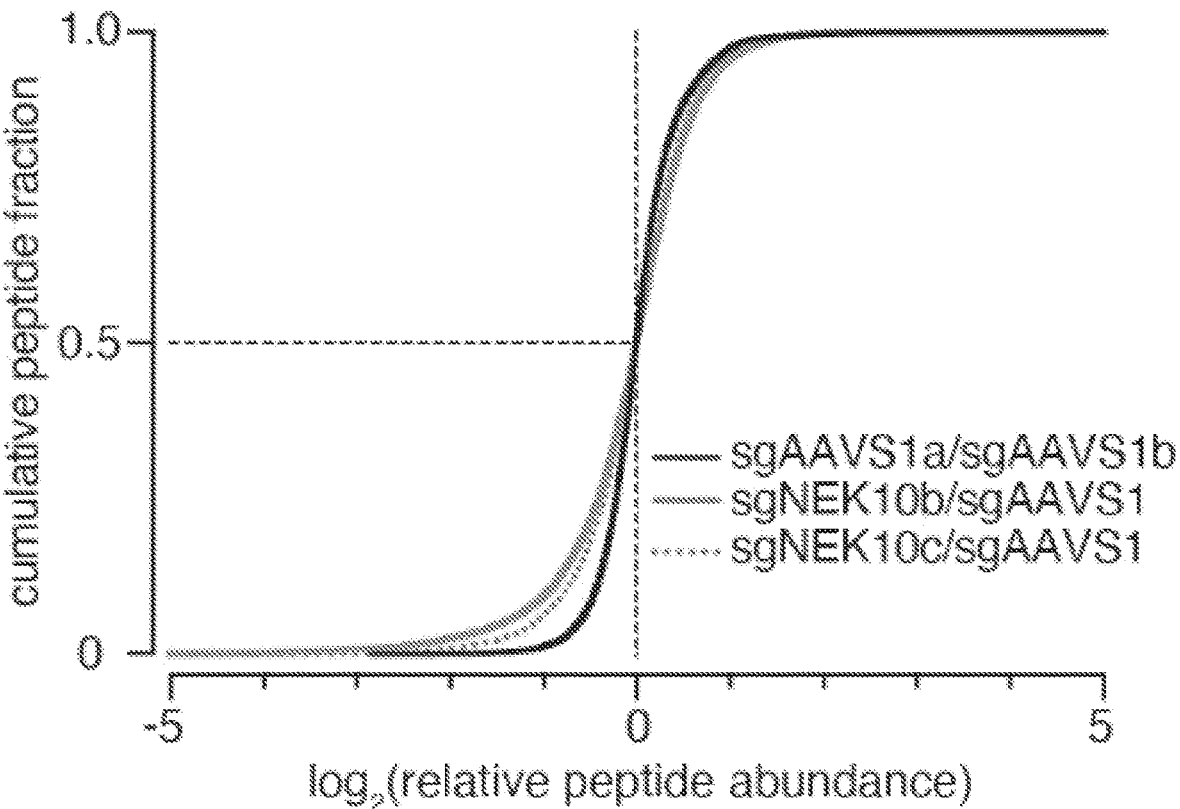
Figure 9E:
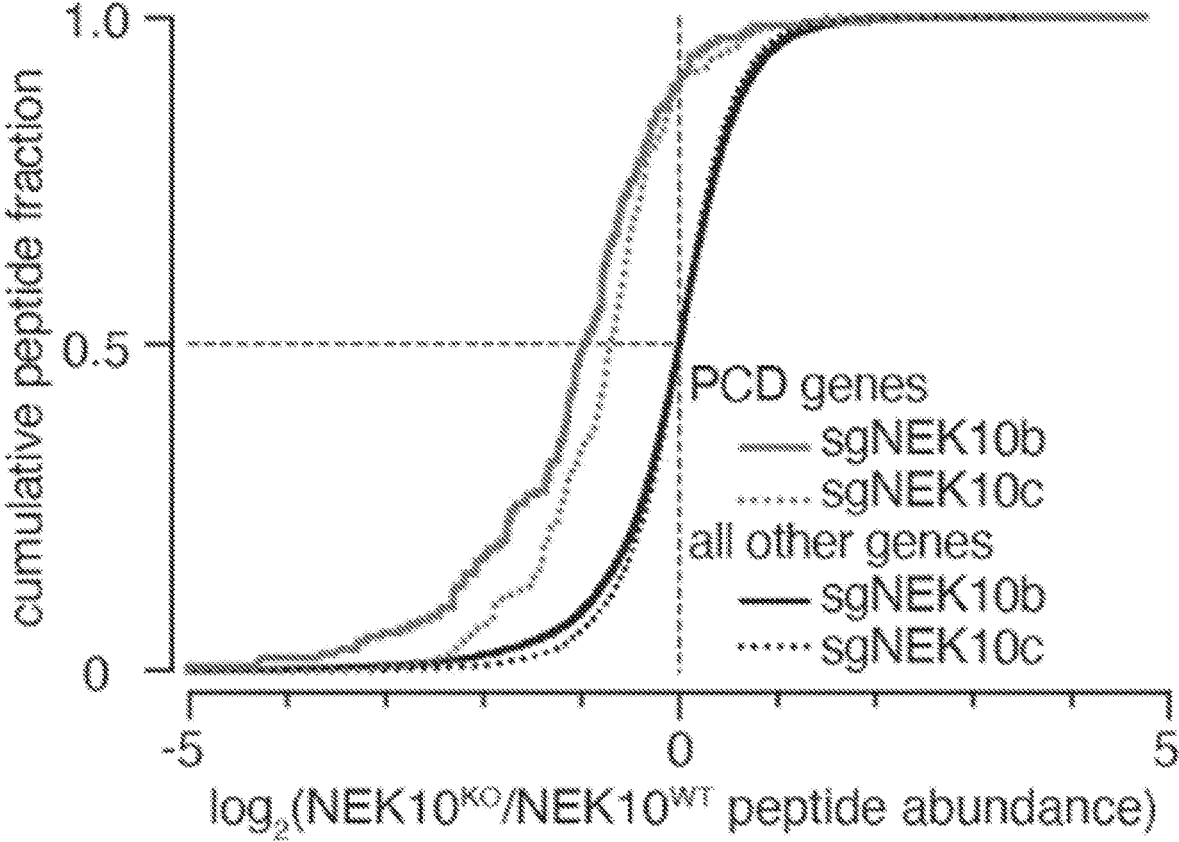
Figure 9F:
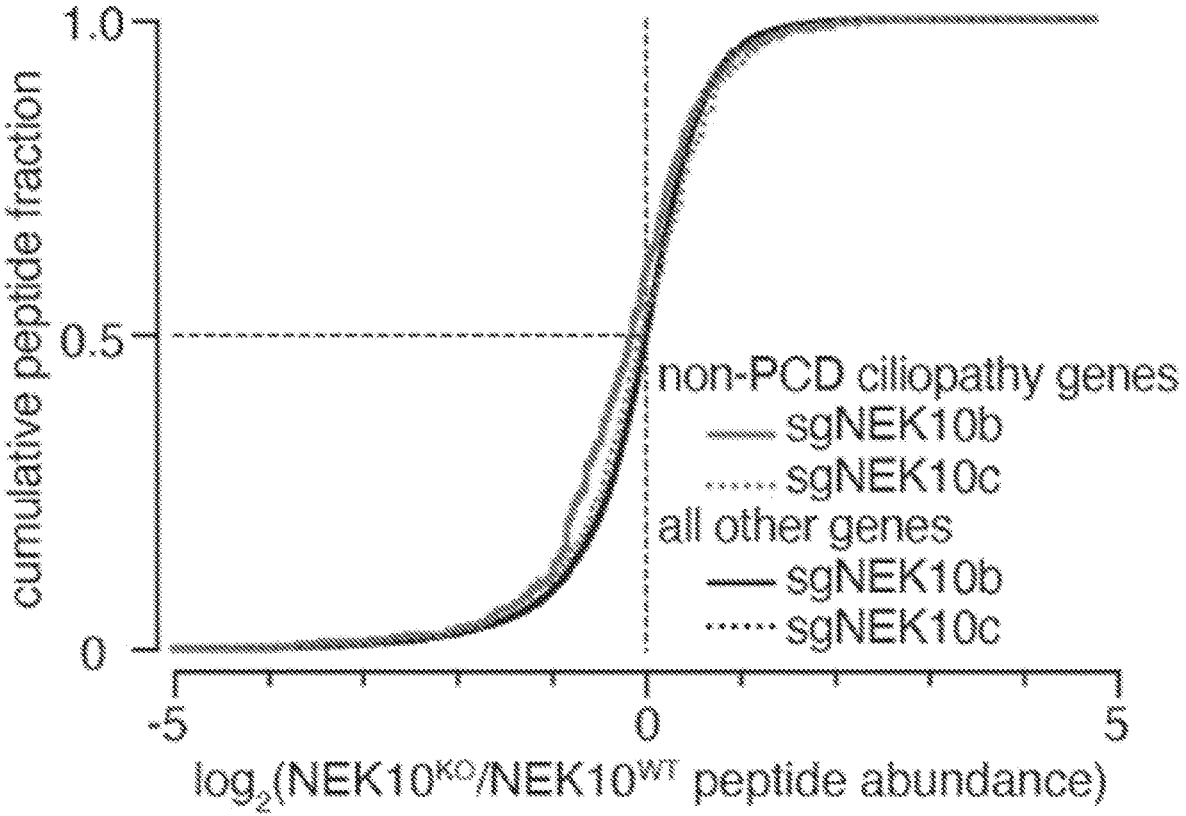

Example 4: NEK10 Regulates Ciliary Length Through Widespread Effects on the Ciliary Proteome As the size of motile cilia limits their structural analysis by light microscopy, ALI preparations were next subjected to 3 complementary modes of electron microscopic (EM) analysis. Scanning electron microscopy (SEM) of intact ALI, like IF, revealed NEK10$^{G>C}$ and NEK10$^{KO}$ ALI to harbor morphologically abnormal cilia of heterogeneous length with excess mucus accumulation (FIG. 4A, FIG. 9A). EM imaging of sectioned ALI cultures revealed an evident decrease in ciliary length in NEK10$^{G>C}$ ALI (FIG. 4B), but not undocked centrioles as in ciliary aplasia syndromes or ciliary tip "ballooning" as reported with certain intraflagellar transport (IFT) defects (Wallmeier et al. Mutations in CCNO result in congenital mucociliary clearance disorder with reduced generation of multiple motile cilia. *Nat Genet* 46, 646-651 (2014); and Boon et al. MCIDAS mutations result in a mucociliary clearance disorder with reduced generation of multiple motile cilia. *Nat Comms* 5, 4418 (2014)). In order to precisely quantitate this length defect, axonemes from ALI cultures (Ostrowski L E in Cell Biology (ed. Celis J E) 99-102 (Elsevier, 2005)) (FIG. 9B) were biochemically isolated and these preparations were subjected to negative stain EM followed by measurement of individual cilia. Isolated NEK10$^{G>C}$ cilia were indeed short (FIG. 4C-4D, 7.86±1.06 μm vs. 6.24±1.26 μm), providing at least a partial basis for ciliary transport failure based on biophysical models for mucociliary transport which include ciliary length as a critical parameter in force generation (Leopold et al. Smoking Is Associated with Shortened Airway Cilia. *PLoS ONE* 4, e8157 (2009); Oltean et al. Quantifying Ciliary Dynamics during Assembly Reveals Stepwise Waveform Maturation in Airway Cells. *Am. J. Respir. Cell Mol. Biol* 59, 511-522 (2018); and Bottier et al. How Does Cilium Length Affect Beating?*Biophysical Journal* 116, 1292-1304 (2019)).

Figure 4E:
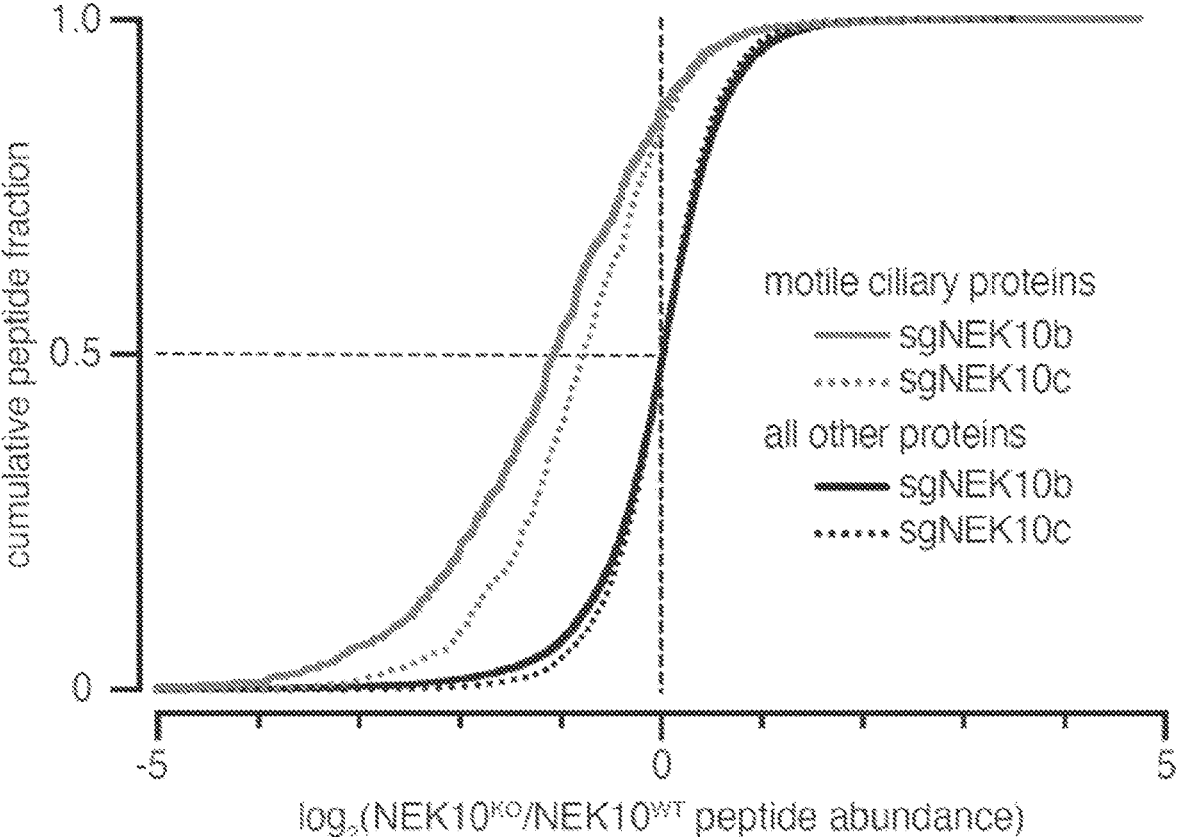
Figure 5E:
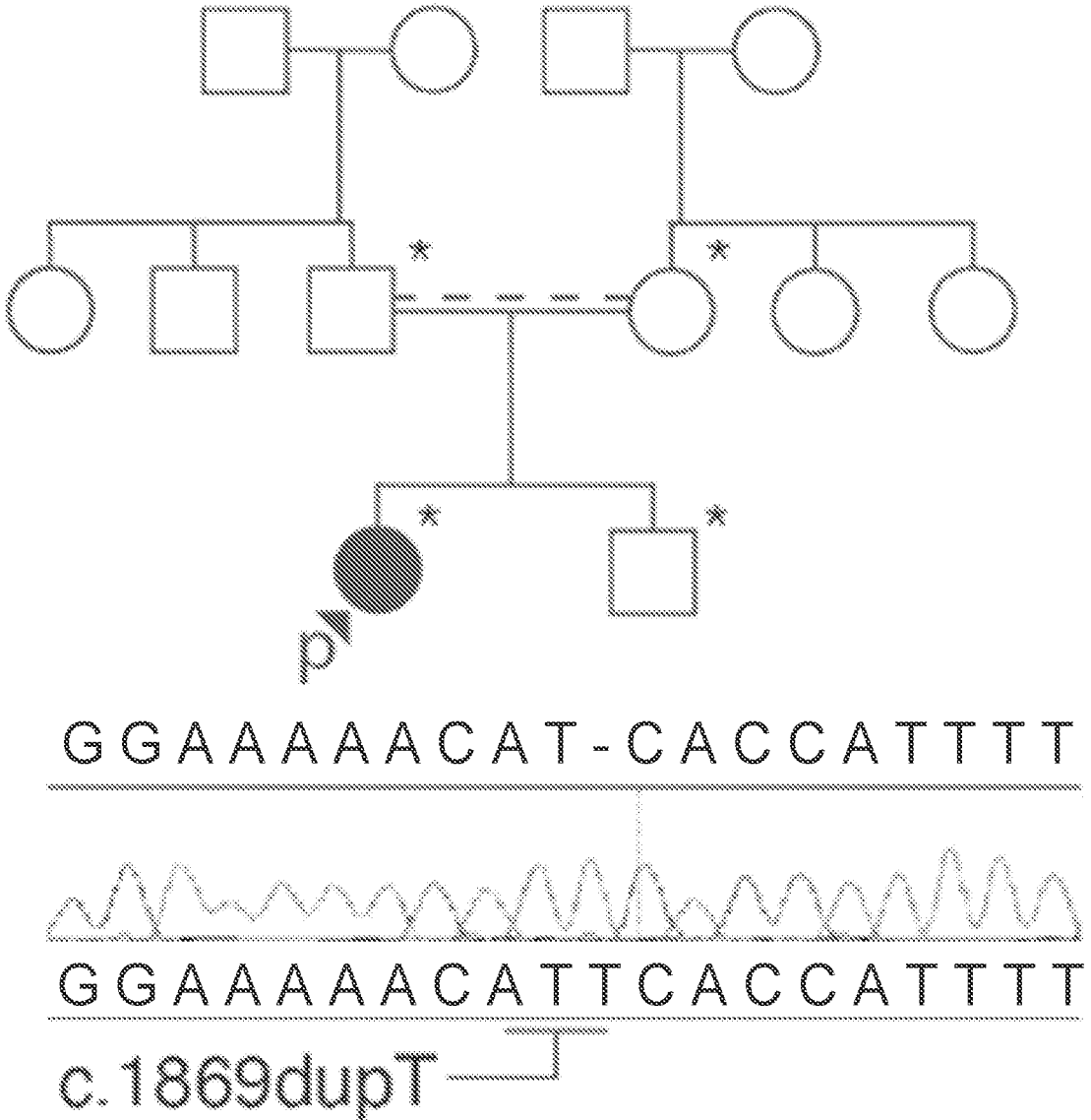
FIG. 5E includes a pedigree of kindred 2, asterisks denote family members from whom genomic DNA was available; dashed line indicates consanguinity by shared tribal ancestry, Sanger sequencing trace confirming c.1869dupT.
Figure 5F:
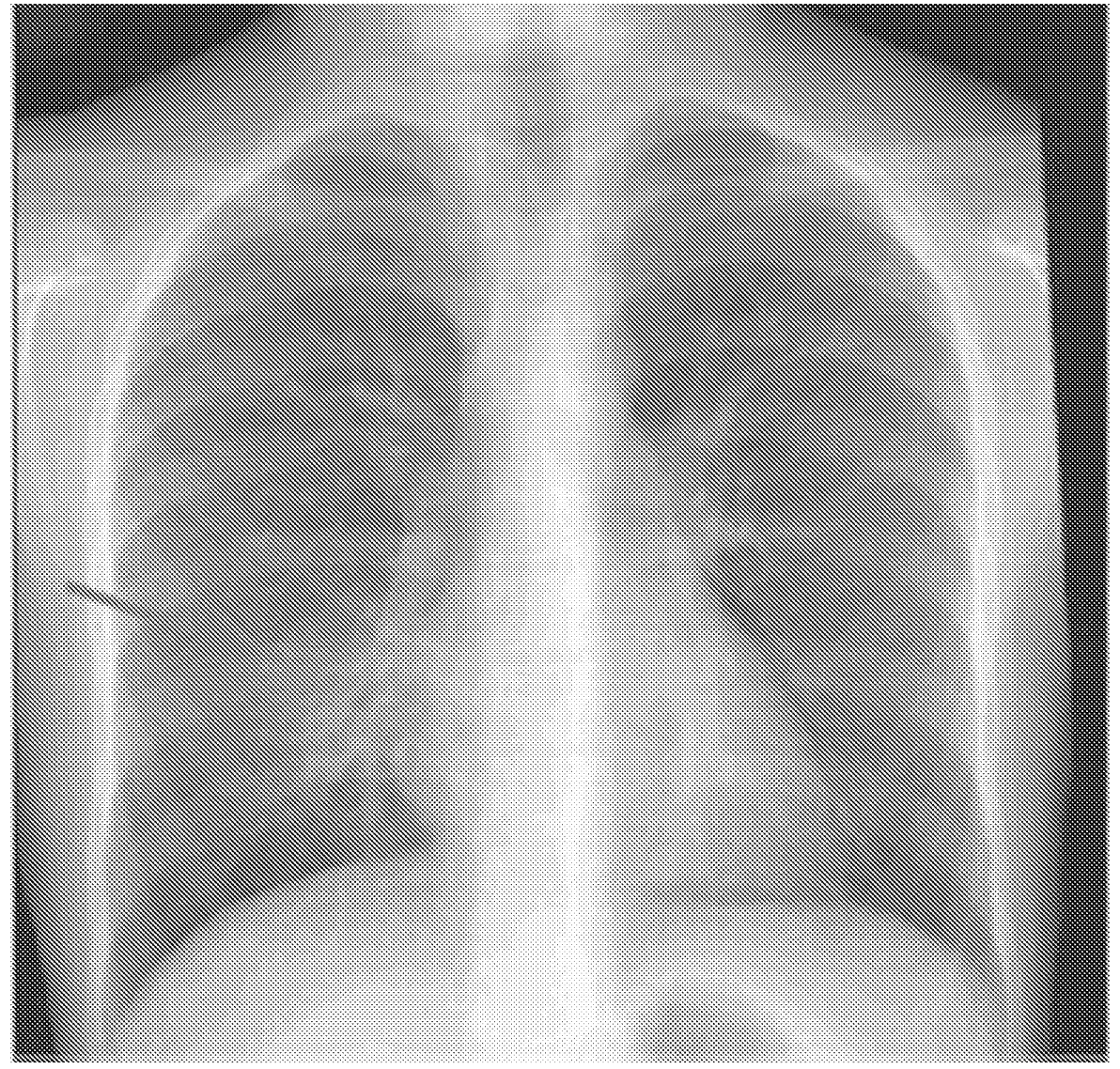
FIG. 5F includes a representative image of a chest radiograph of proband 2, arrow highlights bronchiectasis.
Figure 5J:
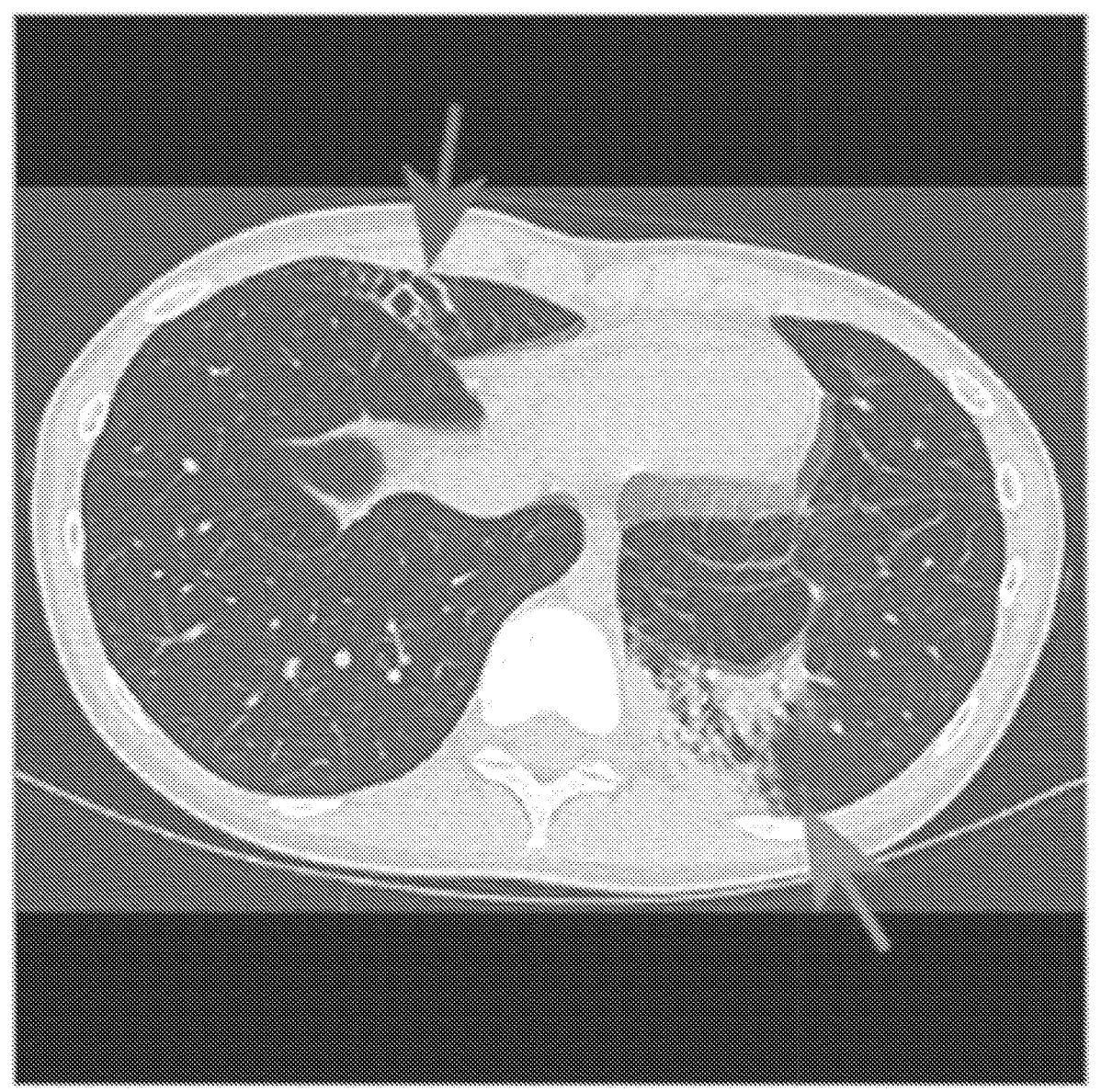
FIG. 5J includes a representative image of CT from proband 4 indicating right middle lobe (arrow) and left lower lobe (arrow) bronchiectasis.
Figure 5K:
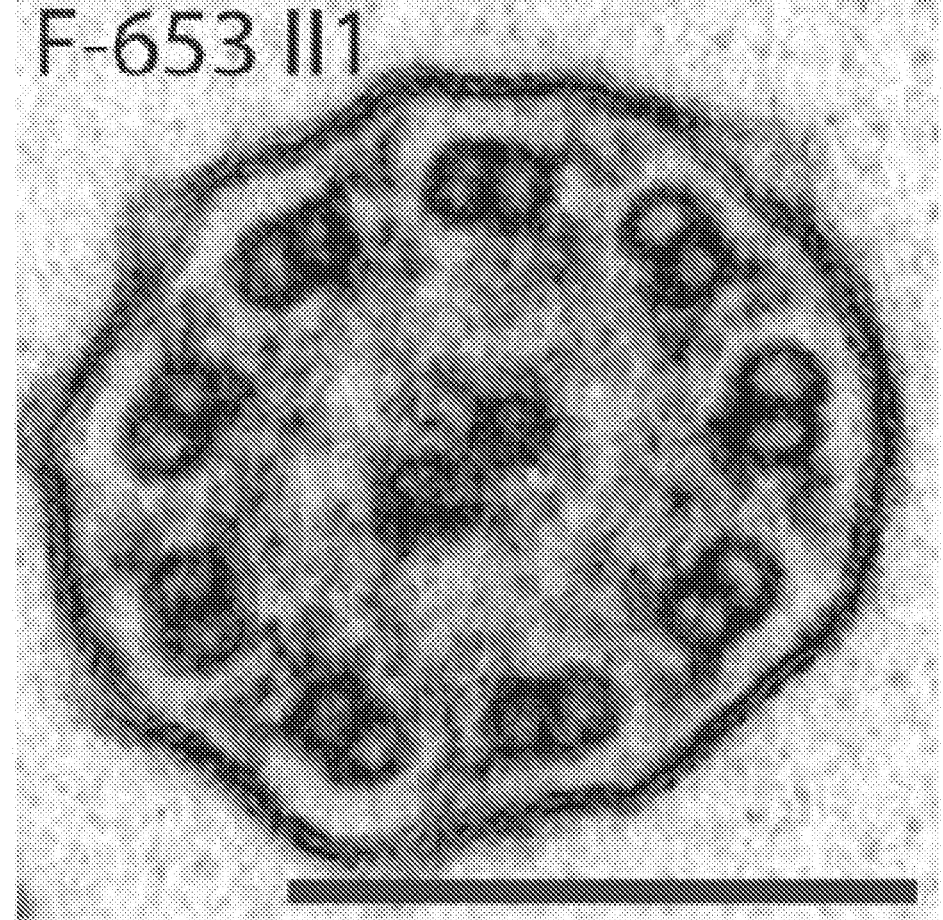
FIG. 5K includes a representative image of proband 4 nasal biopsy TEM demonstrating normal radial ciliary ultrastructure, scale bar 200 nm.
Figure 5M:
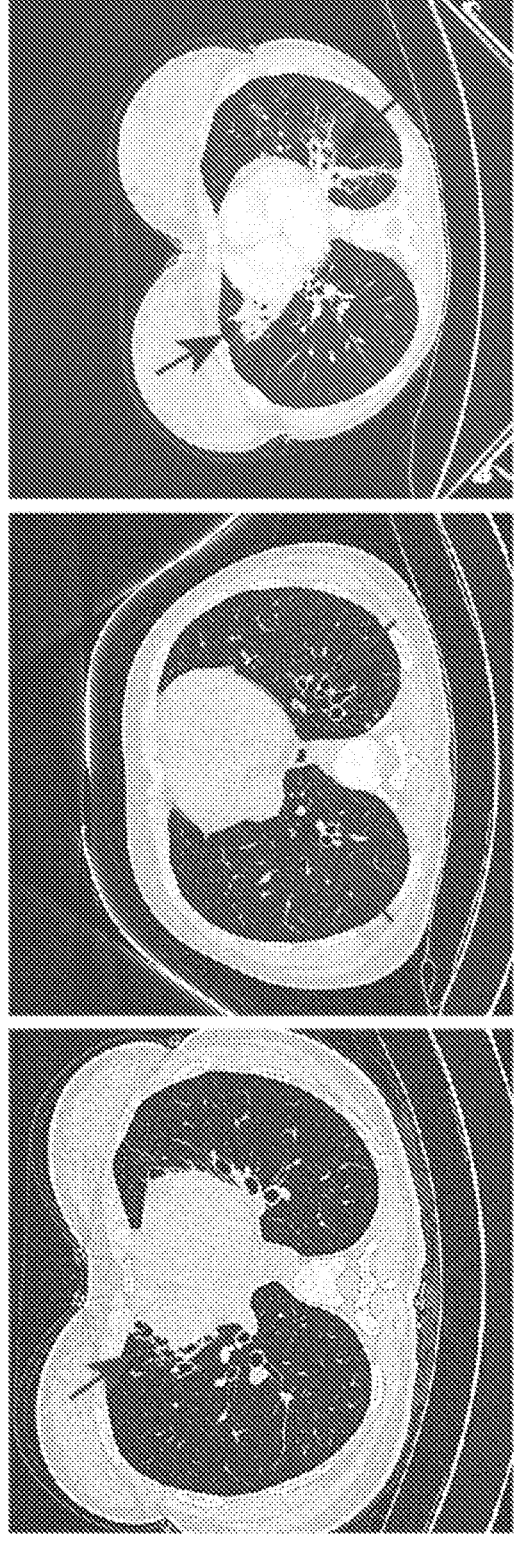
FIG. 5M includes representative images from CTs of affected siblings in (FIG. 5L) demonstrating bronchiectasis.
Figure 5N:
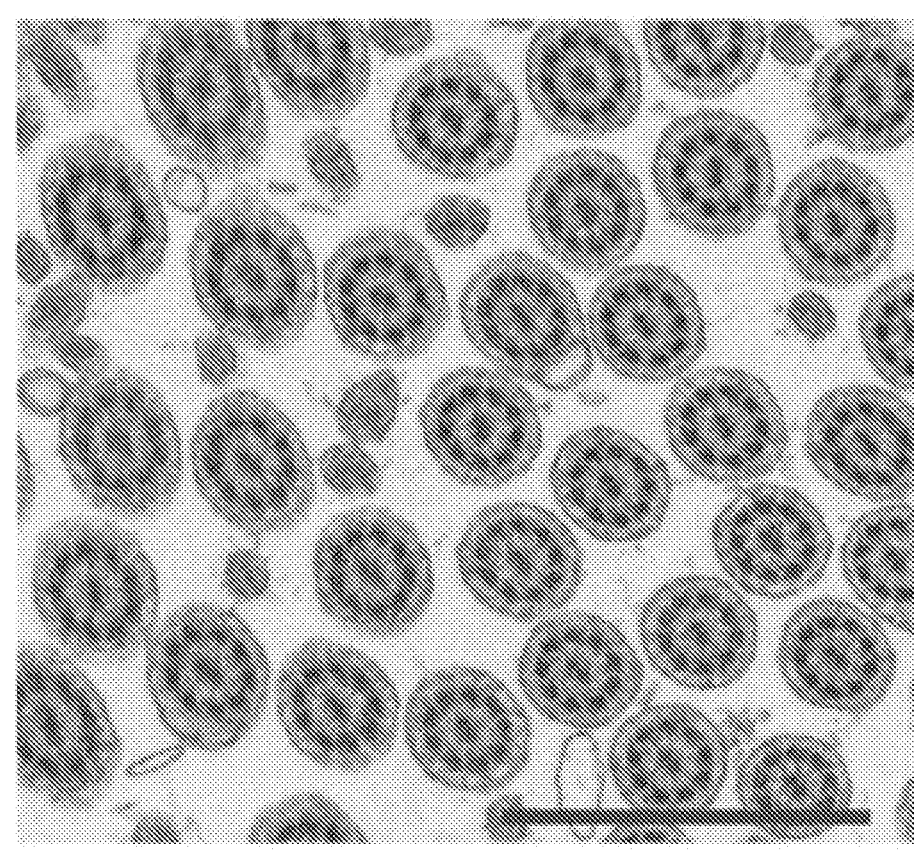

In order to explore the biochemical functions of NEK10 in airway epithelium, iron-enrichment proteomics (LC-IMAC MS2) (Block et al. Chapter 27 Immobilized-Metal Affinity Chromatography (IMAC): A Review. Methods in Enzymology 463, 439-473 (2009)) was next performed, thereby identifying a set of depleted phosphopeptides upon NEK10 inactivation in ALI (FIG. 5C). Gene ontology analysis (Ashburner et al. Gene Ontology: tool for the unification of biology. *Nat Genet* 25, 25-29 (2000); and The Gene Ontology Consortium. The Gene Ontology Resource: 20 years and still GOing strong. *Nucleic Acids Res* 47, D330-D338 (2019)) revealed these depleted peptides to be highly enriched for ciliary motility and axonemal assembly genes, suggesting a large complement of ciliary proteins are dysregulated upon NEK10 loss (FIG. 5D). To test this hypothesis directly, the effects of NEK10 deletion on the set of proteins previously proteomically identified in airway cilia (Ostrowski et al. A Proteomic Analysis of Human Cilia Identification of Novel Components. *Mol Cell Proteomics* 1, 451-465 (2002)) was analyzed, which exposed a striking and highly significant depletion of such ciliary phosphopeptides (median log 2 fold change–1.06 (sgNEK10b), –0.771 (sgNEK10c), FIG. 4E). Notably, while we observed similar findings upon analysis of peptides mapping to annotated PCD genes, little to no depletion of peptides from non-PCD ciliopathy genes was observed, consistent with NEK10 specifically regulating motile ciliogenesis (FIGS. 5E-5F). Peptides from virtually all classes of motile ciliary genes were depleted in NEK10$^{KO}$ ALI (FIG. 4F) including axone-mal motors, IFT components, central pair constituents, and ciliary length control proteins—indicating that a diverse array of the ciliary proteome is directly or indirectly dysregulated upon NEK10 loss and providing a rich data set for future efforts to dissect its target network.

OTHER EMBODIMENTS

All of the features disclosed in this specification can be combined in any combination. Each feature disclosed in this specification can be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments can be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases can encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

---

What is claimed is:

1. A method of treating bronchiectasis, the method comprising administering to a subject in need thereof a vector comprising a nucleic acid encoding Never In Mitosis Gene A-Related Kinase 10 (NEK10).

2. The method of claim 1, wherein NEK10 is wild-type NEK10 comprising SEQ ID NO: 1.

3. The method of claim 1, wherein NEK10 is a NEK10 mutant comprising an amino acid substitution at position S684.

4. The method of claim 3, wherein the amino acid substitution at position S684 is S684D.

5. A method of diagnosing a subject as having bronchiectasis, the method comprising:

providing a sample from the subject; and detecting a mutation in NEK10 in the sample, wherein presence of the mutation in NEK10 indicates that the subject has bronchiectasis; or detecting a level of NEK10 in the sample and comparing the level of NEK10 in the sample to a reference level, wherein presence of a level of NEK10 in the sample that is below the reference level indicates that the subject has bronchiectasis.

6. The method of claim 5, wherein the mutation in NEK10 is selected from the group consisting of NM_152534: c.1230+5G>C (insertion of VTALLLK), NM_152534: c.1869dupT (H624Sfs*4), NM_152534:c.2243C>T (P748L), NM_152534:c.1373+1G>T (C437Tfs*9), and NM_152534:c.2317C>T (R773C).

7. The method of claim 5, further comprising treating the subject with a therapy selected from the group consisting of a nucleic acid encoding NEK10 or a mutant thereof, a bronchodilator, an antibiotic, an expectorant, oxygen therapy, chest physiotherapy, an anti-inflammatory agent, and a mucolytic.

8. The method of claim 7, wherein NEK10 encoded by the nucleic acid is wild-type NEK10 comprising SEQ ID NO: 1.

9. The method of claim 7, wherein NEK10 encoded by the nucleic acid is a NEK10 mutant comprising an amino acid substitution at position S684.

10. The method of claim 9, wherein the amino acid substitution at position S684 is S684D.

11. The method of claim 5, wherein the sample is a blood sample or a tissue sample.

12. The method of claim 5, wherein the sample is obtained from a subject having or at risk for having bronchiectasis.

13. A method of increasing mucociliary transport (MCT) in an airway epithelium, the method comprising administering a vector comprising a nucleic acid encoding NEK10 to the airway epithelium.

14. The method of claim 13, wherein NEK10 is wild-type NEK10 comprising SEQ ID NO: 1.

15. The method of claim 13, wherein NEK10 is a NEK10 mutant comprising an amino acid substitution at position S684.

16. The method of claim 15, wherein the amino acid substitution at position S684 is S684D.

* * * * *